(12) United States Patent
Dehesh

(10) Patent No.: US 6,660,849 B1
(45) Date of Patent: Dec. 9, 2003

(54) PLANT FATTY ACID SYNTHASES AND USE IN IMPROVED METHODS FOR PRODUCTION OF MEDIUM-CHAIN FATTY ACIDS

(75) Inventor: Katayoon Dehesh, Vacaville, CA (US)

(73) Assignee: Calgene LLC, Davis, CA (US)

( * ) Notice: Subject to any disclaimer, the term of this patent is extended or adjusted under 35 U.S.C. 154(b) by 0 days.

(21) Appl. No.: 09/057,996

(22) Filed: Apr. 9, 1998

Related U.S. Application Data

(60) Provisional application No. 60/041,815, filed on Apr. 11, 1997.

(51) Int. Cl.$^7$ .............................................. C07H 21/04
(52) U.S. Cl. ...................................... 536/23.6; 536/23.2
(58) Field of Search .................................. 800/281, 298; 435/69.1, 468, 419; 536/23.6, 23.2

(56) References Cited

FOREIGN PATENT DOCUMENTS

| WO | WO92/03564 | 3/1992 |
| WO | WO94/10189 | 5/1994 |
| WO | WO95/06740 | 3/1995 |
| WO | WO96/23892 | 8/1996 |

OTHER PUBLICATIONS

Slabaugh et al, GenEMBL Sequence Accession No. U67316,1996.*
Dehesh, K. "KAS IV: a 3–ketoacyl–ACP synthase from Cuphea sp. Is a medium chain specific condensing enzyme" *The Plant Journal* 1998 15(3), pp. 383–390.
Topfer, R. Modification of Plant Lipid Synthesis *Science* 1995 vol. 268 pp. 681–686.
Schuch, R. "Mediem–chain acyl–ACP thioesterase is not the exclusive enzyme responsible for early chain–lenght termination in medium–chain fatty acid synthesis" *Grasas y Aceites* 1993 vol. 44 Fasc 2 pp. 126–128.
Martini, N. "Modification of Fatty Acid Composition in the Storage Oil of Transgenic Rapeseed" *Biological Chemistry Hoppe–Seyler* vol. 376 1995 pp. S55 XP002014021.
Fuhrmann, et al., "Factors Controlling Medium–Chain Fatty Acid Synthesis in Plastids from Maturing Cuphea Embryos" *Z. Naturforsch* 48c,616–622 (1993).
Shimakata, et al., "Isolation and function of spinach leaf β–ketoacyl–(acyl–carrier–protein) synthases" *Proceedings of National Academy of Science*, USA vol. 79:5508–5812 (1982).
Walsh, et al., "The Short Chain Condensing enzyme has a widespread occurrence in the Fatty Acid synthetases from higher plants", *Phytochemistry* vol. 29 No. 12 pp 3797–3799 (1990).
Voelker, et al., "Plant Acyl–Acp Thioesterases: Chain–length determining enzymes in plant fatty acid biosynthesis" *Genetic Engineering* vol. 18 pp. 111–113.

Tsay, et al, "Isolation and characterization of the β–Ketoacyl–acyl Carrier Protein Synthase III Gene (fabH) from *Escherichia coli* K–12" vol. 267, No. 10 pp. 6807–6814 (1992).
Voelker, et al., "Fatty Acid biosynthesis Redirected to Medium–chains in Transgenic Oilseed Plants" *Science* vol. 257 pp. 72–74.
Slabaugh, et al., "Condensing enzymes from *Cuphea wrightii* associated with medium chain fatty acid biosynthesis" *The Plant Journal* 13(5), 611–620.
Slabaugh, et al., "cDNA Clones Encoding β–Ketoacyl–Acyl Carrier Protein Synthase III from *Cuphea wrightii*" *Plant Physiology* 108:443–444 (1995).
Tai, et al., "3–ketoacyl–Acyl Carrier Protein Synthase III from Spinach (*Spinacia oleracea*) Is not Similar to Other Condensing Enzymes of Fatty Acid Synthase" *Plant Physiology* 103:1361–1367 (1993).
Voelker, et al., "Genetic engineering of a quantitative trait: metabolic and genetic parameters influencing the accumulation of laurate in rapeseed" *The Plant Journal* 9(2)pp. 229–241 (1996).
Siggard–Andersen, et al., "The fabJ–encoded β–Ketoacyl–(Acyl carrier protein) synthase IV from *Escherichia coli* is sensitive to cerulenin and specific for short–chain substrates" *Proc. Natl. Acad. Sci*, USA vol. 91, pp: 11027–11031 (1994).
Leonard, et al., "A Cuphea β–ketoacyl–Acp synthase shifts the synthesis of fatty acids towards shorter chains in Arabidopsis seeds expressing Cuphea FatB thioesterases" *The Plant Journal* 13(5 pp:621–628 (1998).
Post–Beittenmiller, et al. "In vivo Pools of Free and Acylated Acyl Carrier Proteins in Spinach" *The Journal of Biological Chemistry* vol. 266, No. 3 pp: 1858–1865 (1991).
Radke, et al., "Transformation of *Brassica napus* L. using *Agrobacterium Tumefaciens*: developmentally regulated expression of a reintroduced napin gene" *Theor. Appl. Genet* 75:685–694 (1988).
Kauppinen, Sakari "Structure and Expression of the Kas12 Gene Encoding a β–Ketoacyl–Acyl Carrier Protein synthase IIsozyme from Barley" *The Journal of Biological Chemistry* vol. 267. No. 33 pp:23999–24006 (1992).

(List continued on next page.)

*Primary Examiner*—Elizabeth F. McElwain
(74) *Attorney, Agent, or Firm*—Sonnenschein Nath & Rosenthal; G. Harley Blosser; Kevin W. Buckley

(57) ABSTRACT

By this invention, compositions and methods of use related to β-ketoacyl-ACP synthases. Of special interest are synthases obtainable from Cuphea species. Amino acid and nucleic acid for synthase protein factors are provided, as well as methods to utilize such sequences in constructs for production of genetically engineered plants having altered fatty acid compositions. Of particular interest is the expression of synthase protein factors in conjunction with expression of plant medium-chain acyl-ACP thioesterases for production of increased levels and/or modified ratios of medium-chain fatty acids in oils of transgenic plant seeds.

2 Claims, 60 Drawing Sheets

OTHER PUBLICATIONS

Jaworski, et al., "A Cerulenin Insensitive Short Chain 3–ketoacyl–Acyl Carrier Protein Synthase in *Spinacia oleracea* Leaves" *Plant Physiology* vol. 90 pp: 41–44 (1989).

Eccleston, et al., "Expression of Lauroyl–Acyl Carrier Protein Thioesterase In Brassica napus Seeds Induces Pathways for both Fatty Acid Oxidation and Biosynthesis and Implies a Set Point for Triacylglycerol Accumulation" *The Plant Cell*, vol. 10:613–621 (1998).

Hawkins, et al., "Characterization of acyl–ACP thioesterases of mangosteen (Garcinia mangostana) seed and high levels of stearate production in transgenic canola" *The Plant Journal* vol. 13(6), 743–752 (1998).

Harwood, John L. "Fatty Acid Metabolism" *Ann. Rev. Plant Physiol. Plant Mol. Biol.* 39:101–138 (1988).

Dehesh, et al., "Production of high levels of 8:0 and 10:0 fatty acids in transgenic canola by overexpression of Ch FatB2, a thioesterase cDNA from *Cuphea hookeriana*" *The Plant Journal* vol. 9(2), 167–172 (1996).

Dehesh, et al., "Two Novel Thioesterases are Key Determinants of the Bimodal Distribution of Acyl Chain Length of *Cuphea palustris* Seed Oil" *Plant Physioll.* 110:203–210 (1996).

Dehesh, et al., "GT–2: a transcription factor with twin autonomous DNA–binding domains of closely related but different target sequence specificity" *The EMBO Journal* vol. 11. No. 11, pp: 4131–4144 (1992).

Clough, et al., "Purification and Characterization of 3–Ketoacyl–Acyl Carrier Protein synthase III from Spinach" *The Hournal of Biological Chemistry* vol. 267, No. 29: 20992–20998 (1992).

* cited by examiner

```
AGC TCC ACC GCG GTG GCG GCC GCT CTA GAA CTA GTG GAT CCC CCG GGC    48
Ser Ser Thr Ala Val Ala Ala Ala Leu Glu Leu Val Asp Pro Pro Gly

TGC AGG AAT TCG GCA CGA GCC GAT CTC GGT GCC GAC CGC CTC TCC AAG    96
Cys Arg Asn Ser Ala Arg Ala Asp Leu Gly Ala Asp Arg Leu Ser Lys

ATC GAC AAG GAG AGA GCC GGA GTG CTG GTC GGA ACA GGA ATG GGT GGT   144
Ile Asp Lys Glu Arg Ala Gly Val Leu Val Gly Thr Gly Met Gly Gly

CTG ACT GTC TTC TCT GAC GGG GTT CAG TCT CTT ATC GAG AAG GGT CAC   192
Leu Thr Val Phe Ser Asp Gly Val Gln Ser Leu Ile Glu Lys Gly His

CGG AAA ATC ACC CCT TTC TTC ATC CCC TAT GCC ATT ACA AAC ATG GGG   240
Arg Lys Ile Thr Pro Phe Phe Ile Pro Tyr Ala Ile Thr Asn Met Gly

TCT GCC CTG CTC GCT ATC GAA TTT GGT CTC ATG GGC CCA AAC TAT TCA   288
Ser Ala Leu Leu Ala Ile Glu Phe Gly Leu Met Gly Pro Asn Tyr Ser

ATT TCC ACT GCA TGT GCC ACT TCC AAC TAC TGC TTC CAT GCT GCC GCT   336
Ile Ser Thr Ala Cys Ala Thr Ser Asn Tyr Cys Phe His Ala Ala Ala

AAT CAT ATC CGC CGT GGT GAG GCT GAT CTT ATG ATT GCT GGA GGC ACT   384
Asn His Ile Arg Arg Gly Glu Ala Asp Leu Met Ile Ala Gly Gly Thr
```

FIGURE 1
1/4

```
GAG GCC GCA ATC ATT CCA ATT GGG TTG GGA GGC TTT GTG GCT TGC AGG    432
Glu Ala Ala Ile Ile Pro Ile Gly Leu Gly Gly Phe Val Ala Cys Arg

GCT TTG TCT CAA AGG AAC GAT GAC CCG CAG ACT GCC TCT AGG CCC TGG    480
Ala Leu Ser Gln Arg Asn Asp Asp Pro Gln Thr Ala Ser Arg Pro Trp

GAT AAA GAC CGT GAT GGT TTT GTG ATG GGT GAA CAT GCT GGA GTG TTG    528
Asp Lys Asp Arg Asp Gly Phe Val Met Gly Glu His Ala Gly Val Leu

GTG ATG GAG AGC TTG GAA CAT GCA ATG AGA CGA GGA GCA CCG ATT ATT    576
Val Met Glu Ser Leu Glu His Ala Met Arg Arg Gly Ala Pro Ile Ile

GCA GAG TAT TTG GGA GGT GCA ATC AAC TGT GAT GCT TAT CAC ATG ACT    624
Ala Glu Tyr Leu Gly Gly Ala Ile Asn Cys Asp Ala Tyr His Met Thr

GAT CCA AGG GCT GAT GGT CTT GGT GTC TCT TCT TGC ATT GAG AGT AGC    672
Asp Pro Arg Ala Asp Gly Leu Gly Val Ser Ser Cys Ile Glu Ser Ser

CTT GAA GAT GCT GGC GTC TCA CCT GAA GAG GTC AAT TAC ATA AAT GCT    720
Leu Glu Asp Ala Gly Val Ser Pro Glu Glu Val Asn Tyr Ile Asn Ala
```

FIGURE 1
2/4

```
CAT GCG ACT TCT ACT CTA GCT GGG GAT CTC GCC GAG ATA AAT GCC ATC    768
His Ala Thr Ser Thr Leu Ala Gly Asp Leu Ala Glu Ile Asn Ala Ile

AAG AAG GTT TTC AAG AAC ACA AAG GAT ATC AAA ATT AAT GCA ACT AAG    816
Lys Lys Val Phe Lys Asn Thr Lys Asp Ile Lys Ile Asn Ala Thr Lys

TCA ATG ATC GGA CAC TGT CTT GGA GCA TCT GGA GGT CTT GAA GCT ATA    864
Ser Met Ile Gly His Cys Leu Gly Ala Ser Gly Gly Leu Glu Ala Ile

GCG ACT ATT AAG GGA ATA AAC ACC GGC TGG CTT CAT CCC AGC ATT AAT    912
Ala Thr Ile Lys Gly Ile Asn Thr Gly Trp Leu His Pro Ser Ile Asn

CAA TTC AAT CCT GAG CCA TCG GTG GAG TTC GAC ACT GTT GCC AAC AAG    960
Gln Phe Asn Pro Glu Pro Ser Val Glu Phe Asp Thr Val Ala Asn Lys

AAG CAG CAA CAC GAA GTT AAC GTT GCG ATC TCG AAT TCA TTC GGA TTT   1008
Lys Gln Gln His Glu Val Asn Val Ala Ile Ser Asn Ser Phe Gly Phe

GGA GGC CAC AAC TCA GTC GTG GCT TTC TCG GCT TTC AAG CCA TGATTA    1056
Gly Gly His Asn Ser Val Val Ala Phe Ser Ala Phe Lys Pro
```

FIGURE 1
3/4

```
CCCATTTCAC AAGGTACTTG TCATTGAGAA TACGGATTAT GGACTTGCAG AGTAATTTCC    1116
CCATGTTTGT CGGAAGAGCA TATTACCACG GTTGTCCGTC AAACCCATTT AGGATACTGT    1176
TCTATGTAAT AAAACTAAGG ATTATTAATT TCCCTTTTAA TCCTGTCTCC AGTTTGAGCA    1236
TGAAATTATA TTTATTTTAT CTTAGAAAGG TCAAATAAGA TTTGTTTTA CCTCTGTAAA     1296
ACTTTGTTT GTATTGGAAA GGAAGTGCCG TCTCAAAAAA AAAAAAAAA AA              1348
```

Sequence Range: 1 to 1704

```
                10              20              30              40
AAA TTA ACC CTC ACT AAA GGG AAC AAA AGC TGG AGC TCC ACC GNG GTG
Lys Leu Thr Leu Thr Lys Gly Asn Lys Ser Trp Ser Ser Thr Xxx Val>
 50              60              70              80              90
GCG GCC GCT CTA GAA CTA GTG GAT CCC CCG GGC TGC AGG AAT TCG GCA
Ala Ala Ala Leu Glu Leu Val Asp Pro Pro Gly Cys Arg Asn Ser Ala>
100             110             120             130             140
CGA GCC GGC ATG GGC CTC GTC TCC GTA TTC GGC TCC GAC GTC GAC TCT
Arg Ala Gly Met Gly Leu Val Ser Val Phe Gly Ser Asp Val Asp Ser>
150             160             170             180             190
TAT TAC GAA AAG CTC CTC TCC GGC GAG AGC GGG ATC AGC TTA ATC GAC
Tyr Tyr Glu Lys Leu Leu Ser Gly Glu Ser Gly Ile Ser Leu Ile Asp>
200             210             220             230             240
CGC TTC GAC GCT TCC AAG TTC CCC ACC AGG TTC GGC GCG CAG ATC CGG
Arg Phe Asp Ala Ser Lys Phe Pro Thr Arg Phe Gly Gly Gln Ile Arg>
250             260             270             280             
GGA TTC AAC GCG ACG GGA TAC ATC GAC TAC GGG AAG AAC GAC AGG AGG CTC
Gly Phe Asn Ala Thr Gly Tyr Ile Asp Tyr Gly Lys Asn Asp Arg Arg Leu>
290             300             310             320             330
GAC GAT TGC CTC CGC TAC TGC ATT GTC GCC GGG AAG AAG GCT CTC GAA
Asp Asp Cys Leu Arg Tyr Cys Ile Val Ala Gly Lys Lys Ala Leu Glu>
```

FIGURE 2
1/5

```
340              350              360              370              380
AAT TCC GAT CTC GGC GGT GAA AGC CTC TCC AAG ATT GAT AAG GAG AGA
Asn Ser Asp Leu Gly Gly Glu Ser Leu Ser Lys Ile Asp Lys Glu Arg>
                 390              400              410          420          430
GCT GGA GTG CTA GTT GGA ACT GGT ATG GGT GGC CTA ACC GTC TTC TCT
Ala Gly Val Leu Val Gly Thr Gly Met Gly Gly Leu Thr Val Phe Ser>
                     440              450              460              470              480
GAC GGG GTT CAG AAT CTC ATC GAG AAA GGT CAC CGG AAG ATC TCC CCG
Asp Gly Val Gln Asn Leu Ile Glu Lys Gly His Arg Lys Ile Ser Pro>
                 490              500              510          520
TTT TTC ATT CCC TAT GCC ATT ACA AAC ATG GGG TCT GCT CTG CTT GCC
Phe Phe Ile Pro Tyr Ala Ile Thr Asn Met Gly Ser Ala Leu Leu Ala>
    30           540              550              560              570
ATC GAT TTG GGT CTG ATG GGC CCA AAC TAT TCG ATT TCA ACT GCA TGT
Ile Asp Leu Gly Leu Met Gly Pro Asn Tyr Ser Ile Ser Thr Ala Cys>
580              590              600              610          620
GCT ACT TCC AAC TAC TGC TTT TAT GCC GCT AAT CAT ATC CGC CGA
Ala Thr Ser Asn Tyr Cys Phe Tyr Ala Ala Asn His Ile Arg Arg>
         630              640              650              660          670
GGC GAG GCT GAC CTC ATG ATT GCT GGA GGA ACT GAG GCT GCA ATC ATT
Gly Glu Ala Asp Leu Met Ile Ala Gly Gly Thr Glu Ala Ala Ile Ile>
```

```
                                                                                          720
                                                              710                           *
                                       700                                              AGG
                                                          TGC  AGG  GCT  TTA  TCT  CAA  Arg>
                         690                          GTT  GCC              Leu  Ser  Gln
             680                              GGA  TTC      Ala  Cys  Arg  Ala
                                   GGG  TTA        Gly  Phe  Val
                     CCA  ATT          Gly  Leu  Gly
                             Pro  Ile                       740              760
                                           730                         750                    810
                                                                                      GAT
                                                            TCA  AGG  CCG  TGG  GAT  AAG  GAC  CGT
                     AAT  GAT  GAC  CCT  CAG  ACT  GCC  Ala  Ser  Arg  Pro  Trp  Asp  Lys  Arg  Asp>
                     Asn  Asp  Asp  Pro  Gln  Thr
                     70        780                      790          800
                                  *
                                                                                         860
                                                                   850
                                                         840
                                                 GGA  GTA  TTG  GTT  ATG  GAG  AGC  TTG
                         GGC  GAA  GGG  GCT  Gly  Val  Leu  Val  Met  Glu  Ser  Leu>
                 GTG  ATG  Met  Gly  Glu  Gly  Ala
         GGT  TTT  Phe  Val
         Gly                                              880          890          900      910
                 820          830                                                      *
                                                                                                960
                                                                                                *
                                                                              940          950
                                                                   930
                                                         920
                                                 TAT  CAT  ATG  ACT  GAT  CCA  AGG  GCT  GAT
                         GAT  GCT  Tyr  His  Met  Thr  Asp  Pro  Arg  Ala  Asp>
                 AAT  TGT  Asp  Ala
         GGA  GTC  Val  Asn  Cys
         Gly  Ala                                880
                     870

1000
                                                                 980          990
                                                         970
                                                 GTC  TCC  TCT  TGC  ATT  GAG  AGC  AGT  CTG  GAA  GAT  GCT  GGG
                         CTT  GGT  Leu  Gly  Val  Ser  Ser  Cys  Ile  Glu  Ser  Ser  Leu  Glu  Asp  Ala  Gly>
                 GGG  Gly                         980          990          1000
                                                 GTC  TCA  CCT  GAA  GAG  GTC  AAT  TAC  ATA  AAT  GCT  CAT  GCG  ACT  TCC  ACT
                                                 Val  Ser  Pro  Glu  Glu  Val  Asn  Tyr  Ile  Asn  Ala  His  Ala  Thr  Ser  Thr>
```

FIGURE 2
3/5

```
10         1020         1030         1040         1050
            *
CTT GCT GGG GAT CTT CCC GAG ATA AAT GCC ATC AAG AAG GTT TTC AAG
Leu Ala Gly Asp Leu Ala Glu Ile Asn Ala Ile Lys Lys Val Phe Lys>
     1060         1070         1080         1090         1100
                                     *
AAC ACC AAG GAA ATC ACA ATC AAT GCA ACT AAG TCG ATG ATC GGA CAC
Asn Thr Lys Glu Ile Thr Ile Asn Ala Thr Lys Ser Met Ile Gly His>
1110         1120         1130         1140         1150
                                *
TGT CTT GGA GCA TCA GGG GGT CTT GAA GCC ATT GCG ACA ATT AAG GGA
Cys Leu Gly Ala Ser Gly Gly Leu Glu Ala Ile Ala Thr Ile Lys Gly>
     1160         1170         1180         1190         1200
                                                            *
ATA ACC ACC GGC TGG CTT CAT CCC AGC ATA AAC CAA TTC AAT CCC GAG
Ile Thr Thr Gly Trp Leu His Pro Ser Ile Asn Gln Phe Asn Pro Glu>
     1210         1220         1230         1240
CCA TCA GTG GAA TTC GAC ACA GTT GCC AAC AAG AAG CAG CAA CAT GAA
Pro Ser Val Glu Phe Asp Thr Val Ala Asn Lys Lys Gln Gln His Glu>
50           1260         1270         1280         1290
         *
GTG AAT GTT GCT ATC TCA AAT TCA TTC AAG CCA TGA TTA CTC GGT TCA AAT GCA
Val Asn Val Ala Ile Ser Asn Ser Phe Gly Phe Lys Pro
1300         1310         1320         1330         1340
                           *
GTT GTA GCT TTC TCA GCC TTC AAG CCA TGA TTA CTC GGT TCA AAT GCA
Val Val Ala Phe Ser Ala Phe Lys Pro
```

FIGURE 2
4/5

```
AATTGTTGC TGAGACAGTG AGCTTCAACT TGCAGAGCAA TTTTTTACAT GCCTTGTCGT
CGGAAGAGCG TAATACCGGG ATAGTTCCTT GATAGTTCAT TTAGGATGTT TTACTGCAAT
AATCGAAGAT TATTTCCATT CTAATCCAGT CTCCGNCGAG TTTGAGAATC TATCTGTTTG
TATTAGAAAG AACGAGGCAA GATTTGTTT CAIGTTTGTG TTTGTATTAC TTTCTTTTTG
CCCTTGTCAA TGGCATTTAA GATAAGCTTA TAAAAAAAA AAAAAAAAA AAAACTCGAG
GGGGGCCCG GTACCCAATT CGCCCTATAG TGAGTCGTAT GACAATTCAC TGTCCGTCGG
```

FIGURE 2

Sequence Range: 1 to 2046

```
                    10         20         30         40         50         60
                                                                             *
             ACTAAAGGGA ACAAAAGCTG GAGCTCCACC GCGGTGGCGG CCGCTCTAGA ACTAGTGGAT
                    70         80         90        100        110        120
                                                                             *
             CCCCCGGGCT GCAGGAATTC GGCACGAGTT TTCTTACTTG GGTCGGCTCA GCTCAGGTGT
                   130        140        150        160
             TCCA ATG GCG ACC GCT TCT TGC ATG GTT GCG TCC CCT TTC TGT ACG TGG
                  Met Ala Thr Ala Ser Cys Met Val Ala Ser Pro Phe Cys Thr Trp
             170        180        190        200        210
                          *
             CTC GTA GCT GCA TGC ATG CCC ACT TCA TCC GAC AAC GAC CCA CGT TCC
             Leu Val Ala Ala Cys Met Pro Thr Ser Ser Asp Asn Asp Pro Arg Ser
                   220        230        240        250        260
                                          *
             CTT TCC CAC AAG CGG CTC TCC CGT CGC CGG AGG ACT CTC TCC
             Leu Ser His Lys Arg Leu Ser Arg Arg Arg Arg Thr Leu Ser
                   270        280        290        300        310
                                                    *
             TCC CAT TGC TCC CTC CGG GGA TCC ACC TTC CAA TGC CTC CCT TGC
             Ser His Cys Ser Leu Arg Gly Ser Thr Phe Gln Cys Leu Asp Pro Cys
                   320        330        340        350        360
                                                                *
             AAC CAG CAA CGC TTC CTC GGG GAT AAC GGA TTC GCT TCC CTC TTC GGA
             Asn Gln Gln Arg Phe Leu Gly Asp Asn Gly Phe Ala Ser Leu Phe Gly
```

FIGURE 3
1/6

```
                    370               380               390               400
TCC AAG CCT CTT CGT TCA AAT CGC GGC CAC CTG AGG CTC GGC CGC ACT
Ser Lys Pro Leu Arg Ser Asn Arg Gly His Leu Arg Leu Gly Arg Thr
410            420               430               440               450
TCC CAT TCC GGG GAG GTC GTG GCT GTG GCT ATG CAA CCT GCA CAG GAA
Ser His Ser Gly Glu Val Val Ala Val Met Gln Pro Ala Gln Glu
460            470               480               490               500
GTC TCC ACA AAT AAG AAA CCT GCT ACC AAG CAA AGG CGA GTA GTT GTG
Val Ser Thr Asn Lys Lys Pro Ala Thr Lys Gln Arg Arg Val Val Val
510            520               530               540               550
ACA GGT ATG GGC GTG GTG ACT CCT CTA GGC CAT GAC CCC GAT GTT TAC
Thr Gly Met Gly Val Val Thr Pro Leu Gly His Asp Pro Asp Val Tyr
560            570               580               590               600
TAC AAC AAT CTC CTA GAC GGA ATA AGT GGC ATA GAG AGT GAG ATA GAG AAC
Tyr Asn Asn Leu Leu Asp Gly Ile Ser Gly Ile Glu Ser Glu Ile Glu Asn
610            620               630               640
TTC GAC TGC TCT CAG TTT CCC ACG AGA ATT GCC GGA GAG ATC AAG TCT
Phe Asp Cys Ser Gln Phe Pro Thr Arg Ile Ala Gly Glu Ile Lys Ser
650            660               670               680               690
TTT TCC ACA GAT GGC TGG GTG GCC CCA AAG TTC TCC GAG AGG ATG GAC
Phe Ser Thr Asp Gly Trp Val Ala Pro Lys Phe Ser Glu Arg Met Asp
```

FIGURE 3
2/6

```
700
     AAG TTC ATG CTT TAC ATG CTG ACT GCA GGC AAG AAA GCA TTA GCA GAT
     Lys Phe Met Leu Tyr Met Leu Thr Ala Gly Lys Lys Ala Leu Ala Asp
750                760             770             780             790
                                                    *
     GGT GGA ATC ACT GAA GAT GCG ATG AAA GAG CTC AAT AAA AGA AAG TGT
     Gly Gly Ile Thr Glu Asp Ala Met Lys Glu Leu Asn Lys Arg Lys Cys
             800             810             820             830         840
                                                                          *
     GGA GTT CTC ATT GGC TCC GGA TTG GGC GGT ATG AAG GTA TTC AGC GAT
     Gly Val Leu Ile Gly Ser Gly Leu Gly Gly Met Lys Val Phe Ser Asp
                     850             860             870             880
     TCC ATT GAA GCT CTG AGG ACT TCA TAT AAG AAG ATC AGT CCC TTT TGT
     Ser Ile Glu Ala Leu Arg Thr Ser Tyr Lys Lys Ile Ser Pro Phe Cys
890             900             910             920             930
                 *
     GTA CCT TTT TCT ACC ACA AAT ATG GGA TCC GCT ATT CTT GCA ATG GAC
     Val Pro Phe Ser Thr Thr Asn Met Gly Ser Ala Ile Leu Ala Met Asp
940             950             960             970             980
                                 *
     TTG GGA TGG ATG GGC CCT AAC TAT TCG ATA TCA ACT GCC TGT GCA ACA
     Leu Gly Trp Met Gly Pro Asn Tyr Ser Ile Ser Thr Ala Cys Ala Thr

FIGURE 3
                            3/6
```

```
                          990          1000          1010          1020          1030
AGT AAC TTC TGT ATA CTG AAT GCT GCG AAC CAC ATA ATC AAA GGC GAA
Ser Asn Phe Cys Ile Leu Asn Ala Ala Asn His Ile Ile Lys Gly Glu
     1040          1050          1060          1070          1080
                                                                *
GCA GAC ATG ATG CTT TGT GGT GGC TCG GAT GCG GCC GTT TTA CCT GTT
Ala Asp Met Met Leu Cys Gly Gly Ser Asp Ala Ala Val Leu Pro Val
     1090          1100          1110          1120
GGT TTG GGA GGT TTC GTA GCA TGC CGA GCT TTG TCA CAG AGG AAT AAT
Gly Leu Gly Gly Phe Val Ala Cys Arg Ala Leu Ser Gln Arg Asn Asn
1130      1140          1150          1160          1170
          *
GAC CCT ACC AAA GCT TCG AGA CCA TGG GAC AGT AAT CGT GAT GGA TTT
Asp Pro Thr Lys Ala Ser Arg Pro Trp Asp Ser Asn Arg Asp Gly Phe
    1180          1190          1200          1210          1220
                                       *
GTG ATG GGA GAA GGA GCT GGA GTT TTA CTT GAG GAG TTA GAG CAT
Val Met Gly Glu Gly Ala Gly Val Leu Leu Glu Glu Leu Glu His
     1230          1240          1250          1260          1270
                                             *
GCA AAG AAA AGA GGT GCA ACC GCA ATT TAT GCG GAA TTT CTA GGT GGG AGT
Ala Lys Lys Arg Gly Ala Thr Ala Ile Tyr Ala Glu Phe Leu Gly Gly Ser
     1280          1290          1300          1310          1320
                                                               *
TTC ACT TGC GAC GCC TAC CAC ATG ACC GAG CCT CAC CCT GAA GGA GCT
Phe Thr Cys Asp Ala Tyr His Met Thr Glu Pro His Pro Glu Gly Ala
```

FIGURE 3
4/6

```
      1330           1340           1350           1360
GGT GTG ATC CTC TGC ATA GAG AAG GCC TTG GCT CAG TCC GGA GTC TCG
Gly Val Ile Leu Cys Ile Glu Lys Ala Leu Ala Gln Ser Gly Val Ser
1370           1380           1390           1400           1410
                 *
AGG GAA GAC GTA AAT TAC ATA AAT GCG CAT GCA ACT GCA ACT CCT GCT
Arg Glu Asp Val Asn Tyr Ile Asn Ala His Ala Thr Ser Thr Pro Ala
1420           1430           1440           1450           1460
                               *
GGA GAT ATC AAG GAA TAC CAA GCT CTC GCC CAC TGT TTC GGC CAA AAC
Gly Asp Ile Lys Glu Tyr Gln Ala Leu Ala His Cys Phe Gly Gln Asn
1470           1480           1490           1500           1510
                                             *
AGT GAG CTG AGA GTG AAT TCC ACC AAA TCG ATC GGT CAC CTT CTT
Ser Glu Leu Arg Val Asn Ser Thr Lys Ser Met Ile Gly His Leu Leu
1520           1530           1540           1550           1560
                                                           *
GGA GGA GCT GGT GGC GTA GAA GCA GTT GCA GTA CAG GCA ATA AGG
Gly Gly Ala Gly Gly Val Glu Ala Val Ala Val Gln Ala Ile Arg
1570           1580           1590           1600
ACA GGA TGG ATC CAT CCA AAT ATT AAT TTG GAA GAC CCG GAC GAA GGC
Thr Gly Trp Ile His Pro Asn Ile Asn Leu Glu Asp Pro Asp Glu Gly
1610           1620           1630           1640           1650
           *
GTC GAT GCA AAA CTG CTC GGC CCT AAG AAG AAG CTG AAG GTC
Val Asp Ala Lys Leu Leu Gly Pro Lys Lys Glu Lys Leu Lys Val
```

FIGURE 3
5/6

```
1660        1670        1680        1690        1700
AAG GTC GGT TTG TCC AAT TCA TTT GGG TTC GGC GGC CAT AAC TCA TCC
Lys Val Gly Leu Ser Asn Ser Phe Gly Phe Gly Gly His Asn Ser Ser
        1710        1720        1730        1740        1750        1760
ATA CTA TTT GCC CCC TGC AAC TAG A AAAGAGTCTG TGGAAGCCGA GAGTCTTTGA
Ile Leu Phe Ala Pro Cys Asn ***
        1770        1780        1790        1800        1810        1820
GAACTCATGC ACGTTAGTAG CTTCTTATGC CTCTGAAACC GAGATAGACC GGCTACTCGA
        1830        1840        1850        1860        1870        1880
GGGGATGCCA AAGATACTCC TTGCCGGTAT TGGTGTTAAG AGATCACTGC TTGTCCCTTT
        1890        1900        1910        1920        1930        1940
TATTTTCTTC TTCTTTTGAG AGCTTTAACC GAGGTAGTCG TATTTTCGAG CTTTTCGAAT
        1950        1960        1970        1980        1990        2000
ACATGTTCGT TATCGGATCA ATGTGTTTCT TCTAAGATCA TTTGTAATGC ATATTTTGAA
        2010        2020        2030        2040
AAACCACATC TCAGTATGCA AAATAAAAAA AAAAAAAAA AAAAAA
```

FIGURE 3
6/6

Sequence Range: 1 to 1921

```
         10         20         30         40         50         60
                                                                  *
        CGGCACGAGG TCACCTCTTA CCTCGCCTGC TTCGAGCCCT GCCATGACTA CTACACCTCC
         70         80         90        100        110        120
                                                                  *
        GCATCCTTGT TCGGATCCAG GCCCATCCGC ACCACCCGCA GGCACCGGAG GCTCAATCGA
        130        140        150        160        170        180
                                                                  *
        GCTTCCCCTT CCGGGGAGGC AATGGCTGTG GCTCTGCAAC CTGCACAGGA AGTTACCACA
        190        200        210        220
                                   *
        AAG AAG AAG CCA AGT ATC AAA CAG CGG GTA GTT GTG ACT GGA ATG
        Lys Lys Lys Pro Ser Ile Lys Gln Arg Val Val Val Thr Gly Met>
        230        240        250        260        270
                    *
        GGT GTG GTG ACT CCT CTA GGC CAT GAC CCT GAT GTT TTC TAC AAT AAT
        Gly Val Val Thr Pro Leu Gly His Asp Pro Asp Val Phe Tyr Asn Asn>
        280        290        300        310        320
                              *
        CTG CTT GAT GGA ACG AGT GGC ATA AGT GAG ATA GAG ACC TTT GAT TGT
        Leu Leu Asp Gly Thr Ser Gly Ile Ser Glu Ile Glu Thr Phe Asp Cys>
        330        340        350        360        370
                                           *
        GCT CAA TTT CCT ACG AGA ATT GCT GGA GAG ATC AAG TCT TTC TCC ACA
        Ala Gln Phe Pro Thr Arg Ile Ala Gly Glu Ile Lys Ser Phe Ser Thr>
```

FIGURE 4
1/6

```
         380            390            400            410            420
                                                                      *
GAT GGT TGG GTG GCC CCG AAG CTC TCC AAG AGG ATG GAC AAG TTC ATG
Asp Gly Trp Val Ala Pro Lys Leu Ser Lys Arg Met Asp Lys Phe Met>
         430            440            450            460
CTT TAC ATG CTG ACT GCC GGC AAG AAA GCA TTA ACA AAT GGT GGA ATC
Leu Tyr Met Leu Thr Ala Gly Lys Lys Ala Leu Thr Asn Gly Gly Ile>
470            480            490            500            510
                *
ACC GAA GAT GTG ATG AAA GAG CTA GAT AAA AGA AAA TGC GGA GTT CTC
Thr Glu Asp Val Met Lys Glu Leu Asp Lys Arg Lys Cys Gly Val Leu>
         520            530            540            550            560
                                *
ATT GGC TCA GCA ATG GGT GGA ATG AAG GTA TTC AAT GAT GCC ATT GAA
Ile Gly Ser Ala Met Gly Gly Met Lys Val Phe Asn Asp Ala Ile Glu>
         570            580            590            600            610
                                               *
GCC CTA AGG ATT TCA TAT AAG AAG ATG AAT CCC TTT TGT GTA CCT TTC
Ala Leu Arg Ile Ser Tyr Lys Lys Met Asn Pro Phe Cys Val Pro Phe>
         620            630            640            650            660
                                                                      *
GCT ACC ACA AAT ATG GGA TCA GCT ATG CTT GCA ATG GAC TTG GGA TGG
Ala Thr Thr Asn Met Gly Ser Ala Met Leu Ala Met Asp Leu Gly Trp>
         670            680            690            700
ATG GGC CCC AAC TAC TCG ATA TCT ACT GCT TGT GCA ACG AGT AAC TTT
Met Gly Pro Asn Tyr Ser Ile Ser Thr Ala Cys Ala Thr Ser Asn Phe>
```

FIGURE 4
2/6

```
710         720         730         740         750
            *
      TGT ATC CTG AAT GCT GCG AAC CAC ATA ATC AGA GGC GAA GCA GAT GTG
      Cys Ile Leu Asn Ala Ala Asn His Ile Ile Arg Gly Glu Ala Asp Val>
            760         770         780         790         800
                                          *
      ATG CTT TGC GGG GGC TCA GAT GCG GTA ATC ATA CCT ATT GGT ATG GGA
      Met Leu Cys Gly Gly Ser Asp Ala Val Ile Ile Pro Ile Gly Met Gly>
            810         820         830         840         850
                                                *
      GGT TTT GTT GCA TGC CGA GCT TTG TCA CAG AGA AAT GCC GAC CCT ACT
      Gly Phe Val Ala Cys Arg Ala Leu Ser Gln Arg Asn Ala Asp Pro Thr>
            860         870         880         890         900
                                                            *
      AAA GCT TCA AGA CCA TGG GAC AGT AAT CGT GAT GGA TTT GTT ATG GGG
      Lys Ala Ser Arg Pro Trp Asp Ser Asn Arg Asp Gly Phe Val Met Gly>
            910         920         930         940
      GAA GGA GCT GGA GTG CTA CTA CTA GAG GAG TTA GAG CAT GCA AAG AAA
      Glu Gly Ala Gly Val Leu Leu Leu Glu Glu Leu Glu His Ala Lys Lys>
      950         960         970         980         990
                  *
      AGA GGT GCG ACT ATT TAC GCA GAA TTT CTA GGT GGA AGT TTC ACT TGC
      Arg Gly Ala Thr Ile Tyr Ala Glu Phe Leu Gly Gly Ser Phe Thr Cys>
      1000        1010        1020        1030        1040
                              *
      GAT GCC TAC CAC ATG ACC GAG CCT CAC CCT GAT GGA GCT GGA GTG ATT
      Asp Ala Tyr His Met Thr Glu Pro His Pro Asp Gly Ala Gly Val Ile>
```

FIGURE 4
3/6

```
1050                1060                1070                1080                1090
CTC TGC ATA GAG AAG GCT TTG GCT CAG TCA GGA GTC TCT AGG GAA GAC
Leu Cys Ile Glu Lys Ala Leu Ala Gln Ser Gly Val Ser Arg Glu Asp>
          1100                1110                1120                1130                1140

GTA AAT TAC ATA AAT GCA CAT GCC ACA TCC ACT CCA GCT GGA GAT ATC
Val Asn Tyr Ile Asn Ala His Ala Thr Ser Thr Pro Ala Gly Asp Ile>
          1150                1160                1170                1180

AAA GAG TAC CAA GCT CTT ATC CAC TGT TTC GGC CAA AAC AAC GAG TTA
Lys Glu Tyr Gln Ala Leu Ile His Cys Phe Gly Gln Asn Asn Glu Leu>
1190                1200                1210                1220                1230

AAA GTG AAT TCT ACC AAA TCA ATG ATT GGT CAC CTT CTC GGA GCA GCC
Lys Val Asn Ser Thr Lys Ser Met Ile Gly His Leu Leu Gly Ala Ala>
          1240                1250                1260                1270                1280

GGT GGT GTG GAA GCA GTT TCA GTA GTT CAG GCA ATA AGG ACT GGG TGG
Gly Gly Val Glu Ala Val Ser Val Val Gln Ala Ile Arg Thr Gly Trp>
          1290                1300                1310                1320                1330

ATC CAT CCG AAT ATT AAT TTG GAA AAC CCA GAT GAA GGC GTG GAT ACC
Ile His Pro Asn Ile Asn Leu Glu Asn Pro Asp Glu Gly Val Asp Thr>
          1340                1350                1360                1370                1380

AAA TTG CTC GTG GGC CCT AAG AAG GAG AGA CTG AAC ATT AAG GTC GGT
Lys Leu Leu Val Gly Pro Lys Lys Glu Arg Leu Asn Ile Lys Val Gly>
```

FIGURE 4
4/6

```
      1390       1400       1410       1420
TTG TCT AAT TCA TTC GGG TTT GGT GGG CAC AAC TCG TCC ATA CTC TTC
Leu Ser Asn Ser Phe Gly Phe Gly Gly His Asn Ser Ser Ile Leu Phe>

1430       1440       1450       1460       1470       1480
         *
GCC CCT TAC AAC TAG GGCGTTT CATGTGTGGA ATTCTACTCA ATCTATCAAA
Ala Pro Tyr Asn ***>

1490       1500       1510       1520       1530       1540
            *
GCTGAAGTTT TGAGGACTCC AGCATGTTGG TAGCTCCTTA CGTCTCTAGA CATGCCCATG 1550       1560       1570       1580       1590       1600
            *
AGTTTTGTGT CGGGAGCTGT AGTCGGAACC ATGACGGATT GAGTACTCAT GGCGACACAG 1610       1620       1630       1640       1650       1660
            *
GATATACTCC TTGCTAGAAT TGTTAGAGCA CTATTCATTA TCCCATTTTT TTTCTGAAAT 1670       1680       1690       1700       1710       1720
            *
CTCCCCTCCTT ACGGTAGTTG TACTTTCGAG CGTTTCATCG AGTCAGTGAA GAAGAGAACA 1730       1740       1750       1760       1770       1780
            *
AAGCTAACTC GGGCACGTAG TAACCATTTG CCCTTTGTTT TGCTCTCTAT TTTATCGCCG 1790       1800       1810       1820       1830       1840
            *
TTTTGTGGGT TAAAATTGT AAAACTAGAC GACTGGTTTG TTTTCTCTTG ATCATTGGAG
```

FIGURE 4
5/6

```
          1850       1860       1870       1880       1890       1900
                      *
ATGTATGGCC ATATTTGCCT TTCATTGATG ATAAAAAAAA AAAAAAAAA AAAAAAAAA
           1910       1920
            *
AAAAAAAAA AAAAAAAAA A
```

FIGURE 4
6/6

```
CTGGTACGCC TGCAGGTACC GGTCCGGAAT TCCCGGGTCG ACCCACGCGT CCGTCTTCCC    60

ACTCCGATCG TTCTTCTTCC ACCGCATCTC TTCTCTTCTC TTGGCTTCTC CGCCATCCTC   120

CGCCGCC ATG CAT TCC CTC CAG TCA CCC TCC CTT CGG GCC TCC CCG CTC    169
        Met His Ser Leu Gln Ser Pro Ser Leu Arg Ala Ser Pro Leu
        1               5                   10

GAC CCC TTC CGC CCC AAA TCA TCC ACC GTC CGC CCC CTC CAC CGA GCA    217
Asp Pro Phe Arg Pro Lys Ser Ser Thr Val Arg Pro Leu His Arg Ala
15                  20                  25                  30

TCA ATT CCC AAC GTC CGG GCC GCT TCC CCC ACC GTC TCC GCT CCC AAG    265
Ser Ile Pro Asn Val Arg Ala Ala Ser Pro Thr Val Ser Ala Pro Lys
        35                  40                  45

CGC GAG ACC GAC CCC AAG AAG CGC GTC GTG ATC ACC GGA ATG GGC CTT    313
Arg Glu Thr Asp Pro Lys Lys Arg Val Val Ile Thr Gly Met Gly Leu
50                  55                  60

GTC TCC GTT TTC GGC TCC GAC GTC GAT GCG TAC TAC GAC AAG CTC CTG    361
Val Ser Val Phe Gly Ser Asp Val Asp Ala Tyr Tyr Asp Lys Leu Leu
65                  70                  75

TCA GGA GAG AGC GGG ATC GGC CCA ATC GAC CGC TTC GAC GCC TCC AAG    409
Ser Gly Glu Ser Gly Ile Gly Pro Ile Asp Arg Phe Asp Ala Ser Lys
80                  85                  90

TTC CCC ACC AGG TTC GGC GGC CAG ATT CGT GGC TTC AAC TCC ATG GGA    457
Phe Pro Thr Arg Phe Gly Gly Gln Ile Arg Gly Phe Asn Ser Met Gly
95                  100                 105                 110

TAC ATT GAC GGC AAA AAC GAC AGG CGG CTT GAT GAT TGC CTT CGC TAC    505
Tyr Ile Asp Gly Lys Asn Asp Arg Arg Leu Asp Asp Cys Leu Arg Tyr
        115                 120                 125
```

FIGURE 5
1/4

```
TGC ATT GTC GCC GGG AAG AAG TCT CTT GAG GAC GCC GAT CTC GGT GCC    553
Cys Ile Val Ala Gly Lys Lys Ser Leu Glu Asp Ala Asp Leu Gly Ala
            130                 135                 140

GAC CGC CTC TCC AAG ATC GAC AAG AGA GCC GGA GTG CTG GTT GGG        601
Asp Arg Leu Ser Lys Ile Asp Lys Arg Ala Gly Val Leu Val Gly
            145                 150                 155

ACA GGA ATG GGT GGT CTG ACT GTC TTC TCT GAC GGG GTT CAA TCT CTT    649
Thr Gly Met Gly Gly Leu Thr Val Phe Ser Asp Gly Val Gln Ser Leu
            160                 165                 170

ATC GAG AAG GGT CAC CGG AAA ATC ACC CCT TTC TTC ATC CCC TAT GCC    697
Ile Glu Lys Gly His Arg Lys Ile Thr Pro Phe Phe Ile Pro Tyr Ala
            175                 180                 185                 190

ATT ACA AAC ATG GGG TCT GCC CTG CTC GCT ATT GAA CTC GGT CTG ATG    745
Ile Thr Asn Met Gly Ser Ala Leu Leu Ala Ile Glu Leu Gly Leu Met
            195                 200                 205

GGC CCA AAC TAT TCA ATT TCC ACT GCA TGT GCC ACT TCC AAC TAC TGC    793
Gly Pro Asn Tyr Ser Ile Ser Thr Ala Cys Ala Thr Ser Asn Tyr Cys
            210                 215                 220

TTC CAT GCT GCT GCT AAT CAT ATC ATT CGC CGT GGT GAG GCT GAT CTT ATG    841
Phe His Ala Ala Ala Asn His Ile Ile Arg Arg Gly Glu Ala Asp Leu Met
            225                 230                 235

ATT GCT GGA GGC ACT GAG GCC GCA ATC ATT CCA ATT GGG TTG GGA GGC    889
Ile Ala Gly Gly Thr Glu Ala Ala Ile Ile Pro Ile Gly Leu Gly Gly
            240                 245                 250
```

FIGURE 5
2/4

```
TTT GTG GCT TGC AGG GCT CTG TCT CAA AGG AAC GAT GAC CCT CAG ACT      937
Phe Val Ala Cys Arg Ala Leu Ser Gln Arg Asn Asp Asp Pro Gln Thr
255                 260                 265                 270

GCC TCT AGG CCC TGG GAT AAA GAC CGT GAT GGT TTT GTG ATG GGT GAA      985
Ala Ser Arg Pro Trp Asp Lys Asp Arg Asp Gly Phe Val Met Gly Glu
        275                 280                 285

GGT GCT GGA GTG TTG GTG CTG GAG AGC TTG GAA CAT GCA ATG AAA CGA     1033
Gly Ala Gly Val Leu Val Leu Glu Ser Leu Glu His Ala Met Lys Arg
290                 295                 300

GGA GCA CCT ATT ATT GCA GAG TAT TTG GGA GGT GCA ATC AAC TGT GAT     1081
Gly Ala Pro Ile Ile Ala Glu Tyr Leu Gly Gly Ala Ile Asn Cys Asp
305                 310                 315

GCT TAT CAC ATG ACT GAC CCA AGG GCT GAT GGT CTC GGT GTC TCC TCT     1129
Ala Tyr His Met Thr Asp Pro Arg Ala Asp Gly Leu Gly Val Ser Ser
320                 325                 330

TGC ATT GAG AGT AGC CTT GAA GAT GCT GGC GTC TCA CCT GAA GAG GTC     1176
Cys Ile Glu Ser Ser Leu Glu Asp Ala Gly Val Ser Pro Glu Glu Val
335                 340                 345                 350

AAT TAC ATA AAT GCT CAT CAT GCG ACT TCT ACT CTA GCT GGG GAT CTC GCC 1224
Asn Tyr Ile Asn Ala His Ala Thr Ser Thr Leu Ala Gly Asp Leu Ala
        355                 360                 365

GAG ATA AAT GCC ATC AAG AAG GTT TTC AAG AAC ACA AAG GAT ATC AAA     1272
Glu Ile Asn Ala Ile Lys Lys Val Phe Lys Asn Thr Lys Asp Ile Lys
370                 375                 380
```

FIGURE 5
3/4

```
ATT AAT GCA ACT AAG TCA ATG ATC GGA CAC TGT CTT GGA GCC TCT GGA    1320
Ile Asn Ala Thr Lys Ser Met Ile Gly His Cys Leu Gly Ala Ser Gly
            385                 390                 395

GGT CTT GAA GCT ATA GCG ACT ATT AAG GGA ATA AAC ACC GGC TGG CTT    1368
Gly Leu Glu Ala Ile Ala Thr Ile Lys Gly Ile Asn Thr Gly Trp Leu
400                 405                 410

CAT CCC AGC ATT AAT CAA TTC AAT CCT GAG CCA TCC GTG GAG TTC GAC    1416
His Pro Ser Ile Asn Gln Phe Asn Pro Glu Pro Ser Val Glu Phe Asp
                415                 420                 425   430

ACT GTT GCC AAC AAG CAG CAA CAC GAA GTT AAT GTT GCG ATC TCG        1464
Thr Val Ala Asn Lys Gln Gln His Glu Val Asn Val Ala Ile Ser
                435                 440                 445

AAT TCA TTT GGA TTC GGA GGC CAC AAC TCA GTC GTG GCT TTC TCG GCT    1512
Asn Ser Phe Gly Phe Gly Gly His Asn Ser Val Val Ala Phe Ser Ala
                    450                 455                 460

TTC AAG CCA TGA TTACC CATTTCACAA GGCACTTGTC ATTGAGAGTA CGGTTGTTCG  1569
Phe Lys Pro
        465

TCAAACCCAT TTAGGATACT GTTCTATGTA AAAAAAGTA AGGATTATCA CTTTCCCTTC   1629

TAATCCTGTC TCCAGTTTGA GAATGAAATT ATATTTATTT TAAAAAAAA AAAAAGGGC    1689

GGCCGCTCTA GAGGATCCAA GCT                                          1712
```

FIGURE 5
4/4

Sequence Range: 1 to 1802

```
        10          20          30          40          50          60
                                                                      *
                GGTCGACCCA CGGGTCCGGG CTTTCCGACC ACATTTCATT TCTTGCCTCG TTATCTCCGC 70          80          90         100         110
CGCTCCTCCG CCGTCGTTCG CGGCCGCCGC C ATG CAA TCC CTC CAC TCC CCT TCC
                                  Met Gln Ser Leu His Ser Pro Ser 120         130         140         150         160
    *
CTC CGC CCC CCT CTC GAG CCC TTC CGC CTC AAT TCC CCC TCC TCC
Leu Arg Pro Ser Leu Glu Pro Phe Arg Leu Asn Ser Pro Ser Ser 170         180         190         200         210
                *
GCC GCT CTC CGC CCC CTC CGT CGC GCC AGC CTC CCC GTC ATC CGT
Ala Ala Leu Arg Pro Leu Arg Arg Ala Ser Leu Pro Val Ile Arg 220         230         240         250
                            *
GCT GCC ACC GCC TCC GCC CCC AAG CGC GAG TCC GAC CCC AAG AAG CGG
Ala Ala Thr Ala Ser Ala Pro Lys Arg Glu Ser Asp Pro Lys Lys Arg 260         270         280         290         300
                                                        *
GTC GTC ATC ACC GGC ATG CTC GGC CTC GTC TCC TTC GGC AGC GAC GTC
Val Val Ile Thr Gly Met Leu Gly Leu Val Ser Val Phe Gly Ser Asp Val 310         320         330         340         350
GAC GCC TAC TAC GAC AAG CTG CTC TCC GGC GAG AGC GGC ATC AGC CTA
Asp Ala Tyr Tyr Asp Lys Leu Leu Ser Gly Glu Ser Gly Ile Ser Leu
```

FIGURE 6
1/5

```
360         370         380         390         400
 *
ATC GAC CGC TTC GAC GCT TCC AAA TTC CCC ACC AGG TTC GCC GGC CAG
Ile Asp Arg Phe Asp Ala Ser Lys Phe Pro Thr Arg Phe Ala Gly Gln
        410         420         430         440         450
                     *
ATC CGT GGC TTC AAC GCG ACG GGC TAC ATC GAC GGC AAG AAC GAC CGG
Ile Arg Gly Phe Asn Ala Thr Gly Tyr Ile Asp Gly Lys Asn Asp Arg
        460         470         480         490
                                  *
CGG CTC GAC GAT TGC CTC CGC TAC TGC ATT GTC GCC GGC AAG AAG GCT
Arg Leu Asp Asp Cys Leu Arg Tyr Cys Ile Val Ala Gly Lys Lys Ala
500         510         520         530         540
                                                    *
CTC GAA GAC GCC GAT CTC GCC GGC CAA TCC CTC TCC AAG ATT GAT AAG
Leu Glu Asp Ala Asp Leu Ala Gly Gln Ser Leu Ser Lys Ile Asp Lys
        550         560         570         580         590
GAG AGG GCC GGA GTG CTA GTT GGA ACC GGT GGC ATG GGT CTA ACT GTC
Glu Arg Ala Gly Val Leu Val Gly Thr Gly Gly Met Gly Leu Thr Val
600         610         620         630         640
 *
TTC TCT GAC GGG GTT CAG AAT CTC ATC GAG AAA GGT CAC CGG AAG ATC
Phe Ser Asp Gly Val Gln Asn Leu Ile Glu Lys Gly His Arg Lys Ile
        650         660         670         680         690
                     *
TCC CCG TTT TTC ATT CCA TAT GCC ATT ACA AAC ATG GGG TCT GCG CTG
Ser Pro Phe Phe Ile Pro Tyr Ala Ile Thr Asn Met Gly Ser Ala Leu
```

FIGURE 6
2/5

```
700                710              720              730
CTT GCC ATC GAT TTG GGT CTG ATG GGC CCA AAC TAT TCG ATT TCA ACT
Leu Ala Ile Asp Leu Gly Leu Met Gly Pro Asn Tyr Ser Ile Ser Thr
740              750              760              770              780
                                                                    *
GCA TGT GCT ACT TCC AAC TAC TGC TTT TAT GCT GCC GCC AAT CAT ATC
Ala Cys Ala Thr Ser Asn Tyr Cys Phe Tyr Ala Ala Ala Asn His Ile
790              800              810              820              830
CGC CGA GGT GAG GCT GAC CTG ATG ATT GCT GGA GGA ACT GAG GCT GCG
Arg Arg Gly Glu Ala Asp Leu Met Ile Ala Gly Gly Thr Glu Ala Ala
840              850              860              870              880
 *
GTC ATT CCA ATT GGT TTA GGA GGA TTC GTT GCC TGC AGG GCT TTA TCT
Val Ile Pro Ile Gly Leu Gly Gly Phe Val Ala Cys Arg Ala Leu Ser
890              900              910              920              930
                  *
CAA AGG AAT GAT GAT CCT CAG ACT GCC TCA AGG CCG TGG GAT AAG GAC
Gln Arg Asn Asp Asp Pro Gln Thr Ala Ser Arg Pro Trp Asp Lys Asp
940              950              960              970
                                   *
CGT GAT GGC TTT GTG ATG GGT GAA GGG GCT GGA GTA TTG GTT ATG GAG
Arg Asp Gly Phe Val Met Gly Glu Gly Ala Gly Val Leu Val Met Glu
980              990              1000             1010             1020
                                                                    *
AGC TTG GAG CAT GCA ATG AAA CGG GGA GCG CCG ATT ATT GCA GAA TAT
Ser Leu Glu His Ala Met Lys Arg Gly Ala Pro Ile Ile Ala Glu Tyr
```

FIGURE 6
3/5

```
1030                1040                1050                1060                1070
TTG GGA GGT GCA GTC AAC TGT GAT GCT TAT CAT ATG ACT GAT CCA AGG
Leu Gly Gly Ala Val Asn Cys Asp Ala Tyr His Met Thr Asp Pro Arg
      1080                1090                1100                1110                1120
       *
GCT GAT GGG CTT GGT GTC TCC TCG ATT GAG AGC AGT CTC GAA GAT
Ala Asp Gly Leu Gly Val Ser Ser Cys Ile Glu Ser Ser Leu Glu Asp
      1130                1140                1150                1160                1170
                          *
GCC GGG GTC TCA CCT GAA GAG GTC GAT TAC ATA AAT GCT CAT GCG ACT
Ala Gly Val Ser Pro Glu Glu Val Asp Tyr Ile Asn Ala His Ala Thr
      1180                1190                1200                1210
                                              *
TCT ACT CTT GCT GGG GAT CTT GCC GAG ATA AAT GCC ATT AAG AAA GTT
Ser Thr Leu Ala Gly Asp Leu Ala Glu Ile Asn Ala Ile Lys Lys Val
      1220                1230                1240                1250                1260
                                                                  *
TTC AAG AAC ACC AAG GAA ATC AAA ATC AAT GCA ACT AAG TCA ATG ATC
Phe Lys Asn Thr Lys Glu Ile Lys Ile Asn Ala Thr Lys Ser Met Ile
      1270                1280                1290                1300                1310
GGA CAC TGT CTT GGA GCA TCA GGA GGT CTT GAA GCC ATC GCA ACC ATT
Gly His Cys Leu Gly Ala Ser Gly Gly Leu Glu Ala Ile Ala Thr Ile
      1320                1330                1340                1350                1360
       *
AAG GGA ATA ACC ACC GGC TGG CTT CAT CCC AGC ATT AAT CAA TTT AAT
Lys Gly Ile Thr Thr Gly Trp Leu His Pro Ser Ile Asn Gln Phe Asn
```

FIGURE 6
4/5

```
                                                  1370      1380      1390      1400      1410
                                                   CCC GAG CCA TCG GTG GAC TTC AAC ACT GTT GCC AAC AAA AAG CAG CAA
                                                   Pro Glu Pro Ser Val Asp Phe Asn Thr Val Ala Asn Lys Lys Gln Gln
                                                            *
             1420      1430      1440      1450
CAT GAA GTG AAC GTC GCT ATC TCG AAT TCT TTT GGA TTT GGA GGG CAC
His Glu Val Asn Val Ala Ile Ser Asn Ser Phe Gly Phe Gly Gly His
                              *
1460      1470      1480      1490      1500      1510
AAC TCG GTT GTG GCA TTC TCA GCT TTC AAG CCA TGA ATTCT ACTTGGTTCA
Asn Ser Val Val Ala Phe Ser Ala Phe Lys Pro ***
         1520      1530      1540      1550      1560      1570
AAATGCACAC CAGTTGCTGA GATAGGGCTT CAACTTGCAG AGCAATTTTT TAAATGCCTT
                                                      *
         1580      1590      1600      1610      1620      1630
GTCGGAAGAG CGTAATACCG GAATAGGTCG GTCCTTTGAT AGTTCCTCGA AGCCATTTAG
                                                      *                *
         1640      1650      1660      1670      1680      1690
GATGATGTTT TACTGTAATA ATCGAAGATG ATTCCCATTT TAAATCTAGT CTCTGATTTA
                                                      *                *
         1700      1710      1720      1730      1740      1750
TGTATTAGAA AGACCAATGA AAGATTTTGT GTCATGTTTG TGTTGTCAAT GTTATTTAAG
                                                      *                *
         1760      1770      1780      1790      1800
ATAAAGCAAA AAAAAAAAA AAGGGCGGCC GCTCTAGAGG ATCCAGCTTA CT
                                                      *
```

FIGURE 6
5/5

Sequence Range: 1 to 2369

```
                    10         20         30         40         50         60
                                                                             *
            GTACGCCTGC AGGTACCGGT CCGGAATTCC CGGGTCGACC CACGCGTCCG CATAAAGAG 70         80         90        100        110        120
                                                                             *
            AGAGAGAGGG ATCCATGAA TGCGGCCACC CTCCTTTCAT CTTCGATTCA TTACCATACC 130        140        150        160        170        180
                                                                             *
            ATTCCGCTGA TCCATTTTCC GCCTTTTCCG GGTCTTTCAT CCCAAAGGGT ATCCTTTCT 190        200        210        220        230

ATCCTATCTT CTCAAAGGGT CAGTCAGTTC CCTCCA ATG CCT GCC GCC TCT TCC
                                                    Met Pro Ala Ala Ser Ser>

240               250             260             270             280
                 *
            CTG CTC GCT TCC CCT CTC TGT ACG TGG CTC CTT GCC GCC TGC ATG TCT
            Leu Leu Ala Ser Pro Leu Cys Thr Trp Leu Leu Ala Ala Cys Met Ser>

290             300             310             320             330
                                 *
            ACC TTC CAC CCC TCC GAC CCT CTT CCG CCT TCC ATC TCC TCT CCT
            Thr Ser Phe His Pro Ser Asp Pro Leu Pro Pro Ser Ile Ser Ser Pro>

340             350             360             370
                                                 *
            CGC CGA CGC CTC TCC CGC CGC CGG ATT CTC TCC CAA TGC GCC CCA CTA
            Arg Arg Arg Leu Ser Arg Arg Arg Ile Leu Ser Gln Cys Ala Pro Leu>
```

FIGURE 7
1/7

```
380         390         400         410         420
CCT TCT GCT TCC TCC GCC CTC CGC GGA TCC AGT TTC CAT ACC CTC GTC
Pro Ser Ala Ser Ser Ala Leu Arg Gly Ser Ser Phe His Thr Leu Val>

430         440         450         460         470
ACC TCT TAC CTC GCC TGC TTC GAG CCC TGC CAT GAC TAC TAT ACA TCC
Thr Ser Tyr Leu Ala Cys Phe Glu Pro Cys His Asp Tyr Tyr Thr Ser>

480         490         500         510         520
GCA TCC TTG TTC GGA TCC AGA CCC ATT CGC ACC CGC AGG CAC CGG
Ala Ser Leu Phe Gly Ser Arg Pro Ile Arg Thr Arg Arg His Arg>

530         540         550         560         570
AGG CTC AAT CGA GCT TCC CCT TCC AGG GAG GCA ATG GCC GTG GCT CTG
Arg Leu Asn Arg Ala Ser Pro Ser Arg Glu Ala Met Ala Val Ala Leu>

580         590         600         610
CAA CCT GAA CAG GAA GTT ACC ACA AAG AAG CCA AAG AGT ATC AAA CAG
Gln Pro Glu Gln Glu Val Thr Thr Lys Lys Pro Lys Ser Ile Lys Gln>

620         630         640         650         660
CGG CGA GTA GTT GTG ACT GGA ATG GGT GTG GTG ACT CCT CTA GGC CAT
Arg Arg Val Val Val Thr Gly Met Gly Val Val Thr Pro Leu Gly His>

670         680         690         700         710
GAC CCT GAT GTT TTC TAC AAT CTG CTT GAT GGA ACG AGT GGC ATA
Asp Pro Asp Val Phe Tyr Asn Leu Leu Asp Gly Thr Ser Gly Ile>
```

FIGURE 7
2/7

```
        720                 730                 740                 750                 760
         *
AGC GAG ATA GAG ACC TTT GAT TGT GCT CAA TTT CCT ACG AGA ATT GCT
Ser Glu Ile Glu Thr Phe Asp Cys Ala Gln Phe Pro Thr Arg Ile Ala>

770                 780                 790                 800                 810
                             *
GGA GAG ATC AAG TCT TTC TCC ACA GAT GGT TGG GTG GCC CCG AAG CTC
Gly Glu Ile Lys Ser Phe Ser Thr Asp Gly Trp Val Ala Pro Lys Leu>

820                 830                 840                 850
                                                 *
TCT AAG AGG ATG GAC ATG TTC ATG CTA TAC TTG ACC GCT GGC AAG
Ser Lys Arg Met Asp Met Phe Met Leu Tyr Met Leu Thr Ala Gly Lys>

860                 870                 880                 890                 900
                                                                     *
AAA GCA TTA ACA GAT GGT GGA ATC ACC GAA GAT GTG ATG AAA GAG CTA
Lys Ala Leu Thr Asp Gly Gly Ile Thr Glu Asp Val Met Lys Glu Leu>

910                 920                 930                 940                 950
GAT AAA AGA AAA TGC GGA GTT CTC ATT GGC TCA GCA ATG GGT GGA ATG
Asp Lys Arg Lys Cys Gly Val Leu Ile Gly Ser Ala Met Gly Gly Met>

960                 970                 980                 990                 1000
         *                                                                                *
AAG GTA TTC AAT GAT GCC ATT GAA GCC CTA AGG ATT TCA TAT AAG AAG
Lys Val Phe Asn Asp Ala Ile Glu Ala Leu Arg Ile Ser Tyr Lys Lys>

1010                1020                1030                1040                1050
                             *
ATG AAT CCC TTT TGT GTA CCT TTC GCT ACC ACA AAT ATG GGA TCA GCT
Met Asn Pro Phe Cys Val Pro Phe Ala Thr Thr Asn Met Gly Ser Ala>
```

FIGURE 7
3/7

```
ATG CTT GCA ATG GAC TTG GGA TGG ATG GGG CCC AAC TAC TCG ATA TCT
Met Leu Ala Met Asp Leu Gly Trp Met Gly Pro Asn Tyr Ser Ile Ser>
1100      1110      1120      1130      1140
                                             *
ACT GCT TGT GCA ACG AGT AAC TTT TGT ATA ATG AAT GCT GCG AAC CAT
Thr Ala Cys Ala Thr Ser Asn Phe Cys Ile Met Asn Ala Ala Asn His>
     1150      1160      1170      1180      1190
ATA ATC AGA GGC GAA GCA GAT GTG ATG CTT TGC GGG GGC TCA GAT GCG
Ile Ile Arg Gly Glu Ala Asp Val Met Leu Cys Gly Gly Ser Asp Ala>
1200      1210      1220      1230      1240
    *
GTA ATC ATA CCT ATT GGT ATG GGA GGT TTT GTT GCA TGC CGA GCT TTG
Val Ile Ile Pro Ile Gly Met Gly Gly Phe Val Ala Cys Arg Ala Leu>
     1250      1260      1270      1280      1290
                *
TCC CAG AGA AAT TCC GAC CCT ACT AAA GCT TCA AGA CCA TGG GAC AGT
Ser Gln Arg Asn Ser Asp Pro Thr Lys Ala Ser Arg Pro Trp Asp Ser>
1300      1310      1320      1330
                         *
AAT CGT GAT GGA TTT GTT ATG GGG GAA GCT GGA GTG CTA CTA CTA
Asn Arg Asp Gly Phe Val Met Gly Glu Ala Gly Val Leu Leu Leu>
     1340      1350      1360      1370      1380
                                                    *
GAG GAG TTG GAG CAT GCA AAG AAA AGA GGT GCG ACT ATT TAC GCA GAA
Glu Glu Leu Glu His Ala Lys Lys Arg Gly Ala Thr Ile Tyr Ala Glu>
```

FIGURE 7
4/7

```
        1390            1400            1410            1420            1430
TTT CTA GGT GGG AGT TTC ACT TTC GAT GCC TAC CAC ATG ACC GAG CCT
Phe Leu Gly Gly Ser Phe Thr Phe Asp Ala Tyr His Met Thr Glu Pro>
        1440            1450            1460            1470            1480
                 *
CAC CCT GAT GGA GCT GGA GTG ATT CTC TGC ATA GAG AAG GCT TTG GCT
His Pro Asp Gly Ala Gly Val Ile Leu Cys Ile Glu Lys Ala Leu Ala>
        1490            1500            1510            1520            1530
                 *
CAG TCA GGA GTC TCT AGG GAA GAC GTA AAT TAC ATA AAT GCC CAT GCC
Gln Ser Gly Val Ser Arg Glu Asp Val Asn Tyr Ile Asn Ala His Ala>
        1540            1550            1560            1570
                                   *
ACA TCC ACT CCG GCT GGA GAT ATC AAA GAG TAC CAA GCT CTT ATC CAC
Thr Ser Thr Pro Ala Gly Asp Ile Lys Glu Tyr Gln Ala Leu Ile His>
        1580            1590            1600            1610            1620
                                                              *
TGT TTC GGC CAA AAC AGA GAG TTA AAA GTT AAT TCA ACC AAA TCA ATG
Cys Phe Gly Gln Asn Arg Glu Leu Lys Val Asn Ser Thr Lys Ser Met>
        1630            1640            1650            1660            1670
ATT GGT CAC CTT CTC GGA GCA GCC GGT GGT GTG GAA GCA GTT TCA GTA
Ile Gly His Leu Leu Gly Ala Ala Gly Gly Val Glu Ala Val Ser Val>
        1680            1690            1700            1710            1720
         *
GTT CAG GCA ATA AGG ACT GGG TGG ATC CAT CCG AAT ATT AAT TTG GAA
Val Gln Ala Ile Arg Thr Gly Trp Ile His Pro Asn Ile Asn Leu Glu>
```

FIGURE 7
5/7

```
                        1730        1740        1750        1760        1770
AAC CCA GAT GAA GGC GTG GAT ACA AAA TTG CTC GTG GGT CCT AAG AAG
Asn Pro Asp Glu Gly Val Asp Thr Lys Leu Leu Val Gly Pro Lys Lys>
                1780        1790        1800        1810
GAG AGA CTG AAC GTT AAG GTC GGT TTG TCT AAT TCA TTT GGG TTT GGT
Glu Arg Leu Asn Val Lys Val Gly Leu Ser Asn Ser Phe Gly Phe Gly>
  1820        1830        1840        1850        1860        1870
GGG CAC AAC TCG TCC ATA CTC TTC GCC CCT TAC ATC TAG GAC GTTCCGTGT
Gly His Asn Ser Ser Ile Leu Phe Ala Pro Tyr Ile ***>
GTGGAATTCT ACTCAACATA TCAAAGCTGA AGTTTTGAGG ACTCCAGCAT GTTGGTAGCT
     1880        1890        1900        1910        1920        1930
CCTTACGTCT CTAGACATGC CCATGAGTTT TGTGTCCGGA GCTTTAGTCG GAACCATGAC
     1940        1950        1960        1970        1980        1990
GGATTGAGTA CTCATGGCGA CACTTGATAT ACTCCTTGCT AGAATTGTTG GTAGAGCAAT
     2000        2010        2020        2030        2040        2050
ATTCATTATC TCATATTTTT TTTTTCTCTG AAATCCCCT CCTTGCAATA GTTGTACTTT
     2060        2070        2080        2090        2100        2110
CGAGCTTTTC ATCGAGTCAG TGAAGAAGAG AACAAAGCTG TTAACTCGGG CACGTAGTAA
     2120        2130        2140        2150        2160        2170
```

FIGURE 7
6/7

```
         2180       2190       2200       2210       2220       2230
CCATTTGCCC TTTGTTTTGC TCTCTATTTC ATCACCGTTT TGTGGTTTTA AAATTTGTAA
                                                    *
         2240       2250       2260       2270       2280       2290
AACTAGAAGA CTGGTTTAGA TTGGTTGTT TTCTCATTGA TAATTGGGGR ATGTATGTTT
                                                    *
         2300       2310       2320       2330       2340       2350
TGGAAATAAA AAAAAAAAAA AAAAAAAAA AAAAAAAAAA AAAAAAAAA AAAAAAAAAA
                                                    *
         2360
AGGGCGGCCG CTCTAGAGG
```

FIGURE 7
7/7

Sequence Range: 1 to 2374

```
                 10         20         30         40         50         60
                                                                          *
     -A-CNTGGTC CGGAATTCCC GGGTCGACCC ACGGGTCCGC GACGCCAACC CACACCAAAC
                 70         80         90        100        110        120
                                                                          *
     TTCCTCAGCT TCTCTTTCTCA AGACGGACGC CATTGGCAGC AGACAGACAG ACAGACAGAC
                130        140        150        160        170        180
                                                                          *
     CCATAAAAGA GAGAGAGAGG GATCCATCGA ATGCGGGCCAC CCTCCTTTCA TCTTCGATTC
                190        200        210        220        230        240
                                                                          *
     ATTACCATAC CATTCCGCTG ATCCATTTC CGCCTTTTCC GGGTCTTTCA TCCCAAAGGG
                250        260        270        280        290        300
                                                                          *
     TATCCTTTTC TATCCTATCT TCTCAAAGGG TCAGTCAGTT CCCTCCAATG CCTGCCGCCT
                310        320        330        340        350        360
                                                                          *
     CTTCCCTGCT CGCTTCCCCT CTCTGTACGT GGCTCCTTGC CGCCTGCATG TCTACCTCCT
                370        380        390        400        410        420
                                                                          *
     TCCACCCCTC CGACCCTCTT CGGGCCTTCCA TCTCCTCTCC TGCCGACGC CTCTCCCGCC
                430        440        450        460        470        480
                                                                          *
     GCCGGATCT CTCCCAATGC GCCCCACTAC CTTCTGCTTC CTCCGCCCTC CGGGGATCCA
```

FIGURE 8
1/5

```
        490        500        510        520        530        540
                                                                  *
GTTCCATAC CCTCGTCACC TCTTACCTCG CCTGCTTCGA GCCCTGCCAT GACTACTATA
        550        560        570        580        590        600
                                                                  *
CATCCGCATC CTTGTTCGGA TCCAGACCCA TTCGCACCAC CGGCAGGCAC CGGAGGCTCA
        610        620        630        640        650        660
                                                                  *
ATCGAGCTTC CCCTTCCAGG GGAGGCAATG GCCGTGGCTC TGCAACCTGA ACAGGAAGTT
        670        680        690        700        710        720
                                                                  *
ACCACAAAGA AGAAGCCAAG TATCAAACAG CGGCGAGTAG TTGTGACTGG AATGGGTGTG
        730        740        750        760        770        780
                                                                  *
GTGACTCCTC TAGGCCATGA ACCTGATGTT TTTCTACAAT AATCTGCTTG ATGGAACGAG
        790        800        810        820        830        840
                                                                  *
TGGCATAAGC GAGATAGAGA CCTTTGATTG TGCTCAATTT CCTACGAGAA TTGCTGGAGA
        850        860        870        880        890        900
                                                                  *
GATCAAGTCT TTCTCCACAG ATGGTTGGGT GGCCCCGAAG CTCTCTAAGA GGATGGACAA
        910        920        930        940        950        960
                                                                  *
GTTCATGCTA TACATGCTGA CTGCTGGCAA GAAAGCATTA ACAGATGGTG GAATCACCGA
        970        980        990       1000       1010       1020
AGATGTGATG AAAGAGCTAG ATAAAAGAAA ATGCGGAGTT CTCATTGGCT CAGCAATGGG
```

FIGURE 8
2/5

```
                    1030       1040       1050       1060       1070       1080
                                                                              *
TGGAATGAAG GTATTCAATG ATGCCATTGA AGCCCTAAGG ATTTCATATA AGAAGATGAA 1090       1100       1110       1120       1130       1140
                                                                    *
TCCCTTTTGT GTACCTTTCG CTACCACAAA TATGGGATCA GCTATGCTTG CAATGGACTT 1150       1160       1170       1180       1190       1200
                                                                    *
GGGATGGATG GGGCCCAACT ACTCGATATC TACTGCTTGT GCAACGAGTA ACTTTTGTAT 1210       1220       1230       1240       1250       1260
                                                                    *
AATGAATGCT GCGAACCATA TAATCAGAGG CGAAGCAGAT GTGATGCTTT GCGGGGGCTC 1270       1280       1290       1300       1310       1320
                                                                    *
AGATGCGGTA ATCATACCTA TTGGTATGGG AGTTTTTGTT GCATGCCGAG CTTTGTCCCA 1330       1340       1350       1360       1370       1380
                                                                    *
GAGAAATTCC GACCCTACTA AAGCTTCAAG ACCATGGGAC AGTAATCGTG ATGGATTTGT 1390       1400       1410       1420       1430       1440
                                                                    *
TATGGGGAA GGAGCTGGAG TGCTACTACT AGAGGAGTTG GAGCATGCAA AGAAAAGAGG 1450       1460       1470       1480       1490       1500
                                                                    *
TGCGACTATT TACGCAGAAT TTCTAGGTGG GAGTTTCACT TGCGATGCCT ACCACATGAC
```

FIGURE 8
3/5

```
        1510       1520       1530       1540       1550       1560
   CGAGCCTCAC CCTGATGGAG CTGGAGTGAT TCTCTGCATA GAGAAGGCTT TGGCTCAGTC
        1570       1580       1590       1600       1610       1620
   AGGAGTCTCT AGGGAAGACG TAAATTACAT AAATGCCCAT GCCACATCCA CTCCGGCTGG
        1630       1640       1650       1660       1670       1680
   AGATATCAAA GAGTACCAAG CTCTTATCCA CTGTTTCGGC CAAAACAGAG AGTTAAAAGT
        1690       1700       1710       1720       1730       1740
   TAATTCAACC AAATCAATGA TTGGTCACCT TCTCGGAGCA GCCGGTGGTG TGGAAGCAGT
        1750       1760       1770       1780       1790       1800
   TTCAGTAGTT CAGGCAATAA GGACTGGGTG GATCCATCCG AATATTAATT TGGAAAACCC
        1810       1820       1830       1840       1850       1860
   AGATGAAGGC GTGGATACAA AATTGCTCGT GGGTCCTAAG AAGGAGAGAC TGAACGTTAA
        1870       1880       1890       1900       1910       1920
   GGTCGGTTTG TCTAATTCAT TTGGGTTTGG TGGGCACAAC TGTCCATAC  TCTTCGCCCC
        1930       1940       1950       1960       1970       1980
   TTACATCTAG GACGTTTCGT GTGTGGAATT CTACTCAACA TATCAAAGCT GAAGTTTTGA
        1990       2000       2010       2020       2030       2040
   GGACTCCAGC ATGTTGGTAG CTCCTTAGT  CTCTAGACAT GCCCATGAGT TTTGTGTCCG
```

FIGURE 8
4/5

```
    2050       2060       2070       2080       2090       2100
                                                                  *
GAGCTTTAGT CGGAACCATG ACGGATTGAG TACTCATGGC GACACTTGAT ATACTCCTTG 2110       2120       2130       2140       2150       2160
                                                                  *
CTAGAATTGT TGGTAGAGCA ATATTCATTA TCTCATATT TTTTTTCTC TGAAATCTCC 2170       2180       2190       2200       2210       2220
                                                                  *
CTCCTTGCAA TAGTTGTACT TTCGAGCTTT TCATCGAGTC AGTGAAGAAG AGAACAAAGC 2230       2240       2250       2260       2270       2280
                                                                  *
TGTTAACTCG GGCACGTAGT AACCATTGC CCTTGTTTT GCTCTCTATT TCATCACCGT 2290       2300       2310       2320       2330       2340
                                                                  *
TTTGTGGTTT TAAAATTTGT AAAACTAGAA GACTGGTTTA GATTGGTTTG TTTTCTCAAA 2350       2360       2370
AAAAAAAAA AAGGGGCGGCC GCTCTAGAGG ATCC
```

FIGURE 8
5/5

Sequence Range: 1 to 1580

```
              10         20         30         40         50
     CCTGAATCGG ATTCAAGAGA GAGTTTCGTT GCTGGG ATG GCA AAT GCA TCT GGG
                                            Met Ala Asn Ala Ser Gly>
          60                   70                   80                   90                  100
           *
     TTT CTG GGT TCT TCA GTT CCT GCC CTG AGA AGG GCA ACT CAG CAT TCG
     Phe Leu Gly Ser Ser Val Pro Ala Leu Arg Arg Ala Thr Gln His Ser>
              110                  120                  130                  140                  150
                                    *
     ATT TCA TCG TCT CGT GGA TCT TCC TCG GAG TTT GTC TCC AAA AGG GTG
     Ile Ser Ser Ser Arg Gly Ser Ser Ser Glu Phe Val Ser Lys Arg Val>
              160                  170                  180                  190
                                              *
     TTT TGC TGT AGT GCC GTT CAG GAT TCT GAC AGG CAG TCT TTG GGT GAT
     Phe Cys Cys Ser Ala Val Gln Asp Ser Asp Arg Gln Ser Leu Gly Asp>
     200       210                  220                  230                  240
                                                                              *
     TCT CGC TCG CCG AGG CTT GTG AGT AGA GGA TGC AAA TTA ATT GGA TCT
     Ser Arg Ser Pro Arg Leu Val Ser Arg Gly Cys Lys Leu Ile Gly Ser>
              250                  260                  270                  280                  290
     GGT TCT GCT ATA CCA GCT CTT CAA GTC TCA AAT GAT GAT CTT GCT AAA
     Gly Ser Ala Ile Pro Ala Leu Gln Val Ser Asn Asp Asp Leu Ala Lys>
              300                  310                  320                  330                  340
               *
     ATT GTC GAC ACC AAT GAT GAA TGG ATT ACT GTC CGA ACG GGG ATC CGC
     Ile Val Asp Thr Asn Asp Glu Trp Ile Thr Val Arg Thr Gly Ile Arg>
```

```
                350            360            370            380            390
AAC CGA AGG GTT CTC TCA GGT AAA GAT AGT CTT ACA AAT TTA GCA TCA
Asn Arg Arg Val Leu Ser Gly Lys Asp Ser Leu Thr Asn Leu Ala Ser>

400            410            420            430
GAG GCA GCA AGG AAA GCT CTA GAG ATG GCA CAG GTA GAC GCA AAT GAT
Glu Ala Ala Arg Lys Ala Leu Glu Met Ala Gln Val Asp Ala Asn Asp>

440            450            460            470            480
GTG GAT ATG GTT TTG ATG TGT ACT TCT ACC CCT GAG GAC CTT TTC GGC
Val Asp Met Val Leu Met Cys Thr Ser Thr Pro Glu Asp Leu Phe Gly>

490            500            510            520            530
AGT CCT CAG ATA TCG AAA GCA CTT GGC TGC AAA AAG AAT CCT TTG
Ser Ala Pro Gln Ile Ser Lys Ala Leu Gly Cys Lys Lys Asn Pro Leu>

540            550            560            570            580
TCT TAC GAC ATT ACC GCT GCA TGC AGT GGA TTT GTG TTG GGT TTA GTC
Ser Tyr Asp Ile Thr Ala Ala Cys Ser Gly Phe Val Leu Gly Leu Val>

590            600            610            620            630
TCA GCT GCT TGC CAC ATT AGA GGT GGG GGT TTT AAC AAT ATT CTA GTG
Ser Ala Ala Cys His Ile Arg Gly Gly Gly Phe Asn Asn Ile Leu Val>

640            650            660            670
ATT GGT GCT GAT TCT CTT TCT CGG TAT GTT GAC TGG ACC GAT CGG GGA
Ile Gly Ala Asp Ser Leu Ser Arg Tyr Val Asp Trp Thr Asp Arg Gly>
```

FIGURE 9
2/5

```
680
ACA TGT ATT CTC TTT GGA GAT GCT GCT GGA GCT GTA GTG GTG CAG TCA
Thr Cys Ile Leu Phe Gly Asp Ala Ala Gly Ala Val Val Val Gln Ser>
    730              740              750              770
TGT GAT GCT GAG GAA GAT GGG GAC CTC TTT GCT TTT GAT TTG CAT AGC GAT
Cys Asp Ala Glu Glu Asp Gly Asp Leu Phe Ala Phe Asp Leu His Ser Asp>
    780              790              800              810       820
GGA GAT GGG CAA AGG CAT CTA AAA GCT GCA ATC AAA GAT GAA GAT GAA GTT
Gly Asp Gly Gln Arg His Leu Lys Ala Ala Ile Lys Glu Asp Glu Val>
         830              840              850              860       870
GAT AAA GCC CTG GGA CAT AAT GGG TCC ATC AGA GAT TTT CCA CCA AGG
Asp Lys Ala Leu Gly His Asn Gly Ser Ile Arg Asp Phe Pro Pro Arg>
              880              890              900              910
CGT TCT TCA TAC TCT TGC ATC CAA ATG AAC GGT AAA GAG GTA TTC CGC
Arg Ser Ser Tyr Ser Cys Ile Gln Met Asn Gly Lys Glu Val Phe Arg>
    920              930              940              950              960
TTT GCT TGC CGC TCT GTG CCT CAG TCA ATC GAA TCA GCA CTT GGA AAG
Phe Ala Cys Arg Ser Val Pro Gln Ser Ile Glu Ser Ala Leu Gly Lys>
    970              980              990              1000             1010
GCC GGT CTT AAT GGA TCC AAC ATC GAC TGG TTG CTG CTT CAT CAG GCA
Ala Gly Leu Asn Gly Ser Asn Ile Asp Trp Leu Leu Leu His Gln Ala>

FIGURE 9
3/5
```

```
1020                1030                1040                1050                1060
  *
AAT CAG AGG ATC ATT GAT GCA GTA GCA ACA CGT CTA GAG GTT CCT CAA
Asn Gln Arg Ile Ile Asp Ala Val Ala Thr Arg Leu Glu Val Pro Gln>

1070                1080                1090                1100                1110
                             *
GAA CGA ATT ATC TCA AAC TTG GCA AAT TAC GGG AAC ACT AGT GCG GCA
Glu Arg Ile Ile Ser Asn Leu Ala Asn Tyr Gly Asn Thr Ser Ala Ala>

1120                1130                1140                1150
                                                  *
TCC ATT CCC TTG GCA CTA GAC GAA GCT GTG AGG AGT GGA AAT GTG AAG
Ser Ile Pro Leu Ala Leu Asp Glu Ala Val Arg Ser Gly Asn Val Lys>

1160                1170                1180                1190                1200
                                                                              *
CCG GGT CAC GTG ATT GCA ACC GCA GGA TTT GGC GCC GGA CTC ACA TGG
Pro Gly His Val Ile Ala Thr Ala Gly Phe Gly Ala Gly Leu Thr Trp>

1210                1220                1230                1240                1250      1260
                                                                                                    *
GGT TCT GCT ATT ATC AGG TGG GGA TAA GACTGAA GCCGAGCCAG CACTGCAGCT
Gly Ser Ala Ile Ile Arg Trp Gly ***>

1270                1280                1290                1300                1310                1320
                                                                                                                          *
TCCTCTCAAA CCGATGTTTC AGAAATTTT GCTTCCATGA CCAAAAAAG AAGAAGTCAG 1330                1340                1350                1360                1370                1380
                                                                                                                *
TCTTTTATGG AGCAAGCAAC AGACACGAT CTTCATCACA TTGCCCTTT TCGTTCCCCT
```

FIGURE 9
4/5

```
        1390       1400       1410       1420       1430       1440
                                                                  *
TTTCCATTAG TTTGATGATT TTGCTGACAA TACAATACCC ATAGTTTCTT TTGTCCCCAA
        1450       1460       1470       1480       1490       1500
                                                                  *
TAAGTTATTT GTTTCTTGTT TAATTGTTCA GCTTTTACTT CATTTTGTCT CGGGACATTG
        1510       1520       1530       1540       1550       1560
                                                                  *
GAGATGACAG CATAAACATC ATGTTTATAT TTTGCTAAAA AAAAAAAAAA AAAAAAAAAA
        1570       1580
AAAAAAAAAA AAAAAAAAAA
```

FIGURE 9
5/5

SEQUENCE LISTING

<160> NUMBER OF SEQ ID NOS: 17

<210> SEQ ID NO 1
<211> LENGTH: 1348
<212> TYPE: DNA
<213> ORGANISM: Cuphea  Hookeriana

<400> SEQUENCE: 1

```
agctccaccg cggtggcggc cgctctagaa ctagtggatc ccccgggctg caggaattcg      60
gcacgagccg atctcggtgc cgaccgcctc tccaagatcg acaaggagag agccggagtg     120
ctggtcggaa caggaatggg tggtctgact gtcttctctg acggggttca gtctcttatc     180
gagaagggtc accggaaaat caccccttc ttcatcccct atgccattac aaacatgggg     240
tctgccctgc tcgctatcga atttggtctc atgggcccaa actattcaat ttccactgca     300
tgtgccactt ccaactactg cttccatgct gccgctaatc atatccgccg tggtgaggct     360
gatcttatga ttgctggagg cactgaggcc gcaatcattc caattgggtt gggaggcttt     420
gtggcttgca gggctttgtc tcaaaggaac gatgacccgc agactgcctc taggccctgg     480
gataaagacc gtgatggttt tgtgatgggt gaaggtgctg gagtgttggt gatggagagc     540
ttggaacatg caatgagacg aggagcaccg attattgcag agtatttggg aggtgcaatc     600
aactgtgatg cttatcacat gactgatcca agggctgatg gtcttggtgt ctcttcttgc     660
attgagagta gccttgaaga tgctggcgtc tcacctgaag aggtcaatta cataaatgct     720
catgcgactt ctactctagc tggggatctc gccgagataa atgccatcaa gaaggttttc     780
aagaacacaa aggatatcaa aattaatgca actaagtcaa tgatcggaca ctgtcttgga     840
gcatctggag gtcttgaagc tatagcgact attaagggaa taaacaccgg ctggcttcat     900
cccagcatta atcaattcaa tcctgagcca tcggtggagt tcgacactgt tgccaacaag     960
aagcagcaac acgaagttaa cgttgcgatc tcgaattcat tcggatttgg aggccacaac    1020
tcagtcgtgg ctttctcggc tttcaagcca tgattaccca tttcacaagg tacttgtcat    1080
tgagaatacg gattatggac ttgcagagta atttccccat gtttgtcgga agagcatatt    1140
accacggttg tccgtcaaac ccatttagga tactgttcta tgtaataaaa ctaaggatta    1200
ttaatttccc ttttaatcct gtctccagtt tgagcatgaa attatattta ttttatctta    1260
gaaaggtcaa ataagatttt gttttaccctc tgtaaaactt ttgtttgtat tggaaaggaa    1320
gtgccgtctc aaaaaaaaaa aaaaaaaa                                       1348
```

<210> SEQ ID NO 2
<211> LENGTH: 350
<212> TYPE: PRT
<213> ORGANISM: Cuphea  Hookeriana

<400> SEQUENCE: 2

```
Ser Ser Thr Ala Val Ala Ala Ala Leu Glu Leu Val Asp Pro Pro Gly
1               5                   10                  15
```

```
Cys Arg Asn Ser Ala Arg Ala Asp Leu Gly Ala Asp Arg Leu Ser Lys
             20                  25                  30

Ile Asp Lys Glu Arg Ala Gly Val Leu Val Gly Thr Gly Met Gly Gly
         35                  40                  45

Leu Thr Val Phe Ser Asp Gly Val Gln Ser Leu Ile Glu Lys Gly His
     50                  55                  60

Arg Lys Ile Thr Pro Phe Phe Ile Pro Tyr Ala Ile Thr Asn Met Gly
 65                  70                  75                  80

Ser Ala Leu Leu Ala Ile Glu Phe Gly Leu Met Gly Pro Asn Tyr Ser
                 85                  90                  95

Ile Ser Thr Ala Cys Ala Thr Ser Asn Tyr Cys Phe His Ala Ala Ala
            100                 105                 110

Asn His Ile Arg Arg Gly Glu Ala Asp Leu Met Ile Ala Gly Gly Thr
        115                 120                 125

Glu Ala Ala Ile Ile Pro Ile Gly Leu Gly Gly Phe Val Ala Cys Arg
    130                 135                 140

Ala Leu Ser Gln Arg Asn Asp Asp Pro Gln Thr Ala Ser Arg Pro Trp
145                 150                 155                 160

Asp Lys Asp Arg Asp Gly Phe Val Met Gly Glu Gly Ala Gly Val Leu
                165                 170                 175

Val Met Glu Ser Leu Glu His Ala Met Arg Arg Gly Ala Pro Ile Ile
            180                 185                 190

Ala Glu Tyr Leu Gly Gly Ala Ile Asn Cys Asp Ala Tyr His Met Thr
        195                 200                 205

Asp Pro Arg Ala Asp Gly Leu Gly Val Ser Ser Cys Ile Glu Ser Ser
    210                 215                 220

Leu Glu Asp Ala Gly Val Ser Pro Glu Glu Val Asn Tyr Ile Asn Ala
225                 230                 235                 240

His Ala Thr Ser Thr Leu Ala Gly Asp Leu Ala Glu Ile Asn Ala Ile
                245                 250                 255

Lys Lys Val Phe Lys Asn Thr Asp Ile Lys Ile Asn Ala Thr Lys
            260                 265                 270

Ser Met Ile Gly His Cys Leu Gly Ala Ser Gly Gly Leu Glu Ala Ile
        275                 280                 285

Ala Thr Ile Lys Gly Ile Asn Thr Gly Trp Leu His Pro Ser Ile Asn
    290                 295                 300

Gln Phe Asn Pro Glu Pro Ser Val Glu Phe Asp Thr Val Ala Asn Lys
305                 310                 315                 320

Lys Gln Gln His Glu Val Asn Val Ala Ile Ser Asn Ser Phe Gly Phe
                325                 330                 335

Gly Gly His Asn Ser Val Val Ala Phe Ser Ala Phe Lys Pro
            340                 345                 350

<210> SEQ ID NO 3
<211> LENGTH: 1703
<212> TYPE: DNA
<213> ORGANISM: Cuphea Hookeriana
<220> FEATURE:
<221> NAME/KEY: misc_feature
<222> LOCATION: (1)...(1703)
<223> OTHER INFORMATION: n = A,T,C or G

<400> SEQUENCE: 3
aaattaaccc tcactaaagg gaacaaaagc tggagctcca ccgnggtggc ggccgctcta      60
gaactagtgg atcccccggg ctgcaggaat tcggcacgag ccggcatggg cctcgtctcc     120
```

-continued

```
gtattcggct ccgacgtcga ctcttattac gaaaagctcc tctccggcga gagcgggatc      180
agcttaatcg accgcttcga cgcttccaag ttccccacca ggttcggcgg ccagatccgg      240
ggattcaacg cgacgggata catcgacggg aagaacgaca ggaggctcga cgattgcctc      300
gctactgcat tgtcgccggg aagaaggctc tcgaaaattc cgatctcggc ggtgaaagcc      360
tctccaagat tgataaggag agagctggag tgctagttgg aactggtatg ggtggcctaa      420
ccgtcttctc tgacggggtt cagaatctca tcgagaaagg tcaccggaag atctccccgt      480
ttttcattcc ctatgccatt acaaacatgg ggtctgctct gcttgccatc gatttgggtc      540
tgatgggccc aaactattcg atttcaactg catgtgctac ttccaactac tgcttttatg      600
ccgctgccaa tcatatccgc cgaggcgagg ctgacctcat gattgctgga ggaactgagg      660
ctgcaatcat tccaattggg ttaggaggat tcgttgcctg cagggcttta tctcaaagga      720
atgatgaccc tcagactgcc tcaaggccgt gggataagga ccgtgatggt tttgtgatgg      780
gcgaaggggc tggagtattg gttatggaga gcttggaaca tgcaatgaaa cgaggagcgc      840
cgattattgc agaatatttg ggaggtgcag tcaattgtga tgcttatcat atgactgatc      900
caagggctga tgggcttggt gtctcctctt gcattgagag cagtctggaa gatgctgggg      960
tctcacctga gaggtcaat tacataaatg ctcatgcgac ttccactctt gctgggatc     1020 ttgccgagat aaatgccatc aagaaggttt tcaagaacac caaggaaatc acaatcaatg     1080
caactaagtc gatgatcgga cactgtcttg gagcatcagg gggtcttgaa gccattgcga     1140
caattaaggg aataaccacc ggctggcttc atcccagcat aaaccaattc aatcccgagc     1200
catcagtgga attcgacaca gttgccaaca agaagcagca acatgaagtg aatgttgcta     1260
tctcaaattc attcggattc ggaggccaca actcagttgt agctttctca gccttcaagc     1320
catgattact cggttcaaat gcaaatttgt tgctgagaca gtgagcttca acttgcagag     1380 caattttta catgccttgt cgtcggaaga gcgtaatacc gggatagttc cttgatagtt     1440
catttaggat gttttactgc aataatcgaa gattatttcc attctaatcc agtctccgnc     1500
gagtttgaga atctatctgt ttgtattaga agaacgagg caagattttg tttcatgttt     1560
gtgtttgtat tactttcttt ttgcccttgt caatggcatt taagataagc ttataaaaaa     1620 aaaaaaaaa aaaaaactc gaggggggc ccggtaccca attcgccta tagtgagtcg     1680 tatgacaatt cactgtccgt cgg                                              1703
```

<210> SEQ ID NO 4
<211> LENGTH: 441
<212> TYPE: PRT
<213> ORGANISM: Cuphea  Hookeriana
<220> FEATURE:
<221> NAME/KEY: VARIANT
<222> LOCATION: (1)...(441)
<223> OTHER INFORMATION: Xaa = Any Amino Acid

<400> SEQUENCE: 4

```
Lys Leu Thr Leu Thr Lys Gly Asn Lys Ser Trp Ser Ser Thr Xaa Val
 1               5                  10                  15

Ala Ala Ala Leu Glu Leu Val Asp Pro Pro Gly Cys Arg Asn Ser Ala
            20                  25                  30

Arg Ala Gly Met Gly Leu Val Ser Val Phe Gly Ser Asp Val Asp Ser
        35                  40                  45

Tyr Tyr Glu Lys Leu Leu Ser Gly Glu Ser Gly Ile Ser Leu Ile Asp
    50                  55                  60
```

-continued

Arg Phe Asp Ala Ser Lys Phe Pro Thr Arg Phe Gly Gln Ile Arg
 65                  70                  75                  80

Gly Phe Asn Ala Thr Gly Tyr Ile Asp Gly Lys Asn Asp Arg Arg Leu
                 85                  90                  95

Asp Asp Cys Leu Arg Tyr Cys Ile Val Ala Gly Lys Lys Ala Leu Glu
                100                 105                 110

Asn Ser Asp Leu Gly Gly Glu Ser Leu Ser Lys Ile Asp Lys Glu Arg
                115                 120                 125

Ala Gly Val Leu Val Gly Thr Gly Met Gly Gly Leu Thr Val Phe Ser
130                 135                 140

Asp Gly Val Gln Asn Leu Ile Glu Lys Gly His Arg Lys Ile Ser Pro
145                 150                 155                 160

Phe Phe Ile Pro Tyr Ala Ile Thr Asn Met Gly Ser Ala Leu Leu Ala
                165                 170                 175

Ile Asp Leu Gly Leu Met Gly Pro Asn Tyr Ser Ile Ser Thr Ala Cys
                180                 185                 190

Ala Thr Ser Asn Tyr Cys Phe Tyr Ala Ala Ala Asn His Ile Arg Arg
                195                 200                 205

Gly Glu Ala Asp Leu Met Ile Ala Gly Gly Thr Glu Ala Ala Ile Ile
210                 215                 220

Pro Ile Gly Leu Gly Gly Phe Val Ala Cys Arg Ala Leu Ser Gln Arg
225                 230                 235                 240

Asn Asp Asp Pro Gln Thr Ala Ser Arg Pro Trp Asp Lys Asp Arg Asp
                245                 250                 255

Gly Phe Val Met Gly Glu Gly Ala Gly Val Leu Val Met Glu Ser Leu
                260                 265                 270

Glu His Ala Met Lys Arg Gly Ala Pro Ile Ile Ala Glu Tyr Leu Gly
                275                 280                 285

Gly Ala Val Asn Cys Asp Ala Tyr His Met Thr Asp Pro Arg Ala Asp
                290                 295                 300

Gly Leu Gly Val Ser Ser Cys Ile Glu Ser Ser Leu Glu Asp Ala Gly
305                 310                 315                 320

Val Ser Pro Glu Glu Val Asn Tyr Ile Asn Ala His Ala Thr Ser Thr
                325                 330                 335

Leu Ala Gly Asp Leu Ala Glu Ile Asn Ala Ile Lys Lys Val Phe Lys
                340                 345                 350

Asn Thr Lys Glu Ile Thr Ile Asn Ala Thr Lys Ser Met Ile Gly His
                355                 360                 365

Cys Leu Gly Ala Ser Gly Gly Leu Glu Ala Ile Ala Thr Ile Lys Gly
370                 375                 380

Ile Thr Thr Gly Trp Leu His Pro Ser Ile Asn Gln Phe Asn Pro Glu
385                 390                 395                 400

Pro Ser Val Glu Phe Asp Thr Val Ala Asn Lys Lys Gln Gln His Glu
                405                 410                 415

Val Asn Val Ala Ile Ser Asn Ser Phe Gly Phe Gly Gly His Asn Ser
                420                 425                 430

Val Val Ala Phe Ser Ala Phe Lys Pro
                435                 440

<210> SEQ ID NO 5
<211> LENGTH: 2046
<212> TYPE: DNA
<213> ORGANISM: Cuphea Hookeriana

<400> SEQUENCE: 5

```
actaaggga caaaagctg gagctccacc gcggtggcgg ccgctctaga actagtggat      60
ccccgggct gcaggaattc ggcacgagtt ttcttacttg gtcggctca gctcaggtgt     120
tccaatggcg accgcttctt gcatggttgc gtcccctttc tgtacgtggc tcgtagctgc    180
atgcatgccc acttcatccg acaacgaccc acgttccctt ccccacaagc ggctccgcct    240
ctcccgtcgc cggaggactc tctcctccca ttgctccctc cgcggatcca ccttccaatg    300
cctcgatcct tgcaaccagc aacgcttcct cggggataac ggattcgctt ccctcttcgg    360
atccaagcct cttcgttcaa atcgcggcca cctgaggctc ggccgcactt cccattccgg    420
ggaggtcatg gctgtggcta tgcaacctgc acaggaagtc tccacaaata gaaacctgc     480
taccaagcaa aggcgagtag ttgtgacagg tatgggcgtg gtgactcctc taggccatga    540
ccccgatgtt tactacaaca atctcctaga cggaataagt ggcataagtg agatagagaa    600
cttcgactgc tctcagtttc ccacgagaat tgccggagat atcaagtctt tttccacaga    660
tggctgggtg gccccaaagt tctccgagag gatggacaag ttcatgcttt acatgctgac    720
tgcaggcaag aaagcattag cagatggtgg aatcactgaa gatgcgatga agagctcaa    780
taaaagaaag tgtggagttc tcattggctc cggattgggc ggtatgaagg tattcagcga    840
ttccattgaa gctctgagga cttcatataa gaagatcagt ccctttgtg taccttttc     900
taccacaaat atgggatccg ctattcttgc aatggacttg ggatggatgg ccctaacta    960
ttcgatatca actgcctgtg caacaagtaa cttctgtata ctgaatgctg cgaaccacat   1020
aatcaaaggc gaagcagaca tgatgctttg tggtggctcg gatgcggccg ttttacctgt   1080
tggtttggga ggtttcgtag catgccgagc tttgtcacag aggaataatg accctaccaa   1140
agcttcgaga ccatgggaca gtaatcgtga tggatttgtg atgggagaag gagctggagt   1200
tttacttctt gaggagttag agcatgcaaa gaaaagaggt gcaaccattt atgcggaatt   1260
tctaggtggg agtttcactt gcgacgccta ccacatgacc gagcctcacc ctgaaggagc   1320
tggtgtgatc ctctgcatag agaaggcctt ggctcagtcc ggagtctcga gggaagacgt   1380
aaattacata aatgcgcatg caacttccac tcctgctgga gatatcaagg aataccaagc   1440
tctcgcccac tgtttcggcc aaaacagtga gctgagagtg aattccacca aatcgatgat   1500
cggtcacctt cttggaggag ctggtggcgt agaagcagtt gcagtagttc aggcaataag   1560
gacaggatgg atccatccaa atattaattt ggaagacccg gacgaaggcg tggatgcaaa   1620
actgctcgtc ggccctaaga aggagaaact gaaggtcaag gtcggtttgt ccaattcatt   1680
tgggttcggc ggccataact catccatact atttgccccc tgcaactaga aaagagtctg   1740
tggaagccga gagtctttga gaactcatgc acgttagtag cttcttatgc ctctgaaacc   1800
gagatagacc ggctactcga ggggatgcca aagatactcc ttgccggtat tggtgttaag   1860
agatcactgc ttgtcccttt tattttcttc ttcttttgag agctttaacc gaggtagtcg   1920
tattttcgag cttttcgaat acatgttcgt tatcggatca atgtgtttct tctaagatca   1980
tttgtaatgc atattttgaa aaaccacatc tcagtatgca aataaaaaaa aaaaaaaaa   2040
aaaaaa                                                              2046
```

<210> SEQ ID NO 6
<211> LENGTH: 534
<212> TYPE: PRT
<213> ORGANISM: Cuphea Hookeriana

<400> SEQUENCE: 6

-continued

```
Met Ala Thr Ala Ser Cys Met Val Ala Ser Pro Phe Cys Thr Trp Leu
 1               5                  10                 15

Val Ala Ala Cys Met Pro Thr Ser Ser Asp Asn Asp Pro Arg Ser Leu
            20                  25                  30

Ser His Lys Arg Leu Arg Leu Ser Arg Arg Arg Thr Leu Ser Ser
         35                  40                  45

His Cys Ser Leu Arg Gly Ser Thr Phe Gln Cys Leu Asp Pro Cys Asn
 50                      55                  60

Gln Gln Arg Phe Leu Gly Asp Asn Gly Phe Ala Ser Leu Phe Gly Ser
 65                  70                  75                  80

Lys Pro Leu Arg Ser Asn Arg Gly His Leu Arg Leu Gly Arg Thr Ser
                 85                  90                  95

His Ser Gly Glu Val Met Ala Val Ala Met Gln Pro Ala Gln Glu Val
             100                 105                 110

Ser Thr Asn Lys Lys Pro Ala Thr Lys Gln Arg Val Val Val Thr
             115                 120                 125

Gly Met Gly Val Val Thr Pro Leu Gly His Asp Pro Asp Val Tyr Tyr
         130                 135                 140

Asn Asn Leu Leu Asp Gly Ile Ser Gly Ile Ser Glu Ile Glu Asn Phe
145                 150                 155                 160

Asp Cys Ser Gln Phe Pro Thr Arg Ile Ala Gly Glu Ile Lys Ser Phe
                 165                 170                 175

Ser Thr Asp Gly Trp Val Ala Pro Lys Phe Ser Glu Arg Met Asp Lys
             180                 185                 190

Phe Met Leu Tyr Met Leu Thr Ala Gly Lys Lys Ala Leu Ala Asp Gly
         195                 200                 205

Gly Ile Thr Glu Asp Ala Met Lys Glu Leu Asn Lys Arg Lys Cys Gly
     210                 215                 220

Val Leu Ile Gly Ser Gly Leu Gly Gly Met Lys Val Phe Ser Asp Ser
225                 230                 235                 240

Ile Glu Ala Leu Arg Thr Ser Tyr Lys Lys Ile Ser Pro Phe Cys Val
                 245                 250                 255

Pro Phe Ser Thr Thr Asn Met Gly Ser Ala Ile Leu Ala Met Asp Leu
             260                 265                 270

Gly Trp Met Gly Pro Asn Tyr Ser Ile Ser Thr Ala Cys Ala Thr Ser
         275                 280                 285

Asn Phe Cys Ile Leu Asn Ala Ala Asn His Ile Ile Lys Gly Glu Ala
     290                 295                 300

Asp Met Met Leu Cys Gly Gly Ser Asp Ala Ala Val Leu Pro Val Gly
305                 310                 315                 320

Leu Gly Gly Phe Val Ala Cys Arg Ala Leu Ser Gln Arg Asn Asn Asp
                 325                 330                 335

Pro Thr Lys Ala Ser Arg Pro Trp Asp Ser Asn Arg Asp Gly Phe Val
             340                 345                 350

Met Gly Glu Gly Ala Gly Val Leu Leu Leu Glu Glu Leu Glu His Ala
         355                 360                 365

Lys Lys Arg Gly Ala Thr Ile Tyr Ala Glu Phe Leu Gly Gly Ser Phe
     370                 375                 380

Thr Cys Asp Ala Tyr His Met Thr Glu Pro His Pro Glu Gly Ala Gly
385                 390                 395                 400

Val Ile Leu Cys Ile Glu Lys Ala Leu Ala Gln Ser Gly Val Ser Arg
                 405                 410                 415

Glu Asp Val Asn Tyr Ile Asn Ala His Ala Thr Ser Thr Pro Ala Gly
```

```
                420            425            430
Asp Ile Lys Glu Tyr Gln Ala Leu Ala His Cys Phe Gly Gln Asn Ser
        435                 440                 445
Glu Leu Arg Val Asn Ser Thr Lys Ser Met Ile Gly His Leu Leu Gly
    450                 455                 460
Gly Ala Gly Val Glu Ala Val Ala Val Gln Ala Ile Arg Thr
465                 470                 475                 480
Gly Trp Ile His Pro Asn Ile Asn Leu Glu Asp Pro Asp Glu Gly Val
            485                 490                 495
Asp Ala Lys Leu Leu Val Gly Pro Lys Lys Glu Lys Leu Lys Val Lys
        500                 505                 510
Val Gly Leu Ser Asn Ser Phe Gly Phe Gly Gly His Asn Ser Ser Ile
        515                 520                 525
Leu Phe Ala Pro Cys Asn
    530

<210> SEQ ID NO 7
<211> LENGTH: 1921
<212> TYPE: DNA
<213> ORGANISM: Cuphea  Hookeriana

<400> SEQUENCE: 7
cggcacgagg tcacctctta cctcgcctgc ttcgagccct gccatgacta ctacacctcc     60
gcatccttgt tcggatccag gcccatccgc accacccgca ggcaccggag ctcaatcga    120
gcttcccctt ccggggaggc aatggctgtg ctctgcaac ctgcacagga agttaccaca    180
aagaagaagc caagtatcaa acagcggcga gtagttgtga ctggaatggg tgtggtgact    240
cctctaggcc atgaccctga tgttttctac aataatctgc ttgatggaac gagtggcata    300
agtgagatag agaccttga ttgtgctcaa tttcctacga gaattgctgg agagatcaag    360
tctttctcca cagatggttg ggtggccccg aagctctcca agaggatgga caagttcatg    420
ctttacatgc tgactgccgg caagaaagca ttaacaaatg gtggaatcac cgaagatgtg    480
atgaaagagc tagataaaag aaaatgcgga gttctcattg gctcagcaat gggtggaatg    540
aaggtattca atgatgccat tgaagcccta aggatttcat ataagaagat gaatcccttt    600
tgtgtacctt tcgctaccac aaatatggga tcagctatgc ttgcaatgga cttgggatgg    660
atgggcccca actactcgat atctactgct tgtgcaacga gtaacttttg tatcctgaat    720
gctgcgaacc acataatcag aggcgaagca gatgtgatgc tttgcggggg ctcagatgcg    780
gtaatcatac ctattggtat gggaggtttt gttcatgcc gagctttgtc acagagaaat    840
gccgacccta ctaaagcttc aagaccatgg acagtaatc gtgatggatt tgttatgggg    900
gaaggagctg gagtgctact actagaggag ttagagcatg caaagaaaag aggtgcgact    960
atttacgcag aatttctagg tggaagtttc acttgcgatg cctaccacat gaccgagcct   1020
caccctgatg gagctggagt gattctctgc atagagaagg ctttggctca gtcaggagtc   1080
tctaggaag acgtaaatta cataaatgca catgccacat ccactccagc tggagatatc   1140
aaagagtacc aagctcttat ccactgtttc ggccaaaaca acgagttaaa agtgaattct   1200
accaaatcaa tgattggtca ccttctcgga gcagccggtg tgtggaagc agtttcagta   1260
gttcaggcaa taggactgg gtggatccat ccgaatatta atttggaaaa cccagatgaa   1320
ggcgtggata ccaaattgct cgtgggccct aagaaggaga gactgaacat taaggtcggt   1380
ttgtctaatt cattcggggtt tggtgggcac aactcgtcca tactcttcgc cccttacaac   1440
```

-continued

```
tagggcgttt catgtgtgga attctactca atctatcaaa gctgaagttt tgaggactcc   1500
agcatgttgg tagctcctta cgtctctaga catgcccatg agttttgtgt cgggagctgt   1560
agtcggaacc atgacggatt gagtactcat ggcgacacag gatatactcc ttgctagaat   1620
tgttagagca ctattcatta tcccattttt tttctgaaat ctccctcctt acggtagttg   1680
tactttcgag cgtttcatcg agtcagtgaa gaagagaaca aagctaactc gggcacgtag   1740
taaccatttg cccttttgttt tgctctctat tttatcgccg ttttgtgggt taaaatttgt   1800
aaaactagac gactggtttg ttttctcttg atcattggag atgtatggcc atatttgcct   1860
ttcattgatg ataaaaaaaa aaaaaaaaaa aaaaaaaaaa aaaaaaaaaa aaaaaaaaa    1920 a                                                                   1921
```

<210> SEQ ID NO 8
<211> LENGTH: 420
<212> TYPE: PRT
<213> ORGANISM: Cuphea Hookeriana

<400> SEQUENCE: 8

```
Lys Lys Lys Pro Ser Ile Lys Gln Arg Arg Val Val Thr Gly Met
1               5                   10                  15

Gly Val Val Thr Pro Leu Gly His Asp Pro Asp Val Phe Tyr Asn Asn
                20                  25                  30

Leu Leu Asp Gly Thr Ser Gly Ile Ser Glu Ile Glu Thr Phe Asp Cys
            35                  40                  45

Ala Gln Phe Pro Thr Arg Ile Ala Gly Glu Ile Lys Ser Phe Ser Thr
        50                  55                  60

Asp Gly Trp Val Ala Pro Lys Leu Ser Lys Arg Met Asp Lys Phe Met
65                  70                  75                  80

Leu Tyr Met Leu Thr Ala Gly Lys Lys Ala Leu Thr Asn Gly Gly Ile
                85                  90                  95

Thr Glu Asp Val Met Lys Glu Leu Asp Lys Arg Lys Cys Gly Val Leu
            100                 105                 110

Ile Gly Ser Ala Met Gly Gly Met Lys Val Phe Asn Asp Ala Ile Glu
        115                 120                 125

Ala Leu Arg Ile Ser Tyr Lys Lys Met Asn Pro Phe Cys Val Pro Phe
    130                 135                 140

Ala Thr Thr Asn Met Gly Ser Ala Met Leu Ala Met Asp Leu Gly Trp
145                 150                 155                 160

Met Gly Pro Asn Tyr Ser Ile Ser Thr Ala Cys Ala Thr Ser Asn Phe
                165                 170                 175

Cys Ile Leu Asn Ala Ala Asn His Ile Ile Arg Gly Glu Ala Asp Val
            180                 185                 190

Met Leu Cys Gly Gly Ser Asp Ala Val Ile Ile Pro Ile Gly Met Gly
        195                 200                 205

Gly Phe Val Ala Cys Arg Ala Leu Ser Gln Arg Asn Ala Asp Pro Thr
    210                 215                 220

Lys Ala Ser Arg Pro Trp Asp Ser Asn Arg Asp Gly Phe Val Met Gly
225                 230                 235                 240

Glu Gly Ala Gly Val Leu Leu Leu Glu Glu Leu Glu His Ala Lys Lys
                245                 250                 255

Arg Gly Ala Thr Ile Tyr Ala Glu Phe Leu Gly Gly Ser Phe Thr Cys
            260                 265                 270

Asp Ala Tyr His Met Thr Glu Pro His Pro Asp Gly Ala Gly Val Ile
        275                 280                 285
```

Leu Cys Ile Glu Lys Ala Leu Ala Gln Ser Gly Val Ser Arg Glu Asp
            290                 295                 300
Val Asn Tyr Ile Asn Ala His Ala Thr Ser Thr Pro Ala Gly Asp Ile
305                 310                 315                 320
Lys Glu Tyr Gln Ala Leu Ile His Cys Phe Gly Gln Asn Asn Glu Leu
                325                 330                 335
Lys Val Asn Ser Thr Lys Ser Met Ile Gly His Leu Leu Gly Ala Ala
            340                 345                 350
Gly Gly Val Glu Ala Val Ser Val Gln Ala Ile Arg Thr Gly Trp
            355                 360                 365
Ile His Pro Asn Ile Asn Leu Glu Asn Pro Asp Glu Gly Val Asp Thr
370                 375                 380
Lys Leu Leu Val Gly Pro Lys Lys Glu Arg Leu Asn Ile Lys Val Gly
385                 390                 395                 400
Leu Ser Asn Ser Phe Gly Phe Gly Gly His Asn Ser Ser Ile Leu Phe
                405                 410                 415
Ala Pro Tyr Asn
            420

<210> SEQ ID NO 9
<211> LENGTH: 1713
<212> TYPE: DNA
<213> ORGANISM: Cuphea pullcherrima

<400> SEQUENCE: 9

```
ctggtacgcc tgcaggtacc ggtccggaat cccgggtcg acccacgcgt ccgtcttccc      60
actccgatcg ttcttcttcc accgcatctc ttctcttctc ttggcttctc cgccatcctc    120
cgccgccatg cattccctcc agtcaccctc ccttcgggcc tcccgctcg accccttccg     180
ccccaaatca tccaccgtcc gcccctcca ccgagcatca attcccaacg tccgggccgc    240
ttccccacc gtctccgctc ccaagcgcga gaccgacccc aagaagcgcg tcgtgatcac     300
cggaatgggc cttgtctccg ttttcggctc cgacgtcgat gcgtactacg acaagctcct   360
gtcaggcgag agcgggatcg cccaatcga ccgcttcgac gcctccaagt tccccaccag    420
gttcggcggc cagattcgtg gcttcaactc catgggatac attgacggca aaaacgacag    480
gcggcttgat gattgccttc gctactgcat tgtcgccggg aagaagtctc ttgaggacgc    540
cgatctcggt gccgaccgcc tctccaagat cgacaaggag agagccggag tgctggttgg    600
gacaggaatg ggtggtctga ctgtcttctc tgacggggtt caatctctta cgagaaggg    660
tcaccggaaa atcacccctt tcttcatccc ctatgccatt acaaacatgg ggtctgccct    720
gctcgctatt gaactcggtc tgatgggccc aaactattca atttccactg catgtgccac    780
ttccaactac tgcttccatg ctgctgctaa tcatatccgc cgtggtgagg ctgatcttat    840
gattgctgga ggcactgagg ccgcaatcat tccaattggg ttgggaggct tgtggcttg    900
cagggctctg tctcaaagga acgatgaccc tcagactgcc tctaggccct gggataaaga    960
ccgtgatggt tttgtgatgg gtgaaggtgc tggagtgttg gtgctggaga gcttggaaca   1020
tgcaatgaaa cgaggagcac ctattattgc agagtatttg ggaggtgcaa tcaactgtga   1080
tgcttatcac atgactgacc aagggctga tggtctcggt gtctcctctt gcattgagag    1140
tagccttgaa gatgctggcg tctcacctga gaggtcaat tacataaatg ctcatgcgac    1200
ttctactcta gctggggatc tcgccgagat aaatgccatc aagaaggttt tcaagaacac    1260
aaaggatatc aaaattaatg caactaagtc aatgatcgga cactgtcttg gagcctctgg   1320
```

-continued

```
aggtcttgaa gctatagcga ctattaaggg aataaacacc ggctggcttc atcccagcat    1380
taatcaattc aatcctgagc catccgtgga gttcgacact gttgccaaca agaagcagca    1440
acacgaagtt aatgttgcga tctcgaattc atttggattc ggaggccaca actcagtcgt    1500
ggctttctcg gctttcaagc catgattacc catttcacaa ggcacttgtc attgagagta    1560
cggttgttcg tcaaacccat ttaggatact gttctatgta aaaaaagta aggattatca     1620 ctttcccttc taatcctgtc tccagtttga gaatgaaatt atatttattt taaaaaaaaa    1680
aaaaaagggc ggccgctcta gaggatccaa gct                                 1713
```

<210> SEQ ID NO 10
<211> LENGTH: 465
<212> TYPE: PRT
<213> ORGANISM: Cuphea pullcherrima

<400> SEQUENCE: 10

```
Met His Ser Leu Gln Ser Pro Ser Leu Arg Ala Ser Pro Leu Asp Pro
  1               5                  10                  15

Phe Arg Pro Lys Ser Ser Thr Val Arg Pro Leu His Arg Ala Ser Ile
             20                  25                  30

Pro Asn Val Arg Ala Ala Ser Pro Thr Val Ser Ala Pro Lys Arg Glu
         35                  40                  45

Thr Asp Pro Lys Lys Arg Val Val Ile Thr Gly Met Gly Leu Val Ser
     50                  55                  60

Val Phe Gly Ser Asp Val Asp Ala Tyr Tyr Asp Lys Leu Leu Ser Gly
 65                  70                  75                  80

Glu Ser Gly Ile Gly Pro Ile Asp Arg Phe Asp Ala Ser Lys Phe Pro
                 85                  90                  95

Thr Arg Phe Gly Gly Gln Ile Arg Gly Phe Asn Ser Met Gly Tyr Ile
            100                 105                 110

Asp Gly Lys Asn Asp Arg Arg Leu Asp Asp Cys Leu Arg Tyr Cys Ile
        115                 120                 125

Val Ala Gly Lys Lys Ser Leu Glu Asp Ala Asp Leu Gly Ala Asp Arg
    130                 135                 140

Leu Ser Lys Ile Asp Lys Glu Arg Ala Gly Val Leu Val Gly Thr Gly
145                 150                 155                 160

Met Gly Gly Leu Thr Val Phe Ser Asp Gly Val Gln Ser Leu Ile Glu
                165                 170                 175

Lys Gly His Arg Lys Ile Thr Pro Phe Phe Ile Pro Tyr Ala Ile Thr
            180                 185                 190

Asn Met Gly Ser Ala Leu Leu Ala Ile Glu Leu Gly Leu Met Gly Pro
        195                 200                 205

Asn Tyr Ser Ile Ser Thr Ala Cys Ala Thr Ser Asn Tyr Cys Phe His
    210                 215                 220

Ala Ala Ala Asn His Ile Arg Arg Gly Glu Ala Asp Leu Met Ile Ala
225                 230                 235                 240

Gly Gly Thr Glu Ala Ala Ile Ile Pro Ile Gly Leu Gly Gly Phe Val
                245                 250                 255

Ala Cys Arg Ala Leu Ser Gln Arg Asn Asp Asp Pro Gln Thr Ala Ser
            260                 265                 270

Arg Pro Trp Asp Lys Asp Arg Asp Gly Phe Val Met Gly Glu Gly Ala
        275                 280                 285

Gly Val Leu Val Leu Glu Ser Leu Glu His Ala Met Lys Arg Gly Ala
    290                 295                 300
```

```
Pro Ile Ile Ala Glu Tyr Leu Gly Gly Ala Ile Asn Cys Asp Ala Tyr
305                 310                 315                 320

His Met Thr Asp Pro Arg Ala Asp Gly Leu Gly Val Ser Ser Cys Ile
                325                 330                 335

Glu Ser Ser Leu Glu Asp Ala Gly Val Ser Pro Glu Val Asn Tyr
            340                 345                 350

Ile Asn Ala His Ala Thr Ser Thr Leu Ala Gly Asp Leu Ala Glu Ile
                355                 360                 365

Asn Ala Ile Lys Lys Val Phe Lys Asn Thr Lys Asp Ile Lys Ile Asn
        370                 375                 380

Ala Thr Lys Ser Met Ile Gly His Cys Leu Gly Ala Ser Gly Gly Leu
385                 390                 395                 400

Glu Ala Ile Ala Thr Ile Lys Gly Ile Asn Thr Gly Trp Leu His Pro
                405                 410                 415

Ser Ile Asn Gln Phe Asn Pro Glu Pro Ser Val Glu Phe Asp Thr Val
            420                 425                 430

Ala Asn Lys Lys Gln Gln His Glu Val Asn Val Ala Ile Ser Asn Ser
        435                 440                 445

Phe Gly Phe Gly Gly His Asn Ser Val Val Ala Phe Ser Ala Phe Lys
    450                 455                 460

Pro
465
```

<210> SEQ ID NO 11
<211> LENGTH: 1802
<212> TYPE: DNA
<213> ORGANISM: Cuphea pullcherrima

<400> SEQUENCE: 11

| | | | | | |
|---|---|---|---|---|---|
| ggtcgaccca | cgcgtccggg | ctttccgacc | acatttcatt | tcttgcctcg | ttatctccgc | 60 |
| cgctcctccg | ccgtcgttcg | ccgccgccgc | catgcaatcc | ctccactccc | cttccctccg | 120 |
| cccctcccct | ctcgagccct | tccgcctcaa | ttccccctcc | tccgccgccg | ctctccgccc | 180 |
| cctccgtcgc | gccagcctcc | ccgtcatccg | tgctgccacc | gcctccgccc | ccaagcgcga | 240 |
| gtccgaccce | aagaagcggg | tcgtcatcac | cggcatgggc | ctcgtctccg | tcttcggctc | 300 |
| cgacgtcgac | gcctactacg | acaagctgct | ctccggcgag | agcggcatca | gcctaatcga | 360 |
| ccgcttcgac | gcttccaaat | tccccaccag | gttcgccggc | cagatccgtg | gcttcaacgc | 420 |
| gacgggctac | atcgacggca | gaacgaccg | gcggctcgac | gattgcctcc | gctactgcat | 480 |
| tgtcgccggc | aagaaggctc | tcgaagacgc | cgatctcgcc | ggccaatccc | tctccaagat | 540 |
| tgataaggag | agggccggag | tgctagttgg | aaccggtatg | ggtggcctaa | ctgtcttctc | 600 |
| tgacgggggtt | cagaatctca | tcgagaaagg | tcaccggaag | atctccccgt | ttttcattcc | 660 |
| atatgccatt | acaaacatgg | ggtctgcgct | gcttgccatc | gatttgggtc | tgatgggccc | 720 |
| aaactattcg | atttcaactg | catgtgctac | ttccaactac | tgcttttatg | ctgccgccaa | 780 |
| tcatatccgc | cgaggtgagg | ctgacctgat | gattgctgga | ggaactgagg | ctgcggtcat | 840 |
| tccaattggt | ttaggaggat | tcgttgcctg | cagggcttta | tctcaaagga | atgatgatcc | 900 |
| tcagactgcc | tcaaggccgt | gggataagga | ccgtgatggc | tttgtgatgg | gtgaagggggc | 960 |
| tggagtattg | gttatggaga | gcttggagca | tgcaatgaaa | cgggagcgc | cgattattgc | 1020 |
| agaatatttg | ggaggtgcag | tcaactgtga | tgcttatcat | atgactgatc | caagggctga | 1080 |
| tgggcttggt | gtctcctcgt | gcattgagag | cagtctcgaa | gatgccgggg | tctcacctga | 1140 |

-continued

```
agaggtcaat tacataaatg ctcatgcgac ttctactctt gctggggatc ttgccgagat   1200
aaatgccatt aagaaagttt tcaagaacac caaggaaatc aaaatcaatg caactaagtc   1260
aatgatcgga cactgtcttg gagcatcagg aggtcttgaa gccatcgcaa ccattaaggg   1320
aataaccacc ggctggcttc atcccagcat taatcaattt aatcccgagc atcggtgga   1380 cttcaacact gttgccaaca aaagcagca acatgaagtg aacgtcgcta tctcgaattc   1440
ttttggattt ggagggcaca actcggttgt ggcattctca gctttcaagc catgaattct   1500
acttggttca aaatgcacac cagttgctga gatagggctt caacttgcag agcaattttt   1560
taaatgcctt gtcggaagag cgtaataccg gataggtcg gtcctttgat agttcctcga   1620
agccatttag gatgatgttt tactgtaata atcgaagatg attcccattt taaatctagt   1680
ctctgattta tgtattagaa agaccaatga agattttgt gtcatgtttg tgttgtcaat   1740
gttatttaag ataaagcaaa aaaaaaaaaa aagggcggcc gctctagagg atccagctta   1800
ct                                                                  1802
```

<210> SEQ ID NO 12
<211> LENGTH: 467
<212> TYPE: PRT
<213> ORGANISM: Cuphea pullcherrima

<400> SEQUENCE: 12

```
Met Gln Ser Leu His Ser Pro Ser Leu Arg Pro Ser Pro Leu Glu Pro
  1               5                  10                  15

Phe Arg Leu Asn Ser Pro Ser Ala Ala Ala Leu Arg Pro Leu Arg
             20                  25                  30

Arg Ala Ser Leu Pro Val Ile Arg Ala Ala Thr Ala Ser Ala Pro Lys
         35                  40                  45

Arg Glu Ser Asp Pro Lys Lys Arg Val Val Ile Thr Gly Met Gly Leu
     50                  55                  60

Val Ser Val Phe Gly Ser Asp Val Asp Ala Tyr Tyr Asp Lys Leu Leu
 65                  70                  75                  80

Ser Gly Glu Ser Gly Ile Ser Leu Ile Asp Arg Phe Asp Ala Ser Lys
                 85                  90                  95

Phe Pro Thr Arg Phe Ala Gly Gln Ile Arg Gly Phe Asn Ala Thr Gly
            100                 105                 110

Tyr Ile Asp Gly Lys Asn Asp Arg Arg Leu Asp Asp Cys Leu Arg Tyr
        115                 120                 125

Cys Ile Val Ala Gly Lys Lys Ala Leu Glu Asp Ala Asp Leu Ala Gly
    130                 135                 140

Gln Ser Leu Ser Lys Ile Asp Lys Glu Arg Ala Gly Val Leu Val Gly
145                 150                 155                 160

Thr Gly Met Gly Gly Leu Thr Val Phe Ser Asp Gly Val Gln Asn Leu
                165                 170                 175

Ile Glu Lys Gly His Arg Lys Ile Ser Pro Phe Phe Ile Pro Tyr Ala
            180                 185                 190

Ile Thr Asn Met Gly Ser Ala Leu Leu Ala Ile Asp Leu Gly Leu Met
        195                 200                 205

Gly Pro Asn Tyr Ser Ile Ser Thr Ala Cys Ala Thr Ser Asn Tyr Cys
    210                 215                 220

Phe Tyr Ala Ala Ala Asn His Ile Arg Arg Gly Glu Ala Asp Leu Met
225                 230                 235                 240

Ile Ala Gly Gly Thr Glu Ala Ala Val Ile Pro Ile Gly Leu Gly Gly
```

```
              245                 250                 255
     Phe Val Ala Cys Arg Ala Leu Ser Gln Arg Asn Asp Asp Pro Gln Thr
                 260                 265                 270
     Ala Ser Arg Pro Trp Asp Lys Asp Arg Asp Gly Phe Val Met Gly Glu
                 275                 280                 285
     Gly Ala Gly Val Leu Val Met Glu Ser Leu Glu His Ala Met Lys Arg
                 290                 295                 300
     Gly Ala Pro Ile Ile Ala Glu Tyr Leu Gly Ala Val Asn Cys Asp
     305                 310                 315                 320
     Ala Tyr His Met Thr Asp Pro Arg Ala Asp Gly Leu Gly Val Ser Ser
                     325                 330                 335
     Cys Ile Glu Ser Ser Leu Glu Asp Ala Gly Val Ser Pro Glu Glu Val
                 340                 345                 350
     Asn Tyr Ile Asn Ala His Ala Thr Ser Thr Leu Ala Gly Asp Leu Ala
                 355                 360                 365
     Glu Ile Asn Ala Ile Lys Lys Val Phe Lys Asn Thr Lys Glu Ile Lys
             370                 375                 380
     Ile Asn Ala Thr Lys Ser Met Ile Gly His Cys Leu Gly Ala Ser Gly
     385                 390                 395                 400
     Gly Leu Glu Ala Ile Ala Thr Ile Lys Gly Ile Thr Thr Gly Trp Leu
                 405                 410                 415
     His Pro Ser Ile Asn Gln Phe Asn Pro Glu Pro Ser Val Asp Phe Asn
                 420                 425                 430
     Thr Val Ala Asn Lys Lys Gln Gln His Glu Val Asn Val Ala Ile Ser
                 435                 440                 445
     Asn Ser Phe Gly Phe Gly Gly His Asn Ser Val Val Ala Phe Ser Ala
             450                 455                 460
     Phe Lys Pro
     465

<210> SEQ ID NO 13
<211> LENGTH: 2369
<212> TYPE: DNA
<213> ORGANISM: Cuphea pullcherrima

<400> SEQUENCE: 13
gtacgcctgc aggtaccggt ccggaattcc cgggtcgacc cacgcgtccg cataaaagag    60
agagagaggg atccatcgaa tgcggccacc ctcctttcat cttcgattca ttaccatacc   120
attccgctga tccattttcc gccttttccg ggtctttcat cccaaagggt atcctttttct  180
atcctatctt ctcaaagggt cagtcagttc cctccaatgc ctgccgcctc ttccctgctc   240
gcttcccctc tctgtacgtg gctccttgcc gcctgcatgt ctacctcctt ccaccctcc   300
gaccctcttc cgccttccat ctcctctcct gccgacgcc tccccgccg ccggattctc   360
tcccaatgcg ccccactacc ttctgcttcc tccgccctcc gcggatccag tttccatacc   420
ctcgtcacct cttacctcgc ctgcttcgag ccctgccatg actactatac atccgcatcc   480
ttgttcggat ccagacccat tcgcaccacc cgcaggcacc ggaggctcaa tcgagcttcc   540
ccttccaggg aggcaatggc cgtggctctg caacctgaac aggaagttac cacaaagaag   600
aagccaagta tcaaacagcg gcgagtagtt gtgactggaa tgggtgtggt gactcctcta   660
ggccatgacc ctgatgtttt ctacaataat ctgcttgatg gaacgagtgg cataagcgag   720
atagagacct ttgattgtgc tcaatttcct acgagaattg ctggagagat caagtctttc   780
tccacagatg gttgggtggc cccgaagctc tctaagagga tggacaagtt catgctatac   840
```

-continued

```
atgctgaccg ctggcaagaa agcattaaca gatggtggaa tcaccgaaga tgtgatgaaa      900
gagctagata aaagaaaatg cggagttctc attggctcag caatgggtgg aatgaaggta      960
ttcaatgatg ccattgaagc cctaaggatt tcatataaga agatgaatcc cttttgtgta     1020
cctttcgcta ccacaaatat gggatcagct atgcttgcaa tggacttggg atggatgggg     1080
cccaactact cgatatctac tgcttgtgca acgagtaact tttgtataat gaatgctgcg     1140
aaccatataa tcagaggcga agcagatgtg atgctttgcg ggggctcaga tgcggtaatc     1200
atacctattg gtatgggagg ttttgttgca tgccgagctt gtcccagag aaattccgac      1260 cctactaaag cttcaagacc atgggacagt aatcgtgatg gatttgttat ggggggaagga    1320 gctggagtgc tactactaga ggagttggag catgcaaaga aaagaggtgc gactatttac     1380
gcagaatttc taggtgggag tttcacttgc gatgcctacc acatgaccga gcctcaccct     1440
gatggagctg gagtgattct ctgcatagag aaggctttgg ctcagtcagg agtctctagg     1500
gaagacgtaa attacataaa tgcccatgcc acatccactc cggctggaga tatcaaagag     1560
taccaagctc ttatccactg tttcggccaa acagagagt aaaagttaa ttcaaccaaa       1620 tcaatgattg gtcaccttct cggagcagcc ggtggtgtgg aagcagtttc agtagttcag     1680
gcaataagga ctgggtggat ccatccgaat attaatttgg aaaacccaga tgaaggcgtg     1740
gatacaaaat tgctcgtggg tcctaagaag gagagactga acgttaaggt cggtttgtct     1800
aattcatttg ggtttggtgg gcacaactcg tccatactct tcgcccctta catctaggac     1860
gtttccgtgt gtggaattct actcaacata tcaaagctga gttttgagg actccagcat     1920 gttggtagct ccttacgtct ctagacatgc ccatgagttt tgtgtccgga gctttagtcg    1980
gaaccatgac ggattgagta ctcatggcga cacttgatat actccttgct agaattgttg    2040
gtagagcaat attcattatc tcatattttt tttttctctg aaatctccct ccttgcaata    2100
gttgtacttt cgagcttttc atcgagtcag tgaagaagag aacaaagctg ttaactcggg    2160
cacgtagtaa ccatttgccc tttgttttgc tctctatttc atcaccgttt tgtggtttta    2220
aaatttgtaa aactagaaga ctggtttaga ttggtttgtt ttctcattga taattgggr     2280 atgtatgttt tggaaataaa aaaaaaaaaa aaaaaaaaa aaaaaaaaa aaaaaaaaa       2340 aaaaaaaaaa agggcggccg ctctagagg                                     2369
```

<210> SEQ ID NO 14
<211> LENGTH: 546
<212> TYPE: PRT
<213> ORGANISM: Cuphea pullcherrima

<400> SEQUENCE: 14

```
Met Pro Ala Ala Ser Ser Leu Leu Ala Ser Pro Leu Cys Thr Trp Leu
 1               5                  10                  15

Leu Ala Ala Cys Met Ser Thr Ser Phe His Pro Ser Asp Pro Leu Pro
            20                  25                  30

Pro Ser Ile Ser Ser Pro Arg Arg Arg Leu Ser Arg Arg Arg Ile Leu
        35                  40                  45

Ser Gln Cys Ala Pro Leu Pro Ser Ala Ser Ser Ala Leu Arg Gly Ser
    50                  55                  60

Ser Phe His Thr Leu Val Thr Ser Tyr Leu Ala Cys Phe Glu Pro Cys
65                  70                  75                  80

His Asp Tyr Tyr Thr Ser Ala Ser Leu Phe Gly Ser Arg Pro Ile Arg
                85                  90                  95
```

```
Thr Thr Arg Arg His Arg Arg Leu Asn Arg Ala Ser Pro Ser Arg Glu
            100                 105                 110

Ala Met Ala Val Ala Leu Gln Pro Glu Gln Glu Val Thr Thr Lys Lys
        115                 120                 125

Lys Pro Ser Ile Lys Gln Arg Arg Val Val Thr Gly Met Gly Val
    130                 135                 140

Val Thr Pro Leu Gly His Asp Pro Asp Val Phe Tyr Asn Asn Leu Leu
145                 150                 155                 160

Asp Gly Thr Ser Gly Ile Ser Glu Ile Glu Thr Phe Asp Cys Ala Gln
                165                 170                 175

Phe Pro Thr Arg Ile Ala Gly Glu Ile Lys Ser Phe Ser Thr Asp Gly
            180                 185                 190

Trp Val Ala Pro Lys Leu Ser Lys Arg Met Asp Lys Phe Met Leu Tyr
        195                 200                 205

Met Leu Thr Ala Gly Lys Lys Ala Leu Thr Asp Gly Gly Ile Thr Glu
        210                 215                 220

Asp Val Met Lys Glu Leu Asp Lys Arg Lys Cys Gly Val Leu Ile Gly
225                 230                 235                 240

Ser Ala Met Gly Gly Met Lys Val Phe Asn Asp Ala Ile Glu Ala Leu
                245                 250                 255

Arg Ile Ser Tyr Lys Lys Met Asn Pro Phe Cys Val Pro Phe Ala Thr
            260                 265                 270

Thr Asn Met Gly Ser Ala Met Leu Ala Met Asp Leu Gly Trp Met Gly
        275                 280                 285

Pro Asn Tyr Ser Ile Ser Thr Ala Cys Ala Thr Ser Asn Phe Cys Ile
        290                 295                 300

Met Asn Ala Ala Asn His Ile Ile Arg Gly Glu Ala Asp Val Met Leu
305                 310                 315                 320

Cys Gly Gly Ser Asp Ala Val Ile Ile Pro Ile Gly Met Gly Gly Phe
                325                 330                 335

Val Ala Cys Arg Ala Leu Ser Gln Arg Asn Ser Asp Pro Thr Lys Ala
            340                 345                 350

Ser Arg Pro Trp Asp Ser Asn Arg Asp Gly Phe Val Met Gly Glu Gly
        355                 360                 365

Ala Gly Val Leu Leu Leu Glu Glu Leu Glu His Ala Lys Lys Arg Gly
        370                 375                 380

Ala Thr Ile Tyr Ala Glu Phe Leu Gly Gly Ser Phe Thr Cys Asp Ala
385                 390                 395                 400

Tyr His Met Thr Glu Pro His Pro Asp Gly Ala Gly Val Ile Leu Cys
                405                 410                 415

Ile Glu Lys Ala Leu Ala Gln Ser Gly Val Ser Arg Glu Asp Val Asn
            420                 425                 430

Tyr Ile Asn Ala His Ala Thr Ser Thr Pro Ala Gly Asp Ile Lys Glu
        435                 440                 445

Tyr Gln Ala Leu Ile His Cys Phe Gly Gln Asn Arg Glu Leu Lys Val
        450                 455                 460

Asn Ser Thr Lys Ser Met Ile Gly His Leu Leu Gly Ala Ala Gly Gly
465                 470                 475                 480

Val Glu Ala Val Ser Val Val Gln Ala Ile Arg Thr Gly Trp Ile His
                485                 490                 495

Pro Asn Ile Asn Leu Glu Asn Pro Asp Glu Gly Val Asp Thr Lys Leu
            500                 505                 510

Leu Val Gly Pro Lys Lys Glu Arg Leu Asn Val Lys Val Gly Leu Ser
```

Asn Ser Phe Gly Phe Gly Gly His Asn Ser Ser Ile Leu Phe Ala Pro
530                535                 540
Tyr Ile
545

<210> SEQ ID NO 15
<211> LENGTH: 2372
<212> TYPE: DNA
<213> ORGANISM: Cuphea pullcherrima
<220> FEATURE:
<221> NAME/KEY: misc_feature
<222> LOCATION: (1)...(2372)
<223> OTHER INFORMATION: n = A,T,C or G

<400> SEQUENCE: 15

| | | | | | |
|---|---|---|---|---|---|
| acntggtccg | gaattcccgg | gtcgacccac | gcgtccgcga | cgccaaccca | caccaaactt | 60 |
| cctcagcttc | tcttctcaag | acggacgcca | ttggcagcag | acagacagac | agacagaccc | 120 |
| ataaaagaga | gagagaggga | tccatcgaat | gcggccaccc | tcctttcatc | ttcgattcat | 180 |
| taccatacca | ttccgctgat | ccatttccg | ccttttccgg | gtctttcatc | ccaaagggta | 240 |
| tccttttcta | tcctatcttc | tcaaagggtc | agtcagttcc | ctccaatgcc | tgccgcctct | 300 |
| tccctgctcg | cttcccctct | ctgtacgtgg | ctccttgccg | cctgcatgtc | tacctccttc | 360 |
| caccccctccg | accctcttcc | gccttccatc | tcctctcctc | gccgacgcct | ctcccgccgc | 420 |
| cggattctct | cccaatgcgc | cccactacct | tctgcttcct | ccgccctccg | cggatccagt | 480 |
| ttccatacccc | tcgtcacctc | ttacctcgcc | tgcttcgagc | cctgccatga | ctactataca | 540 |
| tccgcatcct | tgttcggatc | cagacccatt | cgcaccaccc | gcaggcaccg | gaggctcaat | 600 |
| cgagcttccc | cttccagggg | aggcaatggc | cgtggctctg | caacctgaac | aggaagttac | 660 |
| cacaaagaag | aagccaagta | tcaaacagcg | gcgagtagtt | gtgactggaa | tgggtgtggt | 720 |
| gactcctcta | ggccatgaac | ctgatgtttt | tctacaataa | tctgcttgat | ggaacgagtg | 780 |
| gcataagcga | gatagagacc | tttgattgtg | ctcaatttcc | tacgagaatt | gctggagaga | 840 |
| tcaagtcttt | ctccacagat | ggttgggtgg | ccccgaagct | ctctaagagg | atggacaagt | 900 |
| tcatgctata | catgctgact | gctggcaaga | agcattaaac | agatggtgga | atcaccgaag | 960 |
| atgtgatgaa | agagctagat | aaaagaaaat | gcggagttct | cattggctca | gcaatgggtg | 1020 |
| gaatgaaggt | attcaatgat | gccattgaag | ccctaaggat | tcatataag | aagatgaatc | 1080 |
| ccttttgtgt | acctttcgct | accacaaata | tgggatcagc | tatgcttgca | atggacttgg | 1140 |
| gatggatggg | gcccaactac | tcgatatcta | ctgcttgtgc | aacgagtaac | ttttgtataa | 1200 |
| tgaatgctgc | gaaccatata | atcagaggcg | aagcagatgt | gatgctttgc | gggggctcag | 1260 |
| atgcggtaat | catacctatt | ggtatgggag | gttttgttgc | atgccgagct | ttgtcccaga | 1320 |
| gaaattccga | ccctactaaa | gcttcaagac | catgggacag | taatcgtgat | ggatttgtta | 1380 |
| tgggggaagg | agctggagtg | ctactactag | aggagttgga | gcatgcaaag | aaaagaggtg | 1440 |
| cgactatta | cgcagaattt | ctaggtggga | gtttcacttg | cgatgcctac | cacatgaccg | 1500 |
| agcctcaccc | tgatggagct | ggagtgattc | tctgcataga | gaaggctttg | gctcagtcag | 1560 |
| gagtctctag | ggaagacgta | aattacataa | atgcccatgc | cacatccact | ccggctggag | 1620 |
| atatcaaaga | gtaccaagct | cttatccact | gtttcggcca | aaacagagag | ttaaagttta | 1680 |
| attcaaccaa | atcaatgatt | ggtcaccttc | tcggagcagc | cggtggtgtg | gaagcagttt | 1740 |
| cagtagttca | ggcaataagg | actgggtgga | tccatccgaa | tattaatttg | gaaaacccag | 1800 |

```
atgaaggcgt ggatacaaaa ttgctcgtgg gtcctaagaa ggagagactg aacgttaagg      1860
tcggtttgtc taattcattt gggtttggtg ggcacaactc gtccatactc ttcgcccctt      1920
acatctagga cgtttcgtgt gtggaattct actcaacata tcaaagctga gttttgagg       1980 actccagcat gttggtagct ccttacgtct ctagacatgc ccatgagttt tgtgtccgga      2040
gctttagtcg gaaccatgac ggattgagta ctcatggcga cacttgatat actccttgct      2100
agaattgttg gtagagcaat attcattatc tcatattttt ttttctctg aaatctccct       2160 ccttgcaata gttgtacttt cgagcttttc atcgagtcag tgaagaagag aacaaagctg      2220
ttaactcggg cacgtagtaa ccatttgccc tttgttttgc tctctatttc atcaccgttt      2280
tgtggtttta aaatttgtaa aactagaaga ctggtttaga ttggtttgtt ttctcaaaaa      2340
aaaaaaaaaa gggcggccgc tctagaggat cc                                    2372
```

<210> SEQ ID NO 16
<211> LENGTH: 1580
<212> TYPE: DNA
<213> ORGANISM: Cuphea Hookeriana
<220> FEATURE:
<221> NAME/KEY: misc_feature
<222> LOCATION: (1)...(1580)
<223> OTHER INFORMATION: n = A,T,C or G

<400> SEQUENCE: 16

```
cctgaatcgg attcaagaga gagtttcgtt gctgggatgg cgaatgcatc tgggtttctg        60
ggttcttcag ttcctgccct gagaagggca actcagcatt cgatttcatc gtctcgtgga       120
tcttcctcgg agtttgtctc caaaaggtg ttttgctgta gtgccgttca ggattctgac        180
aggcagtctt tgggtgattc tcgctcgccg aggcttgtga gtagaggatg caaattaatt       240
ggatctggtt ctgctatacc agctcttcaa gtctcaaatg atgatcttgc taaaattgtc       300
gacaccaatg atgaatggat tactgtccga acggggatcc gcaaccgaag ggttctctca       360
ggtaaagata gtcttacaaa tttagcatca gaggcagcaa ggaaagctct agagatggca      420
caggtagacg caaatgatgt ggatatggtt tgatgtgta cttctacccc tgaggacctt       480
ttcggcagtg ctcctcagat atcgaaagca cttggctgca aaaagaatcc tttgtcttac      540
gacattaccg ctgcatgcag tggatttgtg ttgggtttag tctcagctgc ttgccacatt      600
agaggtgggg gttttaacaa tattctagtg attggtgctg attctctttc tcggtatgtt      660
gactggaccg atcgggaac atgtattctc tttggagatg ctgctggagc tgtagtggtg       720
cagtcatgtg atgctgagga agatgggctc tttgcttttg atttgcatag cgatggagat      780
gggcaaaggc atctaaaagc tgcaatcaaa gaagatgaag ttgataaagc cctgggacat      840
aatgggtcca tcagagattt tccaccaagg cgttcttcat actcttgcat ccaaatgaac      900
ggtaaagagg tattccgctt tgcttgccgc tctgtgcctc agtcaatcga atcagcactt      960
ggaaaggccg gtcttaatgg atccaacatc gactggttgc tgcttcatca ggcaaatcag     1020
aggatcattg atgcagtagc aacacgtcta gaggttcctc aagaacgaat tatctcaaac     1080
ttggcaaatt acgggaacac tagtgcggca tccattccct ggcactaga cgaagctgtg     1140 aggagtggaa atgtgaagcc gggtcacgtg attgcaaccg caggatttgg cgccggactc     1200
acatggggtt ctgctattat caggtgggga taagactgaa gccgagccag cactgcagct     1260
tcctctcaaa ccgatgtttc acgaaatttt gcttccatga ccanaaaaag aagaagtcag    1320
tcttttatgg agcaagcaac acgacacgat cttcatcaca ttgcccttttt tcgttcccct    1380
```

-continued

| | |
|---|---|
| tttccattag tttgatgatt ttgctgacaa tacaataccc atagtttctt ttgtccccaa | 1440 |
| taagttattt gtttcttgtt taattgttca gcttttactt cattttgtct cgggacattg | 1500 |
| gagatgacag cataaacatc atgtttatat tttgctaaaa aaaaaaaaaa aaaaaaaaa | 1560 |
| aaaaaaaaaa aaaaaaaaa | 1580 |

<210> SEQ ID NO 17
<211> LENGTH: 382
<212> TYPE: PRT
<213> ORGANISM: Cuphea Hookeriana

<400> SEQUENCE: 17

```
Met Ala Asn Ala Ser Gly Phe Leu Gly Ser Ser Val Pro Ala Leu Arg
  1               5                  10                  15

Arg Ala Thr Gln His Ser Ile Ser Ser Arg Gly Ser Ser Ser Glu
             20                  25                  30

Phe Val Ser Lys Arg Val Phe Cys Cys Ser Ala Val Gln Asp Ser Asp
         35                  40                  45

Arg Gln Ser Leu Gly Asp Ser Arg Ser Pro Arg Leu Val Ser Arg Gly
     50                  55                  60

Cys Lys Leu Ile Gly Ser Gly Ser Ala Ile Pro Ala Leu Gln Val Ser
 65                  70                  75                  80

Asn Asp Asp Leu Ala Lys Ile Val Asp Thr Asn Asp Glu Trp Ile Thr
                 85                  90                  95

Val Arg Thr Gly Ile Arg Asn Arg Val Leu Ser Gly Lys Asp Ser
            100                 105                 110

Leu Thr Asn Leu Ala Ser Glu Ala Ala Arg Lys Ala Leu Glu Met Ala
        115                 120                 125

Gln Val Asp Ala Asn Asp Val Asp Met Val Leu Met Cys Thr Ser Thr
    130                 135                 140

Pro Glu Asp Leu Phe Gly Ser Ala Pro Gln Ile Ser Lys Ala Leu Gly
145                 150                 155                 160

Cys Lys Lys Asn Pro Leu Ser Tyr Asp Ile Thr Ala Ala Cys Ser Gly
                165                 170                 175

Phe Val Leu Gly Leu Val Ser Ala Ala Cys His Ile Arg Gly Gly Gly
            180                 185                 190

Phe Asn Asn Ile Leu Val Ile Gly Ala Asp Ser Leu Ser Arg Tyr Val
        195                 200                 205

Asp Trp Thr Asp Arg Gly Thr Cys Ile Leu Phe Gly Asp Ala Ala Gly
    210                 215                 220

Ala Val Val Gln Ser Cys Asp Ala Glu Glu Asp Gly Leu Phe Ala
225                 230                 235                 240

Phe Asp Leu His Ser Asp Gly Asp Gly Gln Arg His Leu Lys Ala Ala
                245                 250                 255

Ile Lys Glu Asp Glu Val Asp Lys Ala Leu Gly His Asn Gly Ser Ile
            260                 265                 270

Arg Asp Phe Pro Pro Arg Arg Ser Ser Tyr Ser Cys Ile Gln Met Asn
        275                 280                 285

Gly Lys Glu Val Phe Arg Phe Ala Cys Arg Ser Val Pro Gln Ser Ile
    290                 295                 300

Glu Ser Ala Leu Gly Lys Ala Gly Leu Asn Gly Ser Asn Ile Asp Trp
305                 310                 315                 320

Leu Leu Leu His Gln Ala Asn Gln Arg Ile Ile Asp Ala Val Ala Thr
                325                 330                 335
```

-continued

```
Arg Leu Glu Val Pro Gln Glu Arg Ile Ile Ser Asn Leu Ala Asn Tyr
            340                 345                 350

Gly Asn Thr Ser Ala Ala Pro Gly His Val Ile Ala Thr Ala Gly Phe
            355                 360                 365

Gly Ala Gly Leu Thr Trp Gly Ser Ala Ile Ile Arg Trp Gly
    370                 375                 380
```

PLANT FATTY ACID SYNTHASES AND USE IN IMPROVED METHODS FOR PRODUCTION OF MEDIUM-CHAIN FATTY ACIDS

CROSS REFERENCE TO RELATED APPLICATIONS

This application claims the benefit of priority to provisional application serial no. 60/041,815, filed on Apr. 11, 1997.

INTRODUCTION

1. Field of Invention

The present invention is directed to genes encoding plant fatty acid synthase enzymes relevant to fatty acid synthesis in plants, and to methods of using such genes in combination with genes encoding plant medium-chain preferring thioesterase proteins. Such uses provide a method to increase the levels of medium-chain fatty acids that may be produced in seed oils of transgenic plants.

2. Background

Higher plants synthesize fatty acids via a common metabolic pathway. In developing seeds, where fatty acids attached to triglycerides are stored as a source of energy for further germination, the fatty acid synthesis pathway is located in the plastids. The first step is the formation of acetyl-ACP (acyl carrier protein) from acetyl-CoA and ACP catalyzed by a short chain preferring condensing enzyme, β-ketoacyl-ACP synthase (KAS) III. Elongation of acetyl-ACP to 16- and 18-carbon fatty acids involves the cyclical action of the following sequence of reactions: condensation with a two-carbon unit from malonyl-ACP to form a longer β-ketoacyl-ACP (β-ketoacyl-ACP synthase), reduction of the keto-function to an alcohol (β-ketoacyl-ACP reductase), dehydration to form an enoyl-ACP (β-hydroxyacyl-ACP dehydrase), and finally reduction of the enoyl-ACP to form the elongated saturated acyl-ACP (enoyl-ACP reductase). β-ketoacyl-ACP synthase I (KAS I), is primarily responsible for elongation up to palmitoyl-ACP (C16:0), whereas β-ketoacyl-ACP synthase II (KAS II) is predominantly responsible for the final elongation to stearoyl-ACP (C18:0).

Genes encoding peptide components of β-ketoacyl-ACP synthases I and II have been cloned from a number of higher plant species, including castor (*Ricinus communis*) and Brassica species (U.S. Pat. No. 5,510,255). KAS I activity was associated with a single synthase protein factor having an approximate molecular weight of 50 kD (synthase factor B) and KAS II activity was associated with a combination of two synthase protein factors, the 50 kD synthase factor B and a 46 kd protein designated synthase factor A. Cloning and sequence of a plant gene encoding a KAS III protein has been reported by Tai and Jaworski (*Plant Physiol.* (1993) 103:1361–1367).

The end products of plant fatty acid synthetase activities are usually 16- and 18-carbon fatty acids. There are, however, several plant families that store large amounts of 8- to 14-carbon (medium-chain) fatty acids in their oilseeds. Recent studies with *Umbellularia californica* (California bay), a plant that produces seed oil rich in lauric acid (12:0), have demonstrated the existence of a medium-chain-specific isozyme of acyl-ACP thioesterase in the seed plastids. Subsequent purification of the 12:0-ACP thioesterase from *Umbellularia californica* led to the cloning of a thioesterase cDNA which was expressed in seeds of Arabidopsis and Brassica resulting in a substantial accumulation of lauric acid in the triglyceride pools of these transgenic seeds (U.S. Pat. No. 5,512,482). These results and subsequent studies with medium-chain thioesterases from other plant species have confirmed the chain-length-determining role of acyl-ACP thioesterases during de novo fatty acid biosynthesis (T. Voelker (1996) *Genetic Engineering,* Ed. J. K. Setlow, Vol. 18, pgs. 111–133).

DESCRIPTION OF THE FIGURES

FIG. 1. DNA (SEQ ID NO: 1) and translated amino acid sequence (SEQ ID NO:2) of *Cuphea hookeriana* KAS factor B clone chKAS B-2 are provided.

FIG. 2. DNA (SEQ ID NO: 3) and translated amino acid sequence (SEQ ID NO:4) of *Cuphea hookeriana* KAS factor B clone chKAS B-31-7 are provided.

FIG. 3. DNA (SEQ ID NO:5) and translated amino acid sequence (SEQ ID NO:6) of *Cuphea hookeriana* KAS factor A clone chKAS A-2-7 are provided.

FIG. 4. DNA (SEQ ID NO:7) and translated amino acid sequence (SEQ ID NO:8) of *Cuphea hookeriana* KAS factor A clone chKAS A-1-6 are provided.

FIG. 5. DNA (SEQ ID NO:9) and translated amino acid sequence (SEQ ID NO: 10) of *Cuphea pullcherrima* KAS factor B clone cpuKAS B/7-8 are provided.

FIG. 6. DNA (SEQ ID NO: 11) and translated amino acid sequence (SEQ ID NO:12) of *Cuphea pullcherrima* KAS factor B clone cpuKAS B/8-7A are provided.

FIG. 7. DNA (SEQ ID NO: 13) and translated amino acid sequence (SEQ ID NO:14) of *Cuphea pullcherrima* KAS factor A clone cpuKAS A/p7-6A are provided.

FIG. 8. Preliminary DNA sequence (SEQ ID NO:15) of *Cuphea pullcherrima* KAS factor A clone cpuKAS A/p8-9A is provided.

FIG. 9. DNA (SEQ ID NO:16) and translated amino acid sequence (SEQ ID NO:17) of *Cuphea hookeriana* KASIII clone chKASIII-27 are provided.

FIG. 19C. Graph showing the %C12:0 in transgenic plants resulting from cross of plants containing Uc FatB1 (LA86DH186) and lines expressing Ch KAS A-2-7 is provided.

SUMMARY OF THE INVENTION

Figure 10:
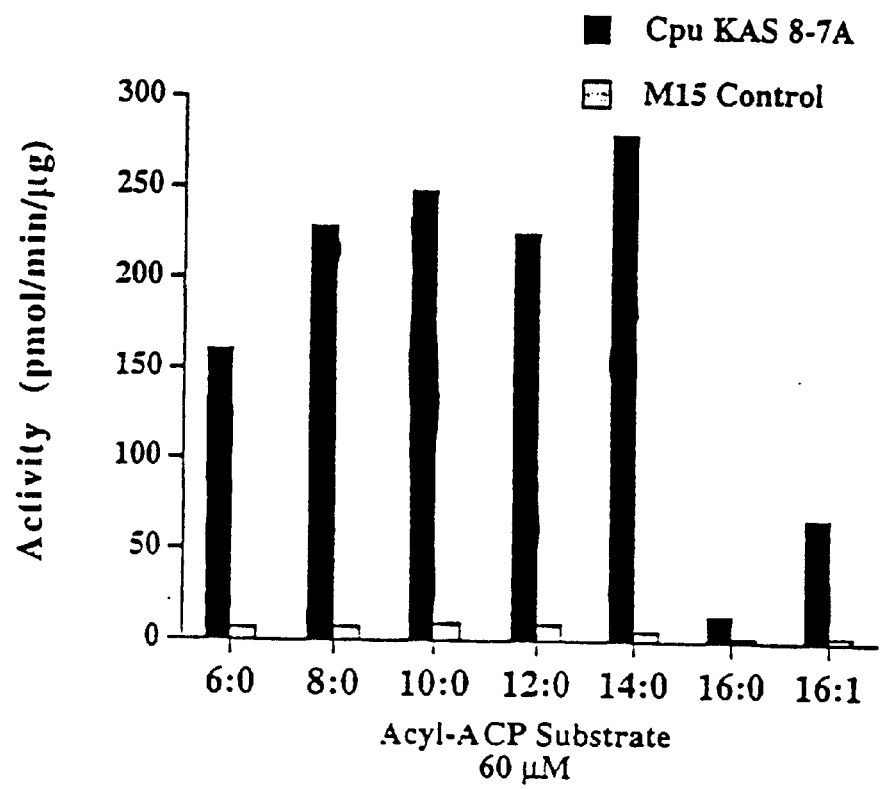
FIG. 10. The activity profile for purified cpuKAS B/8-7A using various acyl-ACP substrates is provided.

By this invention, compositions and methods of use related to β-ketoacyl-ACP synthase (KAS) are provided. Also of interest are methods and compositions of amino acid and nucleic acid sequences related to biologically active plant synthase(s).

In particular, genes encoding KAS protein factors A and B from Cuphea species are provided. The KAS genes are of interest for use in a variety of applications, and may be used to provide synthase I and/or synthase II activities in transformed host cells, including bacterial cells, such as $E.\ coli$, and plant cells. Synthase activities are distinguished by the preferential activity towards longer and shorter acyl-ACPs as well as by the sensitivity towards the KAS specific inhibitor, cerulenin. Synthase protein preparations having preferential activity towards medium chain length acyl-ACPs are synthase I-type or KAS I. The KAS I class is sensitive to inhibition by cerulenin at concentrations as low as 1 $\mu$M. Synthases having preferential activity towards longer chain length acyl-ACPs are synthase II-type or KAS II. The KAS enzymes of the II-type are also sensitive to cerulenin, but at higher concentrations (50 $\mu$M). Synthase III-type enzymes have preferential activity towards short chain length acyl-ACPs and are insensitive to cerulenin inhibition.

Nucleic acid sequences encoding a synthase protein may be employed in nucleic acid constructs to modulate the amount of synthase activity present in the host cell, especially the relative amounts of synthase I-type, synthase II-type and synthase III-type activity when the host cell is a plant host cell. In addition, nucleic acid constructs may be designed to decrease expression of endogenous synthase in a plant cell as well. One example is the use of an anti-sense synthase sequence under the control of a promoter capable of expression in at least those plant cells which normally produce the enzyme.

Of particular interest in the present invention is the coordinate expression of a synthase protein with the expression of thioesterase proteins. For example, coordinated expression of synthase factor A and a medium-chain thioesterase provides a method for increasing the level of medium-chain fatty acids which may be harvested from transgenic plant seeds. Furthermore, coordinated expression of a synthase factor A gene with plant medium-chain thioesterase proteins also provides a method by which the ratios of various medium-chain fatty acids produced in a transgenic plant may be modified. For example, by expression of a synthase factor A, it is possible to increase the ratio of C10/C8 fatty acids which are produced in plant seed oils as the result of expression of a thioesterase having activity on C8 and C10 fatty acids.

DETAILED DESCRIPTION OF THE INVENTION

A plant synthase factor protein of this invention includes a sequence of amino acids or polypeptide which is required for catalyzation of a condensation reaction between an acyl-ACP having a chain length of $C_2$ to $C_{16}$ and malonyl-ACP in a plant host cell. A particular plant synthase factor protein may be capable of catalyzing a synthase reaction in a plant host cell (for example as a monomer or homodimer) or may be one component of a multiple peptide enzyme which is capable of catalyzing a synthase reaction in a plant host cell, i.e. one peptide of a heterodimer.

Synthase I (KAS I) demonstrates preferential activity towards acyl-ACPs having shorter carbon chains, $C_2$–$C_{14}$ and is sensitive to inhibition by cerulenin at concentrations of 1 $\mu$M. Synthase II (KAS II) demonstrates preferential activity towards acyl-ACPs having longer carbon chains, $C_{14}$–$C_{16}$, and is inhibited by concentrations of cerulenin (50 $\mu$M). Synthase III demonstrates preferential activity towards acyl-CoAs having very short carbon chains, $C_2$ to $C_6$, and is insensitive to inhibition by cerulenin.

Synthase factors A and B, and synthase III proteins obtained from medium-chain fatty acid producing plant species of the genus Cuphea are described herein. As described in the following Examples, synthase A from C. hookeriana is naturally expressed at a high level and only in the seeds. C. hookeriana synthase B is expressed at low levels in all tissues examined. Expression of synthase A and synthase B factors in $E.\ coli$ and purification of the resulting proteins is employed to determine activity of the various synthase factors. Results of these analyses indicate that synthase factor A from Cuphea hookeriana has the greatest activity on 6:0-ACP substrates, whereas synthase factor B from Cuphea pullcherrima has greatest activity on 14:0-ACP. Similar studies with synthase factors A and B from castor demonstrate similar activity profiles between the factor B synthase proteins from Cuphea and castor. The synthase A clone from castor, however, demonstrates a preference for 14:0-ACP substrate.

Expression of a *Cuphea hookeriana* KAS A protein in transgenic plant seeds which normally do not produce medium-chain fatty acids does not result in any detectable modification of the fatty acid types and contents produced in such seeds. However, when *Cuphea hookeriana* KAS A protein is expressed in conjunction with expression of a medium-chain acyl-ACP thioesterase capable of providing for production of C8 and C10 fatty acids in plant seed oils, increases in the levels of medium-chain fatty acids over the levels obtainable by expression of the medium-chain thioesterase alone are observed. In addition, where significant amounts of C8 and C10 fatty acids are produced as the result of medium-chain thioesterase expression, co-expression of a Cuphea KAS A protein also results in an alteration of the proportion of the C8 and C10 fatty acids that are obtained. For example, an increased proportion of C10 fatty acids may be obtained by co-expression of *Cuphea hookeriana* ChFatB2 thioesterase and a chKAS A synthase factor proteins.

Furthermore, when *Cuphea hookeriana* KAS A protein is expressed in conjunction with expression of a medium-chain acyl-ACP thioesterase capable of providing for production of C12 fatty acids in plant seed oils, increases in the levels of medium-chain fatty acids over the levels obtainable by expression of the medium-chain thioesterase alone are also observed. In addition, where significant amounts of C12 and C14 fatty acids are produced as the result of medium-chain thioesterase expression, co-expression of a Cuphea KAS A protein also results in an alteration of the proportion of the C12 and C14 fatty acids that are obtained. For example, an increased proportion of C12 fatty acids may be obtained by co-expression of Uc FatB1 thioesterase and a chKAS A synthase factor proteins.

However, when *Cuphea hookeriana* KAS A protein is expressed in conjunction with the expression of a long-chain acyl-ACP thioesterase capable of providing for production of C18 and C18:1 fatty acids in plant seed oils, no effect on the production of long chain fatty acids was observed. Furthermore, when plants transformed to express a long chain acyl-ACP thioesterase from mangosteen (GarmFatA1, U.S. patent application Ser. No. 08/440,845), which preferentially hydrolyzes C18:0 and C18:1 fatty acyl-ACPs, are crossed with nontransformed control plants, a significant reduction in the levels of C18:0 is obtained. Similar reductions are also observed in the levels of C18:0 in the seeds of plants resulting from crosses between plants transformed to express the GarmFatA1 and plants expressing the *Cuphea hookeriana* KAS A protein.

Thus, the instant invention provides methods of increasing and/or altering the medium-chain fatty acid compositions in transgenic plant seed oils by co-expression of medium-chain acyl-ACP thioesterases with synthase factor proteins. Furthermore, various combinations of synthase factors and medium-chain thioesterases may be achieved depending upon the particular fatty acids desired. For example, for increased production of C14 fatty acids, synthase protein factors may be expressed in combination with a C14 thioesterase, for example from *Cuphea palustris* or nutmeg may be employed (WO 96/23892). In addition, thioesterase expression may be combined with a number of different synthase factor proteins for additional effects on medium-chain fatty acid composition.

Synthases of use in the present invention include modified amino acid sequences, such as sequences which have been mutated, truncated, increased and the like, as well as such sequences which are partially or wholly artificially synthesized. The synthase protein encoding sequences provided herein may be employed in probes for further screening or used in genetic engineering constructs for transcription or transcription and translation in host cells, especially plant host cells. One skilled in the art will readily recognize that antibody preparations, nucleic acid probes (DNA and RNA) and the like may be prepared and used to screen and recover synthases and/or synthase nucleic acid sequences from other sources. Typically, a homologously related nucleic acid sequence will show at least about 60% homology, and more preferably at least about 70% homology, between the *R. communis* synthase and the given plant synthase of interest, excluding any deletions which may be present. Homology is determined upon comparison of sequence information, nucleic acid or amino acid, or through hybridization reactions.

Recombinant constructs containing a nucleic acid sequence encoding a synthase protein factor or nucleic acid sequences encoding a synthase protein factor and a medium-chain acyl-ACP thioesterase may be prepared by methods well known in the art. Constructs may be designed to produce synthase in either prokaryotic or eukaryotic cells. The increased expression of a synthase in a plant cell, particularly in conjunction with expression of medium-chain thioesterases, or decreasing the amount of endogenous synthase observed in plant cells are of special interest.

Synthase protein factors may be used, alone or in combination, to catalyze the elongating condensation reactions of fatty acid synthesis depending upon the desired result. For example, rate influencing synthase activity may reside in synthase I-type, synthase II-type, synthase III-type or in a combination of these enzymes. Furthermore, synthase activities may rely on a combination of the various synthase factors described herein.

Constructs which contain elements to provide the transcription and translation of a nucleic acid sequence of interest in a host cell are “expression cassettes”. Depending upon the host, the regulatory regions will vary, including regions from structural genes from viruses, plasmid or chromosomal genes, or the like. For expression in prokaryotic or eukaryotic microorganisms, particularly unicellular hosts, a wide variety of constitutive or regulatable promoters may be employed. Among transcriptional initiation regions which have been described are regions from bacterial and yeast hosts, such as *E. coli, B. subtilis, Saccharomyces cerevisiae,* including genes such as β-galactosidase, T7 polymerase, trp-lac (tac), trp E and the like.

An expression cassette for expression of synthase in a plant cell will include, in the 5' to 3' direction of transcription, a transcription and translation initiation control regulatory region (also known as a “promoter”) functional in a plant cell, a nucleic acid sequence encoding a synthase, and a transcription termination region. Numerous transcription initiation regions are available which provide for a wide variety of constitutive or regulatable, e.g., inducible, transcription of the desaturase structural gene. Among transcriptional initiation regions used for plants are such regions associated with cauliflower mosaic viruses (35S, 19S), and structural genes such as for nopaline synthase or mannopine synthase or napin and ACP promoters, etc. The transcription/translation initiation regions corresponding to such structural genes are found immediately 5' upstream to the respective start codons. Thus, depending upon the intended use, different promoters may be desired.

Of special interest in this invention are the use of promoters which are capable of preferentially expressing the synthase in seed tissue, in particular, at early stages of seed oil formation. Examples of such seed-specific promoters include the region immediately 5' upstream of a napin or seed ACP genes such as described in U.S. Pat. No. 5,420,034, desaturase genes such as described in Thompson et al (*Proc. Nat. Acad. Sci.* (1991) 88:2578–2582), or a Bce-4 gene such as described in U.S. Pat. No. 5,530,194. Alternatively, the use of the 5' regulatory region associated with the plant synthase structural gene, i.e., the region immediately 5' upstream to a plant synthase structural gene and/or the transcription termination regions found immediately 3' downstream to the plant synthase structural gene, may often be desired. In general, promoters will be selected based upon their expression profile which may change given the particular application.

In addition, one may choose to provide for the transcription or transcription and translation of one or more other sequences of interest in concert with the expression or anti-sense of the synthase sequence, particularly medium-chain plant thioesterases such as described in U.S. Pat. No. 5,512,482, to affect alterations in the amounts and/or composition of plant oils.

When one wishes to provide a plant transformed for the combined effect of more than one nucleic acid sequence of interest, a separate nucleic acid construct may be provided for each or the constructs may both be present on the same plant transformation construct. The constructs may be introduced into the host cells by the same or different methods, including the introduction of such a trait by crossing transgenic plants via traditional plant breeding methods, so long as the resulting product is a plant having both characteristics integrated into its genome.

Normally, included with the DNA construct will be a structural gene having the necessary regulatory regions for expression in a host and providing for selection of transformed cells. The gene may provide for resistance to a cytotoxic agent, e.g. antibiotic, heavy metal, toxin, etc., complementation providing prototrophy to an auxotrophic host, viral immunity or the like. Depending upon the number of different host species into which the expression construct or components thereof are introduced, one or more markers may be employed, where different conditions for selection are used for the different hosts.

The manner in which the DNA construct is introduced into the plant host is not critical to this invention. Any method which provides for efficient transformation may be employed. Various methods for plant cell transformation include the use of Ti- or Ri-plasmids, microinjection, electroporation, liposome fusion, DNA bombardment or the like. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation.

The expression constructs may be employed with a wide variety of plant life, particularly plant life involved in the production of vegetable oils. These plants include, but are not limited to rapeseed, peanut, sunflower, safflower, cotton, soybean, corn and oilseed palm.

For transformation of plant cells using Agrobacterium, explants may be combined and incubated with the transformed Agrobacterium for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

The invention now being generally described, it will be more readily understood by reference to the following examples which are included for purposes of illustration only and are not intended to limit the present invention.

EXAMPLES

Example 1
Cuphea KAS Factor A and B Gene Cloning

Total RNA isolated from developing seeds of *Cuphea hookeriana* and *Cuphea pullcherrima* was used for cDNA synthesis in commercial l-based cloning vectors. For cloning each type of KAS gene, approximately 400,000–500,000 unamplified recombinant phage were plated and the plaques transferred to nitrocellulose. For KAS factor B cloning from *C. hookeriana*, a mixed probe containing *Brassica napus* KAS factor B and *Ricinus communis* (Castor) KAS factor B radiolabeled cDNA's was used. Similarly, a mixed probe containing *Brassica napus* KAS factor A and *Ricinus communis* KAS factor A cDNA clones was used to obtain *C. hookeriana* KAS factor A genes. For KASIII, a spinach KASIII cDNA clone obtained from Dr. Jan Jaworski was radiolabeled and used as a probe to isolate a KASIII clone from *C. hookeriana*. For KAS B and KAS A cloning from *C. pullcherrima*, *C. hookeriana* KAS B and KAS A genes chKAS B-2 and chKAS A-2-7 (see below) were radiolabeled and used as probes.

DNA sequence and translated amino acid sequence for Cuphea KAS clones are provided in FIGS. 1–9. *Cuphea hookeriana* KAS factor B clones chKAS B-2 and chKAS B-31-7 are provided in FIGS. 1 and 2. Neither of the clones is full length. *Cuphea hookeriana* KAS Factor A clones chKAS A-2-7 and chKAS A-1-6 are provided in FIGS. 3 and 4. chKAS A-2-7 contains the entire encoding sequence for the KAS factor protein. Based on comparison with other plant synthase proteins, the transit peptide is believed to be represented in the amino acids encoded by nucleotides 125–466. chKAS A-1-6 is not a full length clone although some transit peptide encoding sequence is present. Nucleotides 1–180 represent transit peptide encoding sequence, and the mature protein encoding sequence is believed to begin at nucleotide 181.

*Cuphea pullcherrima* KAS factor B clones cpuKAS B/7-8 and cpuKAS B/8-7A are provided in FIGS. 5 and 6. Both of the clones contain the entire encoding sequences for the KAS factor B proteins. The first 35 amino acids of cpuKAS B/7-8 are believed to represent the transit peptide, with the mature protein encoding sequence beginning at nucleotide 233. The first 39 amino acids of cpuKAS B/8-7A are believed to represent the transit peptide, with the mature protein encoding sequence beginning at nucleotide 209. *Cuphea pullcherrima* KAS factor A clones cpuKAS A/p7-6A and cpuKAS A-p8-9A are provided in FIGS. 7 and 8. Both of the clones contain the entire encoding sequences for the KAS factor A proteins. Translated amino acid sequence of cpuKAS A/p7-6A is provided. The mature protein is believed to begin at the lysine residue encoded 595–597, and the first 126 amino acids are believed to represent the transit peptide. The DNA sequence of KAS A clone cpuKAS Ap-8-9A is preliminary. Further analysis will be conducted to determine final DNA sequence and reveal the amino acid sequence encoded by this gene.

DNA and translated amino acid sequence of *Cuphea hookeriana* KASIII clone chKASIII-27 is provided in FIG. 9. The encoding sequence from nucleotides 37-144 of chKASIII-27 are believed to encode a transit peptide, and the presumed mature protein encoding sequence is from nucleotides 145–1233.

Deduced amino acid sequence of the *C. hookeriana* KAS factor B and KAS factor A cDNA's reveals strong homology to the *Brassica napus* and *Ricinus communis* clones previously reported. The *C. hookeriana* KAS factor B clone is more homologous to the Ricinus and Brassica KAS factor B clones (94% and 91% respectively) than it is to the Ricinus and Brassica KAS factor A clones (60% for both). Furthermore, the *C. hookeriana* KAS factor A clone is more homologous to the Ricinus and Brassica KAS factor A clones (85% and 82% respectively) than it is the Ricinus and Brassica KAS factor B clone (60% for both). The *C. hookeriana* KAS factor B cDNAs designated as chKAS B-2 and chKAS B-31-7 are 96% identical within the mature portion of the polypeptide. Similarly, the deduced amino acid sequence of the mature protein regions of the *C. hookeriana* KAS factor A clones chKAS A-2-7 and chKAS A-1-6 are 96% identical. The *C. pullcherrima* KAS clones also demonstrate homology to the *R. communis* and *Brassica napus* KAS clones. The mature protein portion of all of the KAS factor A family members in the different Cuphea species are 95% identical. Similarly the mature protein portion of the KAS factor B genes in Cuphea are also 95–97% identical with each other. However there is only approximately 60% sequence identity between KAS factor B and KAS factor A clones either within the same or different species of Cuphea.

Example 2
Levels and Patterns of Expression

To examine tissue specificity of KAS expression in *Cuphea hookeriana*, Northern blot analysis was conducted using total RNA isolated from seed, root, leaf and flower tissue. Two separate but identical blots were hybridized with either chKAS B-31-7 or chKAS A-2-7 coding region probes. The data from this RNA blot analysis indicate that KAS B is expressed at a similar level in all tissues examined, whereas KAS A expression is detected only in the seed. These results also demonstrate a different level of expression for each of the syntheses. KAS A is an abundant message, whereas KAS B is expressed at low levels. Furthermore, even under highly stringent hybridization conditions (65_C, 0.1×SSC, 0.5% SDS), the KAS A probe hybridizes equally well with two seed transcripts of 2.3 and 1.9 kb. The larger hybridizing band is likely the transcript of the KAS A-2-7 gene since the size of its cDNA is 2046 bp, and the number of clones obtained from cDNA screening corresponds well with the apparent mobility of the mRNA and its abundance on the blot.

Example 3
Expression of Plant KAS Genes in *E. coli*

DNA fragments encoding the mature polypeptide of the *Cuphea hookeriana* KAS A cDNAs and the *Cuphea pullcherrima* KAS B cDNAs were obtained by PCR and cloned into a QIAexpress expression vector (Qiagene). Experimental conditions for maximum level of expression were determined for all of these clones and the parameters for highest level of soluble fraction were identified. Cells are grown in ECLB media containing 1M sorbitol and 2.5 mM betaine overnight and subcultured as a 1:4 dilution in the same medium. Cells are then grown for 2 hours (to approximately 0.6–0.8 O.D.) and induced with 0.4 mM IPTG and allowed to grow for 5 more hours.

Enzyme activity of the affinity purified recombinant enzymes obtained from over-expression of the chKAS A-2-7 and cpuKAS B/8-7A clones was measured using a wide range of acyl-ACP substrates (6:0- to 16:1-ACP). The activity profile for cpuKAS B/8-7A is provided in FIG. 10. The data demonstrate that the enzyme is active with all acyl-ACP substrates examined, although activity on 6:0 to 14:0-ACP substrates is substantially greater than the activity on 16:0 and 16:1 substrates.

Figure 11:
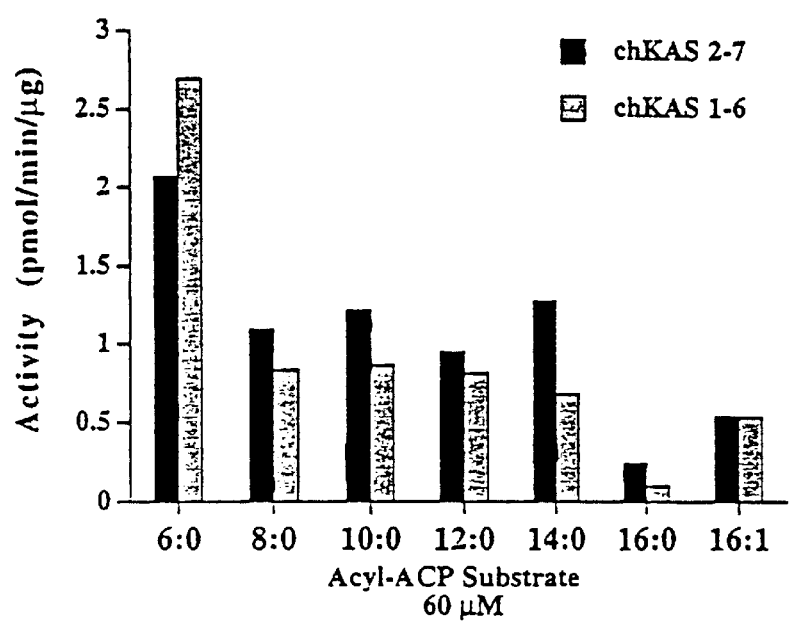
FIG. 11. The activity profile for purified chKAS A-2-7 and chKAS A-1-6 using various acyl-ACP substrates is provided.

The activity profile of the *C. hookeriana* KAS A clones chKAS A-2-7 and chKAS A-1-6 is provided in FIG. 11. The *C. hookeriana* KAS A clones are most active with C:6, and have the least activity with C:16:0 substrates. However, the activity of this clone on even the preferred C6:0 substrate is 50 fold lower than the activity of the *C. pullcherrima* KAS B clones.

Figure 12:
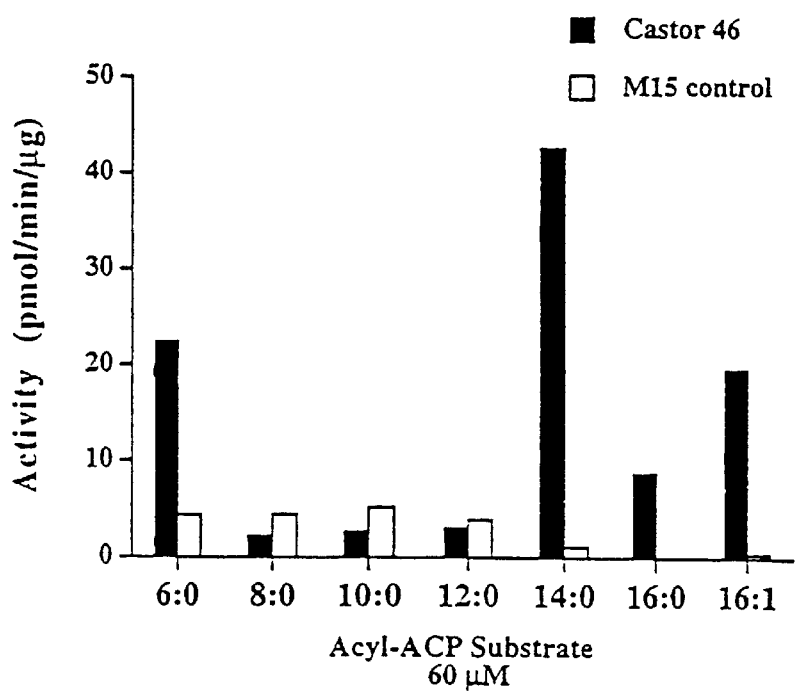
FIG. 12. The activity profile for purified castor KAS factor A using various acyl-ACP substrates is provided.
Figure 13:
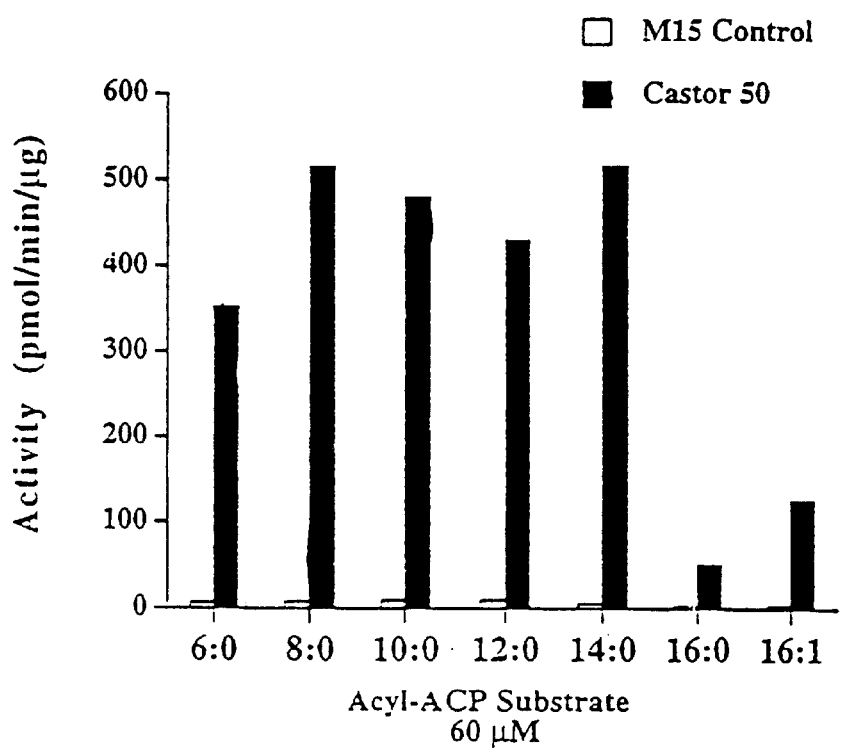
FIG. 13. The activity profile for purified castor KAS factor B using various acyl-ACP substrates is provided.

A fragment containing the mature protein encoding portion of a *R. communis* KAS factor A clone was also cloned into a QIAexpress expression vector, expressed in *E. coli* and the enzyme affinity purified as described above. The activity profile for castor KAS A is provided in FIG. 12. Highest activity is observed with C14:0 substrates, although some activity is also seen with C6:0 and C16:1. In comparison, the activity profile obtained from purified *R. communis* KAS factor B also using the QIAexpress expression system is provided in FIG. 13. The KAS B clone demonstrates substantially higher levels of activity (10 fold and higher) than the *R. communis* KAS A clone. The preference of the KAS factor B for 6:0- to 14:0-ACP substrates is consistent with the previous observations that this protein provides KAS I activity.

Example 4
KAS and TE Expression in Transgenic Seed

Both the CpFatB1 (*C. hookeriana* thioesterase cDNA; Dehesh et al. (1996) *Plant Physiol.* 110:203–210) and the chKAS A-2-7 were PCR amplified, sequenced, and cloned into a napin expression cassette. The napin/cp FatB1 and the napin/KAS A-2-7 fusions were ligated separately into the binary vector pCGN1558 (McBride and Summerfelt (*Pl.Mol.Biol.* (1990) 14:269–276) and transformed into *A. tumefaciens*, EHA101. The resulting cpFatB1 binary construct is pCGN5400 and the chKAS A-2-7 construct is pCGN5401. Agrobacterium mediated transformation of a *Brassica napus* canola variety was carried out as described by Radke et al. (*Theor. Appl. Genet.* (1988) 75:685–694; *Plant Cell Reports* (1992) 11:499–505). Several transgenic events were produced for each of the pCGN5400 and pCGN5401 constructs.

A double gene construct containing a napin/cpFatB1 expression construct in combination with a napin/chKAS A-2-7 expression construct was also assembled, ligated into a binary vector and used for co-cultivation of a canola Brassica variety. The binary construct containing the chFatB1 and chKAS A-2-7 expression constructs is pCGN5413.

Fatty acid analysis of 26 transgenic lines containing chKAS A-2-7 (5401 lines) showed no significant changes in the oil content or profile as compared to similar analyses of wild type canola seeds of the transformed variety.

Figure 14:
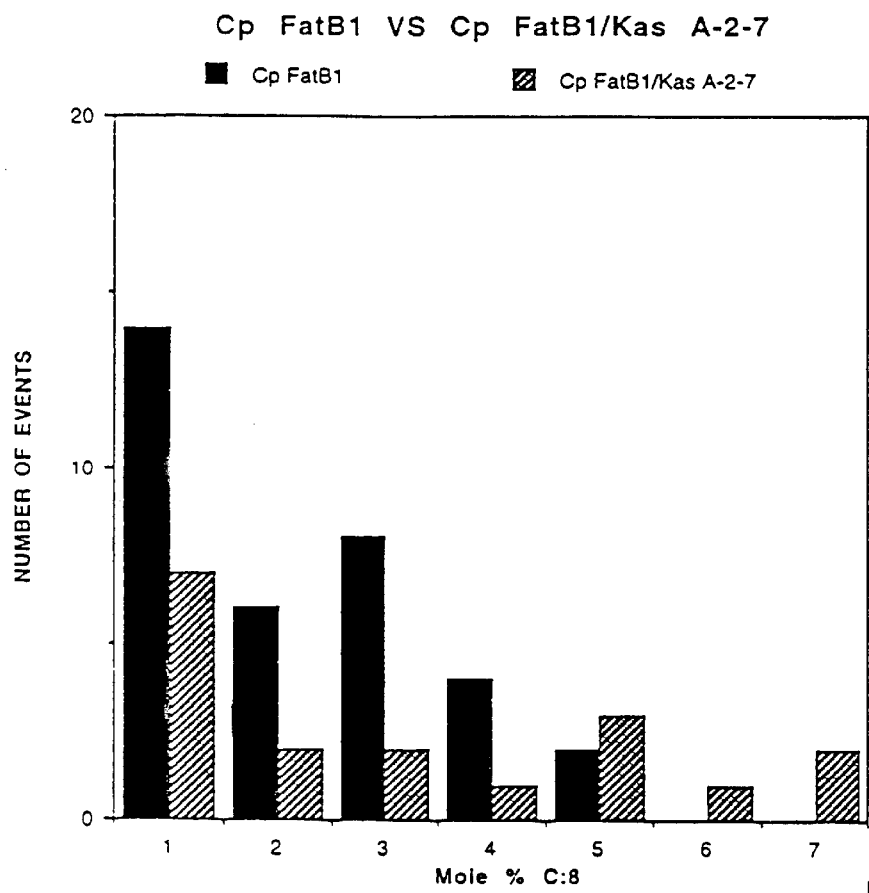
FIG. 14. A graph showing the number of plants arranged according to C8:0 content for transgenic plants containing CpFatB1 versus transgenic plants containing CpFatB1+ chKAS A-2-7 is provided.

Fatty acid analysis of 36 transgenic lines containing cpFatB1 (5400 lines) showed increased levels of C:8 and C:10 in transgenic seeds. The highest level of C:8 observed in a pool seed sample was 4.2 mol %. The C:10 levels were between 30 and 35% of the C:8 content. Fatty acid analysis of 25 transgenic lines containing the TE/KAS A tandem (5413 lines) demonstrated an overall increase in both C:8 and C:10 levels relative to those observed with TE containing lines (5400) alone. In lines containing the cpFatB1 construct alone, the average level of C:8 average were 1.5 mol %, whereas the C:8 average levels in TE/KAS A tandem containing lines was 2.37 mol %. The ratio of C:8 to C:10 remained constant in both populations. The number of transgenic events relative to the C:8 content are presented in FIG. 14. These data show that the transgenic events with tandem TE/KAS A construct yield more lines with higher levels of C:8 than those events with single TE construct. For example, several lines containing nearly 7 mole % C8 were obtained with the TE/KAS A pCGN5413 construct, whereas the highest C8 containing line from the pCGN5400 TE alone transformation contained 4.2 mole % C8.

Half seed analysis of the T3 generation of transgenic canola plants expressing a ChFatB2 (*C. hookeriana* thioesterase; Dehesh et al. (1996) *The Plant Journal* 9:167–172) indicate that these plant can accumulate up to 22 weight % (33 mol %) of 8:0 and 10:0 fatty acids (48044-22-357). Segregation analysis shows that these transformants contain two loci and that they are now homozygous. Selected plants grown from these half seeds were transferred into the greenhouse and later crossed with T1 transformants that had been transformed with either *Cuphea hookeriana* KAS A (5401) alone or KAS A/CpFatB1 double constructs (5413).

Figure 15A:
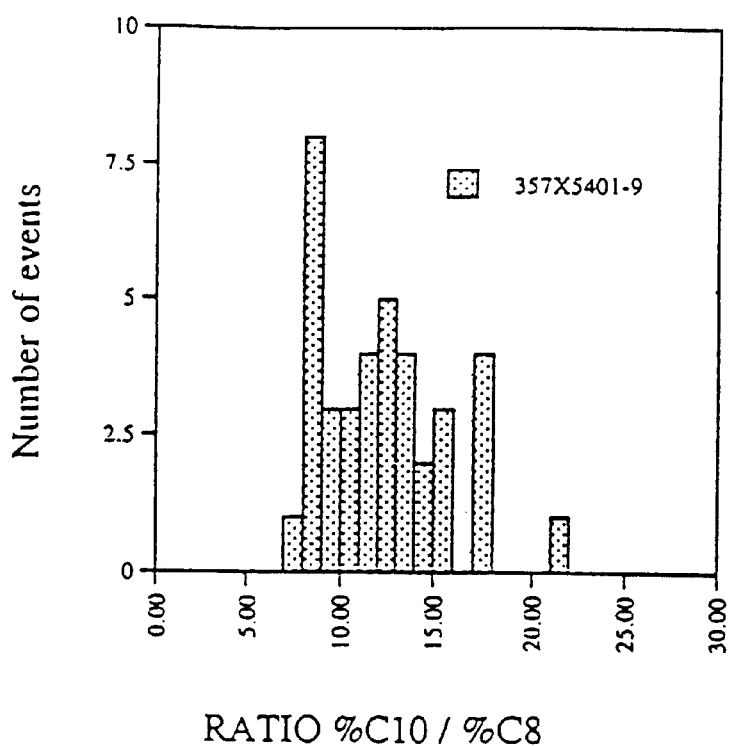
FIG. 15A. Graphs showing the %C10/%C8 ratios in transgenic plants resulting from cross of plants containing ChFatB2 (4804-22-357) and 5401–9 (chKAS A-2–7 plants) is provided.
Figure 15B:
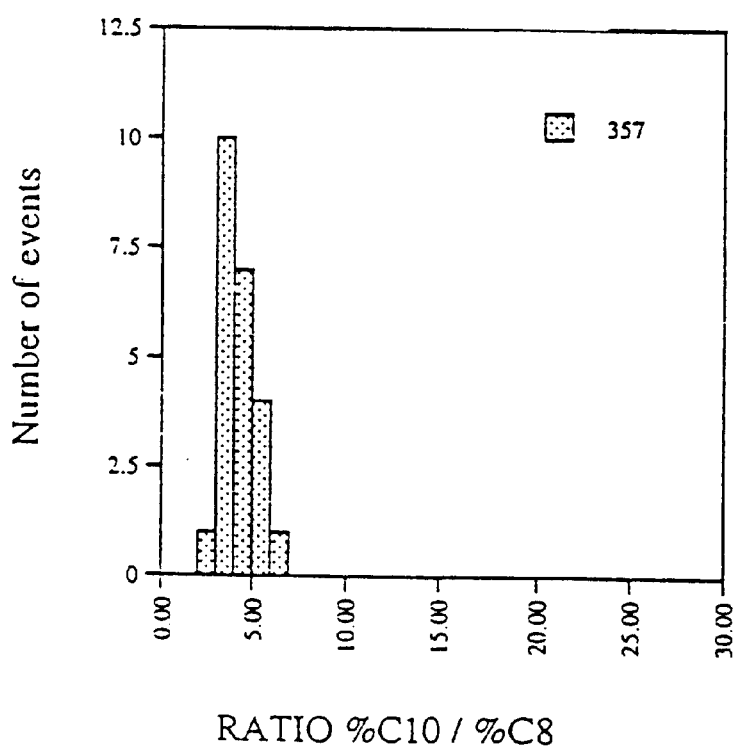
FIG. 15B. Graph showing the %C10/%C8 ratio in transgenic plants containing ChFatB2 (4804–22–357) is provided.
Figure 16A:
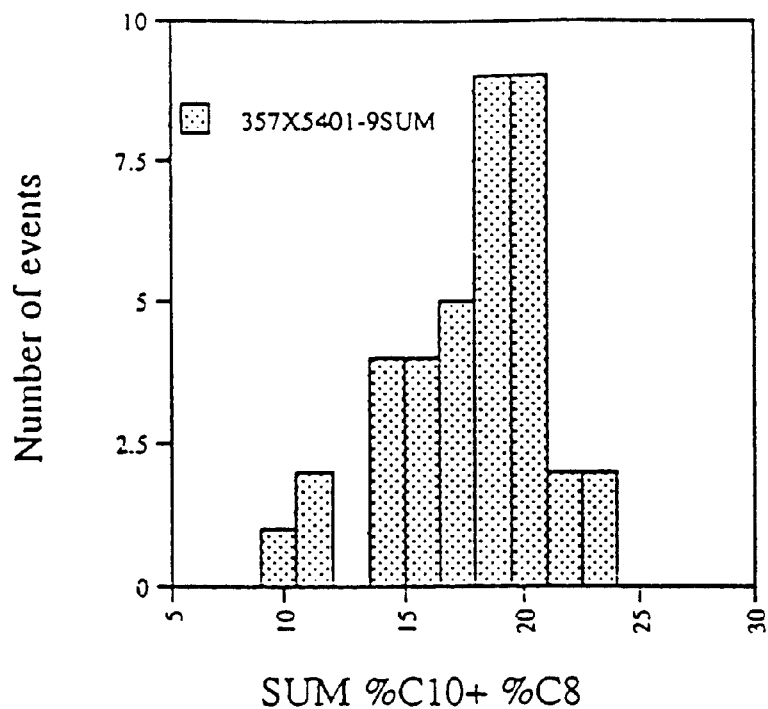
FIG. 16A. Graphs showing the %C10+%C8 content in transgenic plants resulting from cross of plants containing (ChFatB2 (4804–22–357) and 5401–9 (chKAS A-2–7 plants) is provided.
Figure 16B:
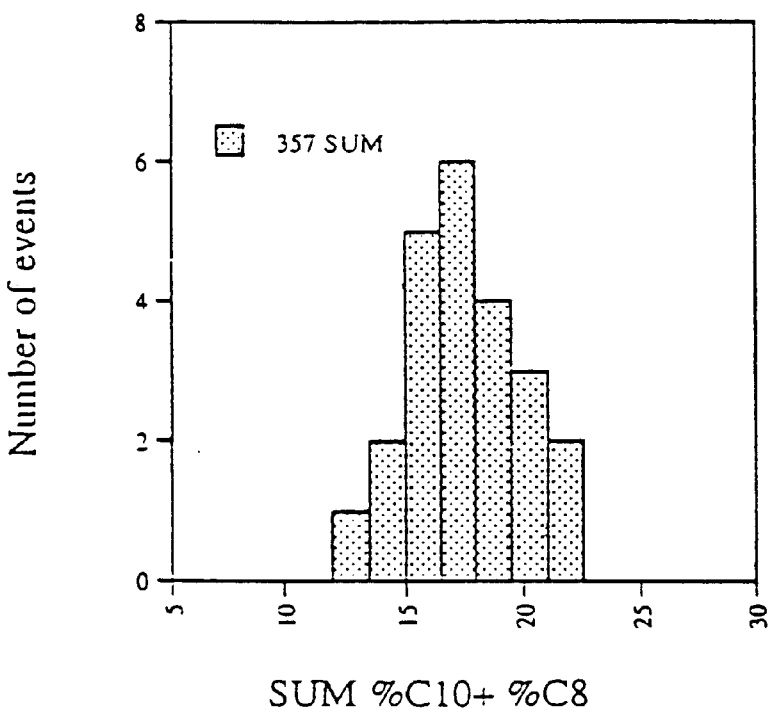
FIG. 16B. Graph showing the %C10+%C8 content in transgenic plants containing ChFatB2 (4804–22–357) is provided.

Fatty acid analysis of several events resulting from the crosses between transgenic lines containing ChFatB2 (4804-22-357) and chKAS A-2-7 (5401-9), reveal an increase in the ratio of C:10/C:8 levels (FIGS. 15A and 15B). This C:10/C:8 ratio in nearly all of the transgenic events containing ChFatB2 TE alone fluctuates between 3 and 6, whereas in the F1 generation of transgenic containing both the TE and the KAS A-2-7, the ratio can be as high as 22. This increase in C:10 levels is accompanied by an increase in the total C:8 and C:10 content (FIGS. 16A and 16B). The sum of the C:8 and C:10 fatty acids in the heterozygous F1 lines is as high as those in the homozygous parent line (4804-22-357), whereas the heterozygous lines usually contain substantially less C:8 and C:10 than the homozygous lines.

Figure 17A:
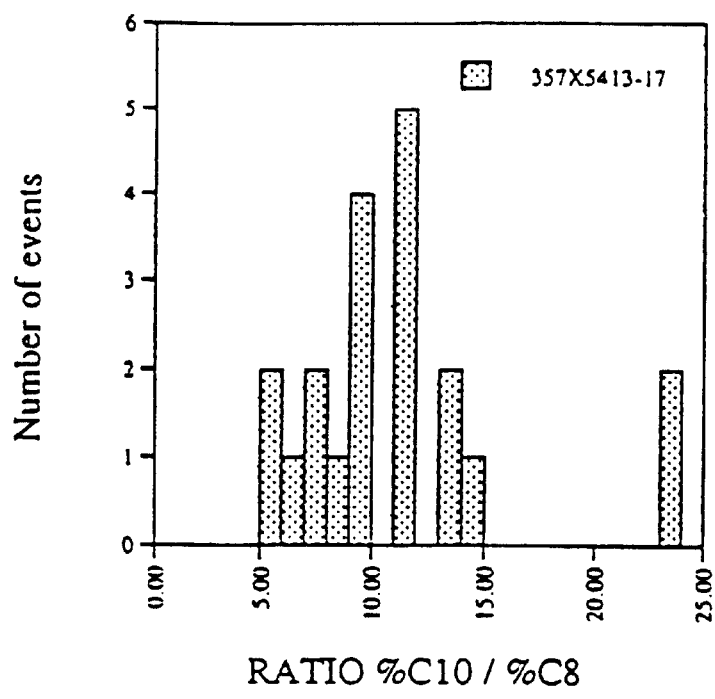
FIG. 17A. Graphs showing the %C10/%C8 ratios in transgenic plants resulting from cross of plants containing ChFatB2 (4804-22-357) and 5413-17 (chKAS A-2-7+ CpFatB1 plants) is provided.
Figure 17B:
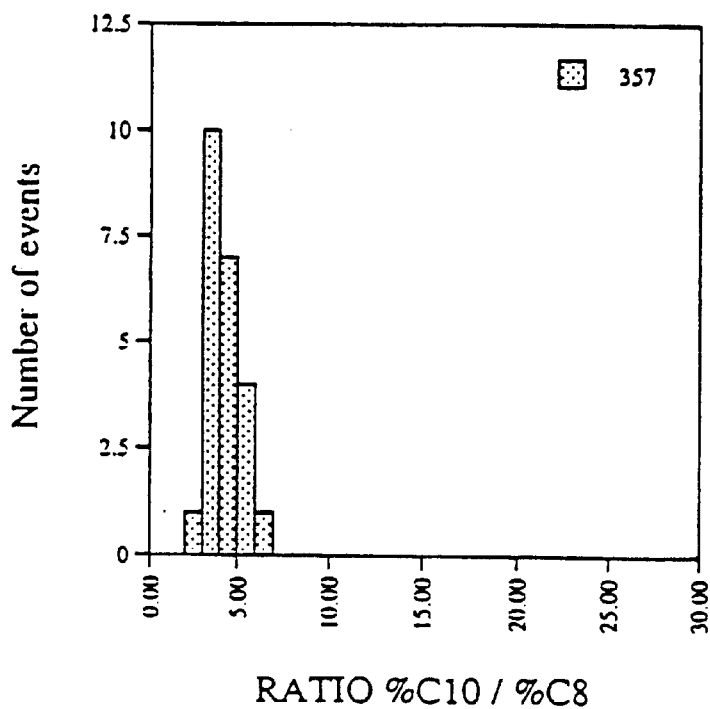
FIG. 17B. Graph showing showing the %C10/%C8 ratio in transgenic plants containing ChFatB2 (4804-22-357) is provided.
Figure 18A:
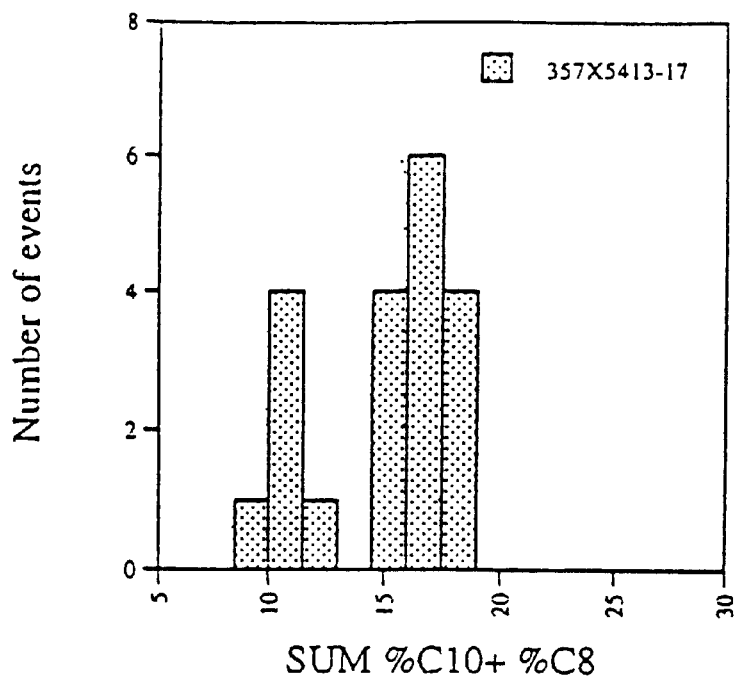
FIG. 18A. Graphs showing the %C10+%C8 content in transgenic plants resulting from cross of plants containing ChFatB2 (4804-22-357) and 5413-17 (chKAS A-2-7+ CpFatB1 plants) is provided.
Figure 18B:
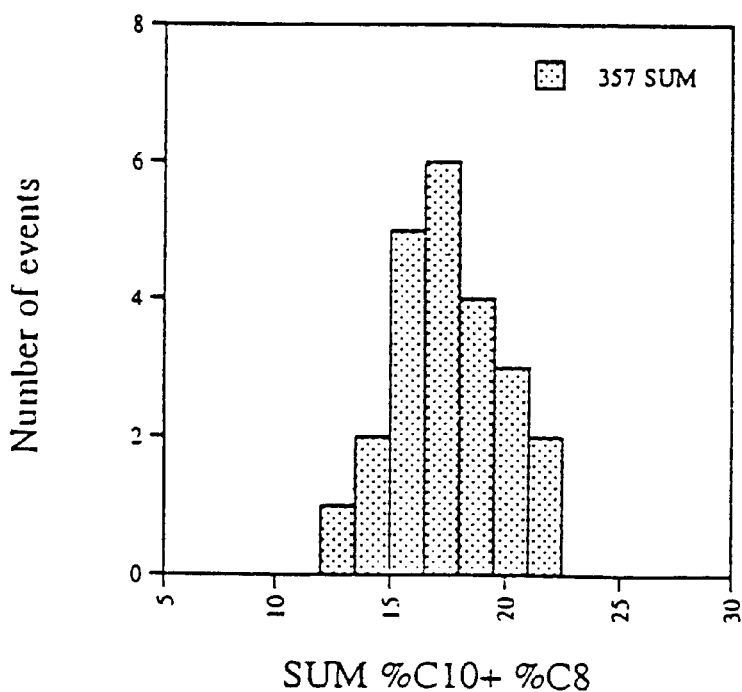
FIG. 18B. Graph showing the %C10+%C8 content in transgenic plants containing ChFatB2 (4804-22-357) is provided.

Similar results were observed in F1 generation seeds resulting from crosses performed between 4804-22-357 (ChFatB2 ) and the 5413-17 event (CpFatB1 and chKAS A-2-7 tandem). Levels of C:8 and C:10 in the 5413-17 line were 6.3 and 2.8 mol % respectively. Data presented in FIGS. 17A and 17B show that there is shift towards C:10 fatty acids as was observed with the 4804-22-357 (ChFatB2)×5401-9 (chKAS A-2-7) crosses. Furthermore, FIGS. 18A and 18B indicates the presence of two separate populations of heterozygotes. Those containing approximately 9–11 weight percent C:10+C:8 are believed to represent offspring containing a single copy of the ChFatB1 TE gene and no copies of the CpFatB1 and chKAS A genes from 5413. Those plants containing approximately 15–20 weight percent C:10+C:8 are believed to represent the heterozygotes containing a single ChFatB1 TE gene as well as the CpFatB1 and chKAS A genes from 5413. Thus, the level of the C:10+C:8 fatty acids does not decrease to 50% of that detected in parent lines when a copy of the ChKAS A gene is present.

To further characterize the chain length specificity of the *Cuphea hookeriana* KAS A enzyme, crosses between transgenic *Brassica napus* lines containing a California Bay (*Umbellularia californica*) 12:0 specific thioesterase, Uc FatB1 (U.S. Pat. No. 5,344,771) and chKAS A-2-7 (5401-9) were made. Half seed analysis of transgenic plants containing Uc fatB1 have previuosly indicated that these plants can accumulate up to 52 mol % C12:0 in the seed oil of homozygous dihaploid lines (LA86DH186). Crosses between the line LA86DH186 and untransformed control Brassica demonstrated a decrease in the C12:0 levels.

Figures 19A, 19B:
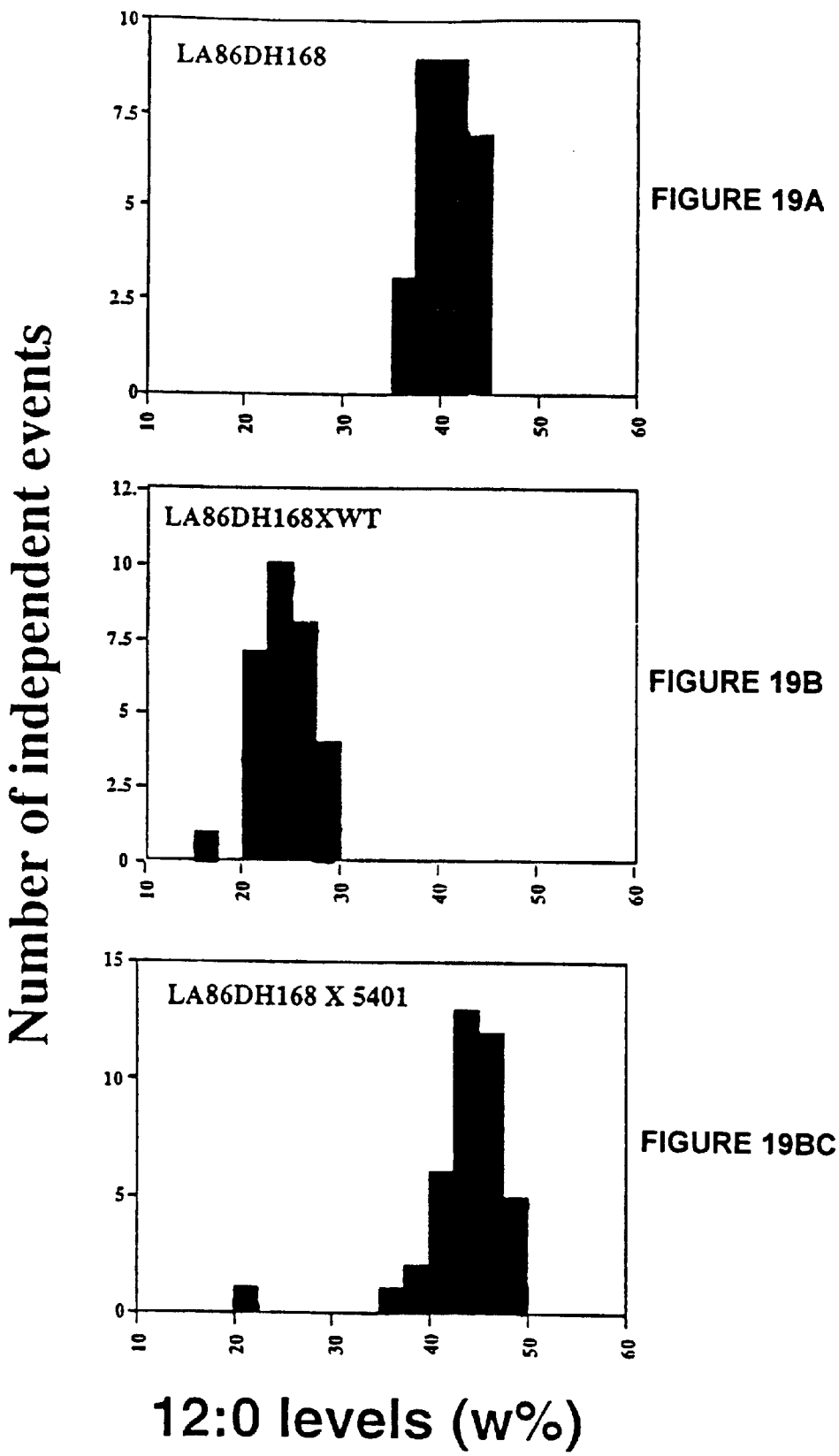
FIG. 19A. Graphs showing the %C12:0 in transgenic plants containing Uc FatB1 (LA86DH186) is provided.
FIG. 19B. Graph showing the %C12:0 in transgenic plants resulting from cross of plants containing Uc FatB1 (LA86DH186) and wild type (X WT) is provided.
Figure 20:
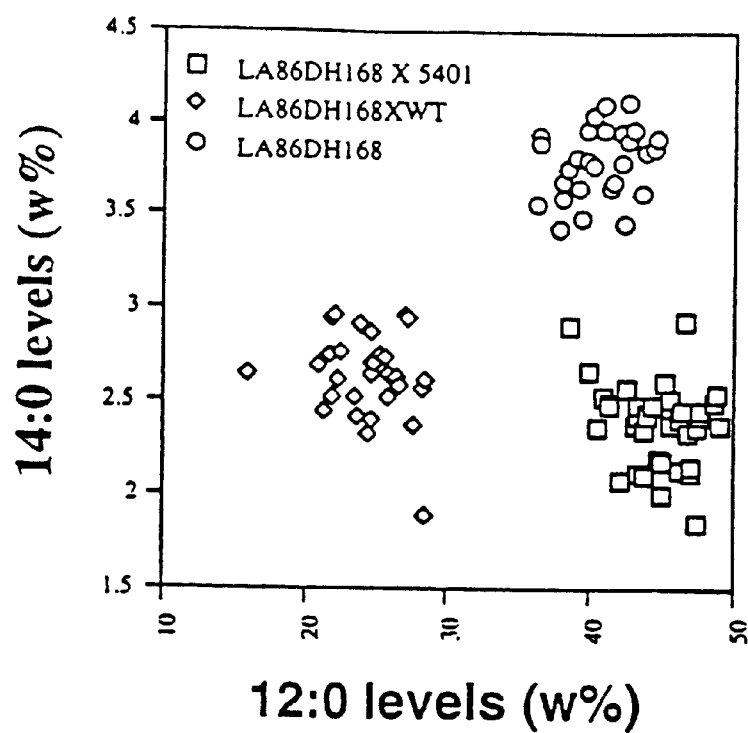
FIG. 20. Graph showing the relative proportions of C12:0 and C14:0 fatty acids in the seeds of transgenic plants containing Uc FatB1 (LA86DH186) and in plants resulting from crosses with wild type (X WT) and with lines expressing Ch KAS A-2-7.

However, crosses between LA86DH186 and the 5401-9 hemizygous line led to an accumulation of up to 57 mol % C12:0 in the seed oil of F1 progeny (FIGS. 19A and 19B). Interestingly, in crosses with LA86DH186×untransformed control line and LA86DH186×5401-9, levels of C14:0 in the seeds of the F1 progeny decreased to 50% of the levels obtained in homozygous LA86DH186 lines (FIG. 20). Furthermore, increases in the proportion of C12:0 fatty acid resulted in a substantial decline in the proportions of all the long-chain fatty acyl groups (C16:0, C18:0, C18:2, and C18:3). These results indicate that the ChKAS A-2-7 is an enzyme with substrate specificity ranging from C6:0 to C10:0-ACP, and that its over-expression ultimately reduces the longer chain acyl-ACP pools.

Figures 21A, 21B, 21C:
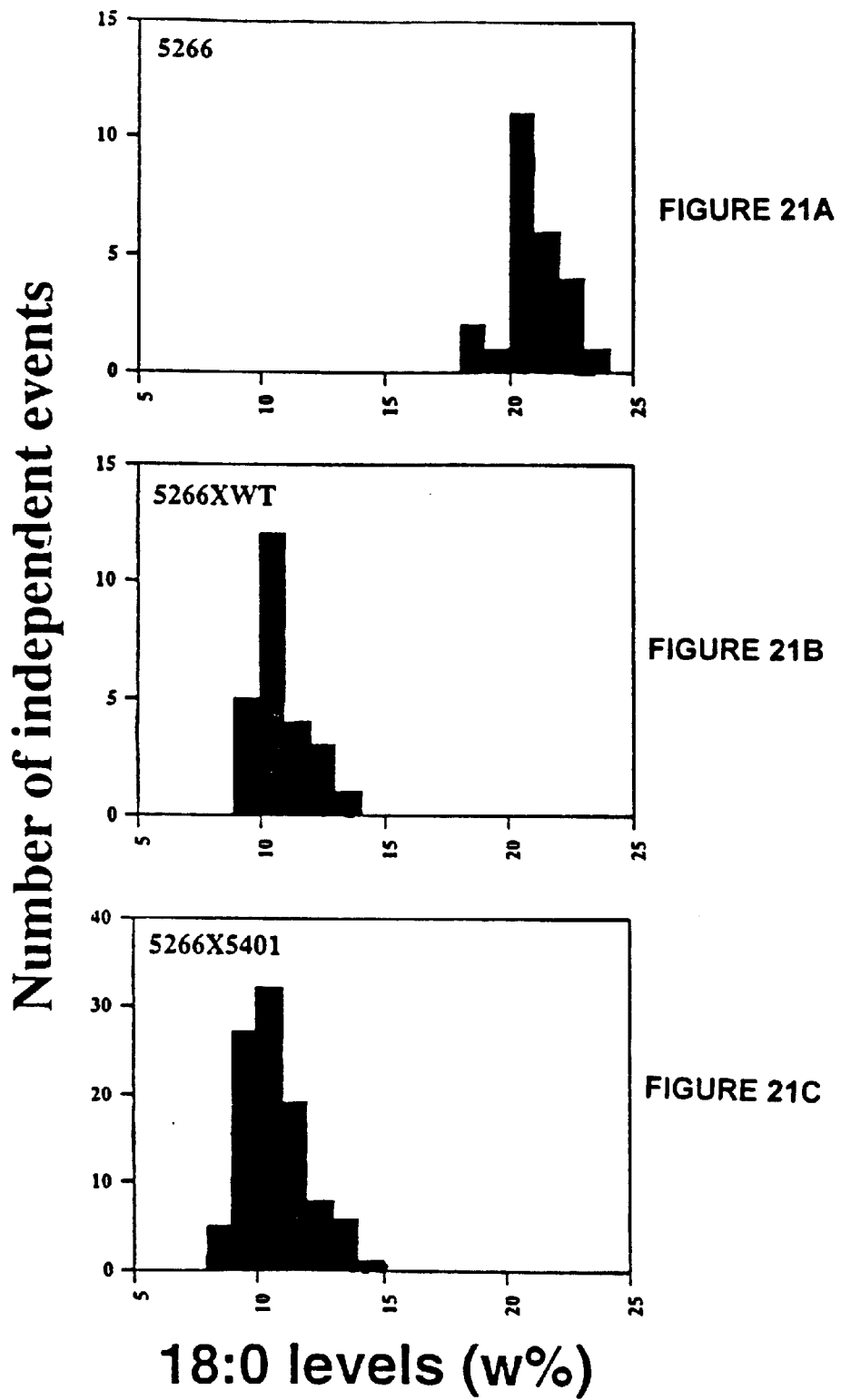
FIG. 21A. Graphs showing the %C18:0 in transgenic plants containing Garm FatB1 (5266) is provided.
FIG. 21B. Graph showing the %C18:0 in transgenic seeds resulting from cross of plants containing Garm FatB1 (5266) and wild type (X WT) is provided.
FIG. 21C. Graph showing the %C18:0 in transgenic seeds of plants resulting from cross of plants containing Garm FatB1 (5266) and lines expressing Ch KAS A-2-7 is provided.

Further evidence is obtained in support of the chain length specificity of the ChKAS A-2-7 in crosses of the 5401-9 line with a transgenic line (5266) expressing an 18:1/18:0 TE from *Garcinia mangostana* (GarmFatA1 , U.S. patent application Ser. No. 08/440,845). Transgenic Brassica line 5266 has been shown to accumulate up to 24 mol % C18:0 in the seed oil of homozygous lines (FIGS. 21A, 21B and 21C). However, in the seed oil of F1 progeny of crosses between 5266 and 5401-9 levels of C18:0 were reduced to approximately 12 mol %. Furthermore, levels of C16:0 generated from these crosses was similar to the levels obtained from the seed oil of nontransgenic control plants.

Example 5
In vitro Analysis of Plant KAS Enzymes

Seed extracts were prepared from developing seeds of nontransgenic controls or transgenic Brassica expressing chKAS A-2-7 as described in Slabaugh et al. (*Plant Journal*, 1998 in press) and Leonard et al. (*Plant Journal*, 1998, in press). In vitro fatty acid synthesis assays were performed as described by Post-Beittenmiller (*J. Biol. Chem.* (1991), 266:1858–1865). Extracts were concentrated by ammonium sulfate precipitation and desalting using P-6 columns (Bio-Rad, Hercules, Calif.). Reactions (65 $\mu$l) contained 0.1M Tris/HCl (pH 8.0), 1 mM dithiothreitol, 25 mM recombinant spinach ACP1, 1 mM NADH, 2 mM NADPH, 50 $\mu$M malonyl-CoA, 10 $\mu$M [1-$^{14}$C]acetyl-CoA (50 mCi/mmol), 1 mg/ml BSA, and 0.25 mg/ml seed protein. Selected seed extracts were preincubated with cerulenin at 23° C. for 10 min. Reaction products were separated on an 18% acrlamide gel containing 2.25M urea, electroblotted onto to nitrocellulose and quntitated by phosporimaging using Image QuaNT software (Molecular Dynamics, Sunnyvale, Calif.). Authentic acyl-ACPs were run in parallel, immunoblotted and finally detected by anti-ACP serum to confirm fatty acid chain lengths.

Figure 22:
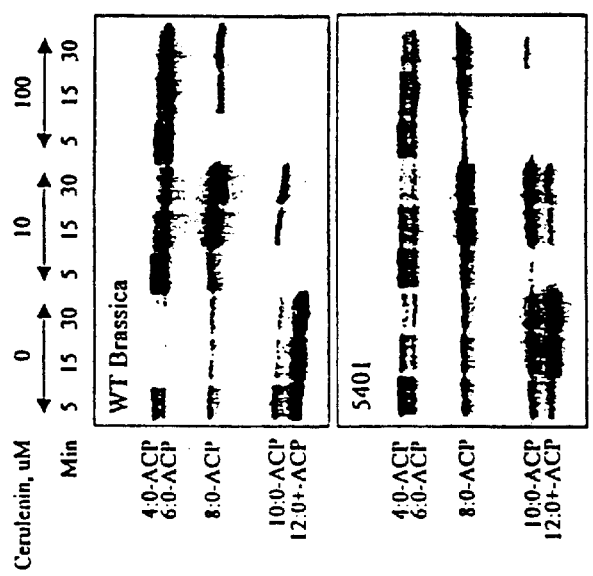
FIG. 22. The activity profile of Ch KAS A in protein extracts from transgenic plants containing Ch KAS A-2-7. Extracts were preptreated with the indicated concentrations of cerulenin.

The results (FIG. 22) indicate that the fatty acid synthesis capabilities of transgenic Brasica (5401-9) seed extracts was greater than that obtained from in the nontransgenic controls as measured by the relative abundance of C8:0- and C10:0-ACP at all time points tested. In addition, pretreatment of the extracts with cerulenin, markedly reduced the synthesis of longer chain fatty acids in both the transgenic and nontransgenic control seed extracts. However, the extension of the spinach-ACP was much less inhibited in the seed extracts from the transgenic lines than in the seed extracts of nontransgenic control Brassica.

These data further support that Ch KAS A-2-7 is a condensing enzyme active on medium chain acyl-ACPs, and that expression of this enzyme in plants results in enlarged substrate pools to be hydrolyzed by medium-chain specific thioesterases. Furthermore, these data suggest that chKAS A-2-7 also is a cerulenin-resistant condensing enzyme.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A DNA construct comprising a coding sequence as set forth in SEQ ID NO:5.

2. A DNA construct comprising a coding sequence for a β-keto acyl-ACP synthase factor A protein encoding an amino acid sequence as set forth in SEQ ID NO:6.

* * * * *